United States Patent
Thomson et al.

(10) Patent No.: US 8,486,962 B2
(45) Date of Patent: Jul. 16, 2013

(54) ANTIFUNGAL AGENTS

(75) Inventors: Samantha Patricia Thomson, Manchester (GB); Rhian Teresa Davies, Manchester (GB); Nigel Mark Allanson, Manchester (GB); Alexandre Kuvshinov, Manchester (GB); Gareth Morse Davies, Macclesfield (GB); Philip Neil Edwards, Bramhall (GB)

(73) Assignee: F2G Ltd., Greater Manchester (GB)

( * ) Notice: Subject to any disclaimer, the term of this patent is extended or adjusted under 35 U.S.C. 154(b) by 637 days.

(21) Appl. No.: 11/914,516

(22) PCT Filed: May 18, 2006

(86) PCT No.: PCT/GB2006/001820
§ 371 (c)(1),
(2), (4) Date: Nov. 15, 2007

(87) PCT Pub. No.: WO2006/123145
PCT Pub. Date: Nov. 23, 2006

(65) Prior Publication Data
US 2008/0161302 A1    Jul. 3, 2008

(30) Foreign Application Priority Data

May 18, 2005  (GB) .................................. 0510190.2
Apr. 20, 2006 (GB) .................................. 0607841.4

(51) Int. Cl.
*A61K 31/437* (2006.01)
*A01P 3/00* (2006.01)
*A01N 43/52* (2006.01)

(52) U.S. Cl.
USPC .................. 514/299; 514/233.2; 514/253.04; 546/112; 424/405

(58) Field of Classification Search
USPC .......................................... 514/299; 546/112
See application file for complete search history.

(56) References Cited

U.S. PATENT DOCUMENTS
6,645,976 B1  11/2003  Dillard et al.

FOREIGN PATENT DOCUMENTS
WO    WO-96/03383      2/1996
WO    WO-02/098876    12/2002
WO    WO-2004/082606   9/2004

OTHER PUBLICATIONS

Ames et al., "The preparation of aminoalkylpyrrocolines", Chem. Soc., 1959, 620-622.
Blondeau et al., "Synthesis of New Phenols. Part 1. Derivatives of 8-hydroxy-2-phenylindolizine", J. Chem. Research (S), 1981, 366-367.
Dick et al., "Heterocyclic compounds with bridgehead nitrogen atoms. Part 9. Synthesis in the pyrrolo[2,1,5-de]quinolizine ([2.3.3]cyclazine) series starting from indolizines", J. Chem. Soc., Perkin Trans. 1, 1981, 3150-3157.
Galbraith et al., "The Formation of Cycl[3.2.2]azine Derivatives via the Reaction of Pyrrocoline with Dimethyl Acetylenedicarboxylate", J. of the American Chemical Society, Jan. 20, 1961, 453-458, vol. 83.
Groll et al., "Trends in the postmortem epidemiology of invasive fungal infections at a university hospital", J Infect., Jul. 1996; 23-32; vol. 33(1).
Guet et al., "Synthesis of New Phenols. Part 2. Derivatives of 6-hydroxy-2-phenylindolizine", J. Chem Research (S), 1982, 245.
Hagishita et al., "Potent Inhibitors of Secretory Phospholipase A2: Synthesis and Inhibitory Activities of Indolizine and Indene Derivatives", J. Med. Chem., 1996, 3636-3658, vol. 39(19).
Holland et al., "The chemistry of the pyrrocolines. Part VII. Further experiments with 2-methylpyrrocoline", J. Chem. Soc., 1955, 1504-1511.
Ribaud et al., "Survival and prognostic factors of invasive aspergillosis after allogeneic bone marrow transplantation", Clin Infect Dis. Feb. 1999; 322-30; vol. 28(2).
Shipman, "Product Class 16: Indolizines", Science of Synthesis, 2001, 745-787, 10.16.
Venturella, "Arylindolizines III. Methoxyl and glyoxyl derivatives of several substituted phenylindolizines", Journal of Pharmaceutical Sciences, 1166-1169, vol. 53(10).

*Primary Examiner* — Kortney L Klinkel
(74) *Attorney, Agent, or Firm* — Fulbright & Jaworski LLP

(57) ABSTRACT

Compounds of formula (I), and pharmaceutically acceptable salts thereof, may be used in therapy, for example as antifungal agents: (I) wherein: R1, R2, R3, R4, R5, R6, R7, X and $X^1$ are as defined herein. Certain compounds of formula (I) are also provided. Compounds of formula (T), and agriculturally acceptable salts thereof, may also be used as agricultural fungicides.

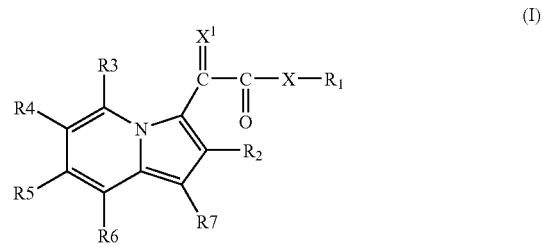

27 Claims, No Drawings

ANTIFUNGAL AGENTS

FIELD OF THE INVENTION

This invention relates to indolizine compounds and their therapeutic use in prevention or treatment of fungal diseases. It also relates to the use of the compounds as agricultural fungicides.

BACKGROUND OF THE INVENTION

Invasive fungal infections are well recognised as diseases of the immunocompromised host. Over the last twenty years there have been significant rises in the number of recorded instances of fungal infection (Groll et al., 1996. Trends in the postmortem epidemiology of invasive fungal infections at a university hospital. *J Infect* 33, 23-32). In part this is due to increased awareness and improved diagnosis of fungal infection. However, the primary cause of this increased incidence is the vast rise in the number of susceptible individuals. This is due to a number of factors including new and aggressive immunosuppressive therapies, increased survival in intensive care, increased numbers of transplant procedures and the greater use of antibiotics worldwide.

In certain patient groups, fungal infection occurs at high frequency; lung transplant recipients have a frequency of up to 20% colonisation and infection with a fungal organism and fungal infection in allogenic hoemopoetic stem transplant recipients is as high as 15% (Ribaud et al., 1999, Survival and prognostic factors of invasive aspergillosis after allogeneic bone marrow transplantation. *Clin Infect Dis.* 28:322-30).

Currently only four classes of antifungal drug are available to treat systemic fungal infections. These are the polyenes (e.g., amphotericin B), the azoles (e.g., ketoconazole or itraconazole) the echinocandins (e.g., caspofungin) and flucytosine.

The polyenes are the oldest class of antifungal agent being first introduced in the 1950's. The exact mode of action remains unclear but polyenes are only effective against organisms that contain sterols in their outer membranes. It has been proposed that amphotericin B interacts with membrane sterols to produce pores allowing leakage of cytoplasmic components and subsequent cell death.

Azoles work by inhibition of the 14α-demethylase via a cytochrome P450 dependent mechanism. This leads to a depletion of the membrane sterol ergosterol and the accumulation of sterol precursors resulting in a plasma membrane with altered fluidity and structure.

Echinocandins work by the inhibition of the cell wall synthetic enzyme β-glucan synthase. This leads to abnormal cell wall formation, osmotic sensitivity and cell lysis.

Flucytosine is a pyrimidine analogue interfering with cellular pyrimidine metabolism as well DNA, RNA and protein synthesis. However widespread resistance to flucytosine limits its therapeutic use.

It can be seen that to date the currently available antifungal agents act primarily against only two cellular targets; membrane sterols (polyenes and azoles) and β-glucan synthase (echinocandins).

Resistance to both azoles and polyenes has been widely reported leaving only the recently introduced echinocandins to combat invasive fungal infections. As the use of echinocandins increases resistance by fungi will inevitably occur.

The identification of new classes of antifungal agent is required to give the promise of positive therapeutic outcomes to patients.

WO 2004082606 discloses certain 2-indolizin-3-yl-2-oxo-acetamides as TNFα and/or PDE4 inhibitors, which may be used for the treatment of cancer, inflammatory disorders, and autoimmune diseases. These compounds differ from the present invention as the 2-position of the indolizine (i.e. R2 in this invention) is unsubstituted.

U.S. Pat. No. 6,645,976, WO 9603383 and J. Med. Chem. 1996, 39, (19), 3636 disclose the preparation of (1-benzyl-6-(3-carboxypropyloxy)-2-ethyl-indolizin-3-yl)glyoxylamide and its use as a sPLA$_2$ inhibitor. This compound and its intermediates differ from the present invention as they contain a benzyl group in position 1 of the indolizine (i.e. R7 in this invention).

The following compounds which may be used in the present invention are commercially available and are sold without mention of use:

alpha-Oxo-2-phenyl-N-(4,5,6,7-tetrahydro-2-benzothiazolyl)-3-indolizineacetamide,
N-Cyclohexyl-alpha-oxo-2-phenyl-3-indolizineacetamide,
N-(2,4-Dimethyl-5-nitrophenyl)-alpha-oxo-2-phenyl-3-indolizineacetamide,
N-[3-[(Diethylamino)sulfonyl]phenyl]-alpha-oxo-2-phenyl-3-indolizineacetamide,
N-[2-[4-(Aminosulfonyl)phenyl]ethyl]-alpha-oxo-2-phenyl-3-indolizineacetamide,
2-Chloro-4-fluoro-benzoic acid 3-[[oxo-(2-phenyl-3-indolizinyl)acetyl]amino]propyl ester,
N-[2-(1,1-Dimethylethyl)phenyl]-alpha-oxo-2-phenyl-3-indolizineacetamide,
N-(3-Bromophenyl)-alpha-oxo-2-phenyl-3-indolizineacetamide,
3,5-Dimethyl-1-[oxo(2-phenyl-3-indolizinyl)acetyl]-piperidine,
N-(2-Hydroxyethyl)-alpha-oxo-2-phenyl-3-indolizineacetamide,
N-[2-[(4-Nitrobenzoyl)oxy]ethyl]-alpha-oxo-2-phenyl-3-indolizineacetamide,
2-(4-Chlorophenyl)-alpha-oxo-3-Indolizineacetic acid (2-fluorophenyl)methyl ester,
4-Fluoro-benzoic acid 2-[[[2-(4-chlorophenyl)-3-indolizinyl]oxoacetyl]amino]ethyl ester,
1-[[2-(4-Chlorophenyl)-3-indolizinyl]oxoacetyl]hexahydro-1H-azepine,
2-(4-Chlorophenyl)-alpha-oxo-3-indolizineacetic acid cyclopentyl ester,
2-(4-Chlorophenyl)-N-(2-hydroxyethyl)-alpha-oxo-3-indolizineacetamide,
4-(1,1-Dimethylethyl)-benzoic acid 2-[[[2-(4-chlorophenyl)-3-indolizinyl]oxoacetyl]amino]ethyl ester,
1-[Oxo(2-phenyl-3-indolizinyl)acetyl]-4-phenyl-piperazine,
2,6-Dimethyl-4-[oxo(2-phenyl-3-indolizinyl)acetyl]-morpholine,
N-1,3-Benzodioxol-5-yl-2-(4-chlorophenyl)-alpha-oxo-3-indolizineacetamide,
N-(4-Ethoxyphenyl)-alpha-oxo-2-phenyl-3-indolizineacetamide,
N-(2,4-Dimethylphenyl)-alpha-oxo-2-phenyl-3-indolizineacetamide,
N-(3-Hydroxypropyl)-alpha-oxo-2-phenyl-3-indolizineacetamide,
N-Methyl-N-(1-methyl-4-piperidinyl)-alpha-oxo-2-phenyl-3-indolizineacetamide,
N-[3-[(Diethylamino)sulfonyl]-4-methylphenyl]-alpha-oxo-2-phenyl-3-indolizineacetamide,
N-(6-Methoxy-3-pyridinyl)-alpha-oxo-2-phenyl-3-indolizineacetamide, N-(3-Methoxyphenyl)-alpha-oxo-2-phenyl-3-indolizineacetamide,
N-[4-Methyl-3-(4-morpholinylsulfonyl)phenyl]-alpha-oxo-2-phenyl-3-indolizineacetamide,
alpha-Oxo-2-phenyl-N-[3-(1-piperidinylsulfonyl)phenyl]-3-indolizineacetamide,
N-(4-Chloro-2-methoxy-5-methylphenyl)-alpha-oxo-2-phenyl-3-indolizineacetamide,
N-(2-Chloro-3-pyridinyl)-alpha-oxo-2-phenyl-3-indolizineacetamide,
N-[2-[[(4-Chlorophenyl)amino]carbonyl]phenyl]-alpha-oxo-2-phenyl-3-indolizineacetamide,
N-[5-[(Diethylamino)sulfonyl]-2-(4-morpholinyl)phenyl]-alpha-oxo-2-phenyl-3-indolizineacetamide,
alpha-Oxo-N-(3-phenoxyphenyl)-2-phenyl-3-indolizineacetamide,
alpha-Oxo-2-phenyl-N-[4-(trifluoromethyl)phenyl]-3-indolizineacetamide,
alpha-Oxo-2-phenyl-N-[4-(1-piperidinyl)phenyl]-3-indolizineacetamide,
4-Chloro-2-nitro-benzoic acid 3-[[oxo(2-phenyl-3-indolizinyl)acetyl]amino]propyl ester,
3-[(2,6-Dimethyl-4-morpholinyl)sulfonyl]-benzoic acid 3-[[oxo(2-phenyl-3-indolizinyl)acetyl]amino]propyl ester,
N-(2,3-Dihydro-1,5-dimethyl-3-oxo-2-phenyl-1H-pyrazol-4-yl)-alpha-oxo-2-phenyl-3-indolizineacetamide,
N-(3,5-Dimethoxyphenyl)-alpha-oxo-2-phenyl-3-indolizineacetamide,
N-(3-Chloro-4-fluorophenyl)-alpha-oxo-2-phenyl-3-indolizineacetamide,
N-[4-[(Diethylamino)sulfonyl]phenyl]-alpha-oxo-2-phenyl-3-indolizineacetamide,
N-(3,4-Dimethylphenyl)-alpha-oxo-2-phenyl-3-indolizineacetamide,
alpha-Oxo-N-(2-phenoxyphenyl)-2-phenyl-3-indolizineacetamide,
N-[5-(1,1-Dimethylethyl)-2-methoxyphenyl]-alpha-oxo-2-phenyl-3-indolizineacetamide,
alpha-Oxo-2-phenyl-N-[4-(1-piperidinylsulfonyl)phenyl]-3-indolizineacetamide,
N-(2,3-Dimethylphenyl)-alpha-oxo-2-phenyl-3-indolizineacetamide,
N-(4-Bromo-2-fluorophenyl)-alpha-oxo-2-phenyl-3-indolizineacetamide,
N-2-Naphthalenyl-alpha-oxo-2-phenyl-3-indolizineacetamide,
N-[2-Chloro-5-(4-morpholinylsulfonyl)phenyl]-alpha-oxo-2-phenyl-3-indolizineacetamide,
2,3-Dichloro-benzoic acid 3-[[oxo(2-phenyl-3-indolizinyl)acetyl]amino]propyl ester,
3,4-Dichloro-benzoic acid 3-[[oxo(2-phenyl-3-indolizinyl)acetyl]amino]propyl ester,
N-(2,4-Dimethoxyphenyl)-alpha-oxo-2-phenyl-3-indolizineacetamide,
2-(4-Chlorophenyl)-alpha-oxo-N-phenyl-3-indolizineacetamide,
4-[[2-(4-Chlorophenyl)-3-indolizinyl]oxoacetyl]-morpholine,
N-Ethyl-alpha-oxo-2-phenyl-3-indolizineacetamide,
alpha-Oxo-2-phenyl-N-[3-(trifluoromethyl)phenyl]-3-indolizineacetamide,
4-[[Oxo(2-phenyl-3-indolizinyl)acetyl]amino]-benzoic acid methyl ester,
N,N-Diethyl-alpha-oxo-2-phenyl-3-indolizineacetamide,
N-[2-(Dimethylamino)ethyl]-alpha-oxo-2-phenyl-3-indolizineacetamide,
2-Methyl-alpha-oxo-3-indolizineacetic acid,
N-(2-Methoxyphenyl)-alpha-oxo-2-phenyl-3-indolizineacetamide,
N-1-Naphthalenyl-alpha-oxo-2-phenyl-3-indolizineacetamide,
1,2,3,4-Tetrahydro-6,7-dimethoxy-2-[oxo(2-phenyl-3-indolizinyl)acetyl]-isoquinoline,
N-(1-Cyano-1-methylethyl)-alpha-oxo-2-phenyl-3-indolizineacetamide,
alpha-Oxo-2-phenyl-N-(2-phenylethyl)-3-indolizineacetamide,
Hexahydro-1-[oxo(2-phenyl-3-indolizinyl)acetyl]-1H-azepine,
alpha-Oxo-2-phenyl-N-4H-1,2,4-triazol-4-yl-3-indolizineacetamide,
1,2,3,4-Tetrahydro-1-[oxo(2-phenyl-3-indolizinyl)acetyl]-quinoline,
N-(6-Methoxy-2-benzothiazolyl)-alpha-oxo-2-phenyl-3-indolizineacetamide,
alpha-Oxo-2-phenyl-N-2-thiazolyl-3-indolizineacetamide,
N-[(4-Methoxyphenyl)methyl]-alpha-oxo-2-phenyl-3-indolizineacetamide,
N-[(4-Bromophenyl)methyl]-alpha-oxo-2-phenyl-3-indolizineacetamide,
N-(1,1-Dimethylethyl)-alpha-oxo-2-phenyl-3-indolizineacetamide,
N-Butyl-alpha-oxo-2-phenyl-3-indolizineacetamide,
alpha-Oxo-N-[(3-phenoxyphenyl)methyl]-2-phenyl-3-indolizineacetamide,
N-Ethyl-alpha-oxo-N,2-diphenyl-3-indolizineacetamide,
alpha-Oxo-N,2-diphenyl-3-indolizineacetamide,
N-[2-(3,4-Dimethoxyphenyl)ethyl]-alpha-oxo-2-phenyl-3-indolizineacetamide,
alpha-Oxo-2-phenyl-N-(phenylmethyl)-3-indolizineacetamide,
4-[Oxo(2-phenyl-3-indolizinyl)acetyl]-morpholine,
N-(4-Methylphenyl)-alpha-oxo-2-phenyl-3-indolizineacetamide,
2-Methyl-alpha-oxo-3-indolizineacetic acid ethyl ester,
N,N-Dimethyl-2-phenyl-3-indolizineglyoxylamide,
2-Oxo-2-(2-phenyl-indolizin-3-yl)-N-(4-trifluoromethyl-phenyl)-acetamide,
N-(2,4-Dichloro-phenyl)-2-oxo-2-(2-phenyl-indolizin-3-yl)-acetamide,
2-Oxo-2-(2-phenyl-indolizin-3-yl)-N-(3-trifluoromethyl-phenyl)-acetamide,
2-Oxo-2-(2-phenyl-indolizin-3-yl)-N-(4-piperidin-1-yl-phenyl)-acetamide,

SUMMARY OF THE INVENTION

The present inventors have found that certain indolizine compounds are antifungal. In particular, the compounds inhibit the growth of human pathogenic fungi such as *Aspergillus* and therefore may be used to treat fungal infection and disease.

Accordingly, the present invention provides a compound which is an indolizinyl derivative of formula (I) or a pharmaceutically acceptable salt thereof, for use in a method of treatment of the human or animal body by therapy:

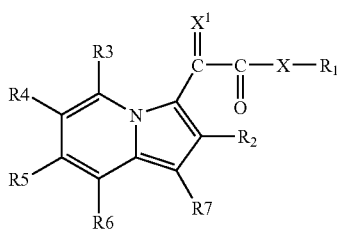

(I)

wherein:

X is a bond, —NR8—, —O—, —S—, —SO—, or —SO₂—;

X¹ is O or NOR9, wherein R9 is hydrogen or an unsubstituted or substituted C1-C4 alkyl group;

R1 and R8 independently represent hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', and —Y—Z;

or when X is NR8, R1 and R8 together with the nitrogen to which they are attached may form an unsubstituted or substituted, aromatic or non-aromatic 5- to 12-membered heterocyclyl group;

A1 is an unsubstituted or substituted C6-C10 arylene group;

L1 is a bond, —NR'—, —O—, —CO—, —OCO—, —OCONR'R" or —CONR'R"—;

L2 is a substituted or unsubstituted C1-C4 alkylene or C2-C4 alkenylene group;

A2 is a substituted or unsubstituted C6-C10 aryl or 5- to 12-membered-heterocyclyl group;

R2 is an unsubstituted or substituted group selected from C6-C10 aryl, a 5- to 12-membered heterocyclyl group, C1-C8 alkyl and C3-C6 cycloalkyl, or halogen;

R3, R4, R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO₂R', —CONR'R", —COR', —CN, —NO₂, —NR'R", CF₃, or —Y—Z;

R7 represents hydrogen, halogen, C1-C8 alkyl, C2-C8 alkenyl, C2-C8 alkynyl, —OR', —CO₂R', —CONR'R", —COR', —CN, —NO₂, —NR'R", CF₃, or —Y—Z;

Y is C1-C8 alkylene, C2-C8 alkenylene or C2-C8 alkynylene;

Z is halogen, C3-C6 cycloalkyl, —OR', —SR', —SOR', —SO₂R', —SO₂NR'R", —SO₃H, —NR'R", —NR'COR', —NO₂, —CO₂R', —CONR'R", —COR', —OCOR', —CN, —CF₃, —NSO₂R', —OCONR'R" or —CR'=NOR"; and R' and R" independently represent hydrogen, C1-C8 alkyl, C2-C8 alkenyl or C2-C8 alkynyl.

DETAILED DESCRIPTION OF THE INVENTION

As used herein, a C1-C8 alkyl group or moiety can be linear, branched or cyclic but is preferably linear. It is preferably a C1-C6 alkyl group, more preferably a C1-C4 alkyl group, most preferably a C1-C3 alkyl group. Suitable such alkyl groups and moieties include methyl, ethyl, n-propyl, i-propyl, n-butyl, sec-butyl and tert-butyl, as well as pentyl, hexyl, heptyl and octyl and isomers thereof.

As used herein, a C2-C8 alkenyl group or moiety can be linear, branched or cyclic but is preferably linear. It contains one or more carbon-carbon double bonds. It is preferably a C2-C6 alkenyl group, more preferably a C2-C4 alkenyl group, most preferably a C2-C3 alkyl group. Suitable such alkenyl groups and moieties include vinyl, allyl, propenyl, butenyl, pentenyl, hexenyl, heptenyl and octenyl and isomers thereof.

As used herein, a C2-C8 alkynyl group or moiety can be linear, branched or cyclic but is preferably linear. It contains one or more carbon-carbon triple bonds. It is preferably a C2-C6 alkynyl group, more preferably a C2-C4 alkynyl group, most preferably a C2-C3 alkynyl group. Suitable such alkynyl groups and moieties include ethynyl, propynyl, butynyl, pentynyl, hexynyl, heptynyl and octynyl and isomers thereof.

An alkyl, alkenyl or alkynyl group or moiety can be substituted or unsubstituted. Typically, it carries up to three substituents, e.g. one or two substituents. Suitable substituents include halogen such as fluorine, hydroxy, amino, (C1-C4 alkyl)amino, di(C1-C4 alkyl)amino, C1-C4 alkoxy such as methoxy or ethoxy, —CO₂H and —CO₂(C1-C4 alkyl). Examples of these substituents include halogen such as fluorine, hydroxy, amino, (C1-C4 alkyl)amino, di(C1-C4 alkyl)amino and C1-C4 alkoxy such as methoxy or ethoxy.

As used herein, a C3-C6 cycloalkyl group is typically a C5 or C6 cycloalkyl group. Typically a cycloalkyl group is unsubstituted or substituted with up to three substituents, e.g. one or two substituents. Suitable substituents include C1-C8 alkyl, C2-C8 alkenyl, C2-C8 alkynyl, Z and —Y—Z wherein Y and Z are as hereinbefore defined. Typically, a cycloalkyl group is unsubstituted.

When any of R1 to R6 or R8 is (C1-C4 alkylene)-aryl or (C1-C4 alkylene)-heterocyclyl, the C1-C4 alkylene moiety is preferably methylene, ethylene, n-propylene or i-propylene, each of which is unsubstituted or substituted with one or two, e.g. one substituent selected from halogen, hydroxyl, amino, (C1-C4 alkyl)amino, di(C1-C4 alkyl)amino, C1-C4 alkoxy, —CO₂H and —CO₂(C1-C4 alkyl). In one embodiment, the C1-C4 alkylene moiety is methylene.

When R1 or R8 is —(C2-C4 alkenylene)-aryl or —(C2-C4 alkenylene)-heterocyclyl, the C2-C4 alkenylene moiety is preferably ethenylene.

When Y is C1-C8 alkylene, it is preferably C1-C4 alkylene, more preferably methylene or ethylene.

When Y is C2-C8 alkenylene, it is preferably C2-C4 alkenylene, more preferably ethenylene.

When Y is C2-C8 alkynylene, it is preferably C2-C4 alkynylene, more preferably ethynylene.

When R' or R" is C1-C8 alkyl, it is preferably C1-C4 alkyl, more preferably methyl or ethyl.

When R' or R" is C2-C8 alkenyl, it is preferably C2-C4 alkenyl, more preferably ethenyl.

When R' or R" is C2-C8 alkynyl, it is preferably C2-C4 alkynyl, more preferably ethynyl.

As used herein, an aryl group or moiety is typically phenyl or naphthyl.

As used herein, a heterocyclyl group or moiety is a saturated or unsaturated, 5- to 12-membered ring system in which the ring contains at least one heteroatom. Typically, the ring contains up to three or four heteroatoms, e.g. one or two heteroatoms, selected from O, S and N. Thus, a heterocyclyl group or moiety is typically a 5- to 12-membered ring containing one, two or three heteroatoms selected from O, S and N. Suitable such heterocyclyl groups and moieties include, for example, monocyclic saturated 5- to 8-membered rings such as tetrahydrofuranyl, piperidinyl, morpholinyl, thiomorpholinyl, pyrrolidinyl, dioxolanyl, piperidonyl, azepanyl, piperazinyl and tetrahydropyranyl, e.g. piperidinyl; monocyclic unsaturated 5- to 8-membered rings such as furanyl, pyrrolyl, thiophenyl, oxazolyl, isoxazolyl, thiazolyl, pyrazolyl, imidazolyl, triazolyl, tetrazolyl, pyridinyl, pyrimidinyl, pyrazinyl, pyridazinyl and di- and tetrahydropyridinyl, e.g. furanyl, thiophenyl or pyridinyl; bicyclic 8- to 10-membered ring systems such as indolyl, benzofuranyl, benzothiophenyl, benzimidazolyl, benzoxazolyl, benzopyrazolyl, benzothiazolyl, benzotriazolyl, quinolinyl, quinazolinyl, quinoxalinyl, cinnolinyl, purinyl and cyclopentapyridines which may optionally be partially unsaturated; and tricyclic 11- or 12-membered ring systems such as acridinyl, pteridinyl and benzathiazinyl. Particular examples of such heterocyclyl groups and moieties include monocyclic saturated 5- to 8-membered rings such as tetrahydrofuranyl, piperidinyl, morpholinyl, azepanyl, piperazinyl and tetrahydropyranyl, e.g. piperidinyl; monocyclic unsaturated 5- to 8-membered rings such as furanyl, pyrrolyl, thiophenyl, oxazolyl, isoxazolyl, thiazolyl, pyrazolyl, imidazolyl, triazolyl, tetrazolyl, pyridinyl, pyrimidinyl, pyrazinyl, pyridazinyl and di- and tetrahydropyridinyl, e.g. furanyl, thiophenyl or pyridinyl; bicyclic 8- to 10-membered ring systems such as indolyl, dihydroindolyl, benzofuranyl, benzothiophenyl, benzimidazolyl, benzoxazolyl, benzopyrazolyl, benzothiazolyl, benzotriazolyl, quinolinyl, quinazolinyl, quinoxalinyl, cinnolinyl, purinyl and cyclopentapyridines which may optionally be partially unsaturated; and tricyclic 11- or 12-membered ring systems such as acridinyl, pteridinyl and benzathiazinyl.

A heterocyclyl or aryl group or moiety may be substituted or unsubstituted. Each ring atom may be unsubstituted or may carry one or two substituents. If desired, a nitrogen atom may be disubstituted and a sulphur atom may be substituted, providing a charged heteroatom. Typically, a heterocyclyl or aryl group or moiety carries up to three substituents, e.g. one or two substituents. The heterocycle may be connected to the remainder of the molecule by a bond to any of its available ring positions.

Suitable substituents include C1-C8 alkyl, C2-C8 alkenyl, C2-C8 alkynyl, unsubstituted phenyl, Z and —Y—Z wherein Y and Z are as hereinbefore defined. Preferred substituents on an aryl or heterocyclyl group or moiety are unsubstituted substituents selected from halogen, —CO$_2$R', —CONR'R", OCOR', hydroxyl, cyano, —NR'R", —COR', —NSO$_2$R', —O(C2-C4 alkenyl), C2-C4 alkenyl, —SO$_2$R', —OCONR'R" and —CR'=NOR", or C1-C4 alkyl or C1-C4 alkoxy groups which are unsubstituted or substituted with one, two, three or four, for example one, two, or three, for example one, unsubstituted group selected from halogen, hydroxyl, amino, (C1-C4 alkyl)amino, di(C1-C4 alkyl)amino, C1-C4 alkoxy, cyano, —COR' and —CO$_2$R', wherein R' and R" are independently selected from hydrogen and C1-C4 alkyl. The substituents on such an alkyl or alkoxy substituent are in one aspect of the invention selected from halogen, hydroxyl, amino, (C1-C4 alkyl)amino, di(C1-C4 alkyl)amino, C1-C4 alkoxy, cyano and —CO$_2$R', wherein R' and R" are independently selected from hydrogen and C1-C4 alkyl.

Examples of substituents on an aryl or heterocyclyl group or moiety are unsubstituted substituents selected from halogen, C1-C4 alkyl, C1-C4 alkoxy, —CO$_2$R', —CONR'R", —OCOR', hydroxyl, cyano and phenyl, in particular halogen, C1-C4 alkyl, C1-C4 alkoxy, —CO$_2$R', —CONR'R", —OCOR' and cyano wherein R' and R" are independently selected from hydrogen and C1-C4 alkyl.

Typically none or one cyano substituent is present. Typically none, one or two, e.g. none or one phenyl substituent is present.

As used herein, a halogen is typically chlorine, fluorine, bromine or iodine, and is preferably chlorine, fluorine or bromine.

In one embodiment of the invention, X is —NR8-, —O— or —S—, preferably —NR8- or —O—, most preferably —NR8—.

In one embodiment of the invention, $X^1$ is O or NOR9, wherein R9 is hydrogen or C1-C4 alkyl which is unsubstituted or substituted with one, two or three substituents selected from halogen, hydroxyl, amino, (C1-C4 alkyl)amino, di(C1-C4 alkyl)amino, C1-C4 alkoxy, —CO$_2$H and —CO$_2$(C1-C4 alkyl). Preferably, R9 is a linear C1-C4 alkyl group which is unsubstituted or substituted with a single substituent on the terminal carbon atom. Preferred substituents are di(C1-C4 alkyl)amino and —CO$_2$H. In another embodiment, $X^1$ is O.

In one embodiment of the invention, R1 is other than hydrogen, thiazolyl or 4-hydroxy-phenyl. In another embodiment, R1 is other than pyridyl, in particular other than methoxy-pyridyl, e.g. 6-methoxy-pyridyl. In another embodiment, R1 is phenyl, a monocyclic, unsaturated 5- to 8-membered heterocyclyl ring containing one heteroatom, C5-C6 cycloalkyl, (unsubstituted C1-C2 alkylene)-phenyl, or C1-C4 alkyl.

In a preferred embodiment, R1 is phenyl, a 5- to 12-membered heterocyclyl group, C5-C6 cycloalkyl, C1-C4 alkyl, -A1-L1-A2 or -L2-A wherein A1 is phenyl, L1 is a bond, —NR'— or —CONR'R"—, wherein R' and R" are independently selected from hydrogen and C1-C4 alkyl groups and moieties, L2 is C1-C4 alkylene which is unsubstituted or substituted with one or two substituents selected from halogen, C1-C4 alkoxy and —CO$_2$(C1-C4 alkyl) and A2 is phenyl or a 5- to 6-membered heterocyclyl group containing one, two, three or four heteroatoms selected from N, O and S.

The phenyl and heterocyclyl groups or moieties R1, A1 and A2 are typically unsubstituted or substituted with one, two or three substituents selected from the unsubstituted groups halogen, —CO$_2$R', —CONR'R", OCOR', hydroxyl, cyano, —NR'R", —COR', —NSO$_2$R', —O(C2-C4 alkenyl), C2-C4 alkenyl, —SO$_2$R', —OCONR'R" and —CR'=NOR", and from C1-C4 alkyl and C1-C4 alkoxy groups which are unsubstituted or substituted with one, two, three or four, for example one, two or three, for example one, unsubstituted group selected from halogen, hydroxyl, amino, (C1-C4 alkyl)amino, di(C1-C4 alkyl)amino, C1-C4 alkoxy, cyano, —COR' and —CO$_2$R', wherein R' and R" are independently selected from hydrogen and C1-C4 alkyl. Preferably, the substituents on the phenyl and heterocyclyl groups or moieties R1, A1 and A2 are selected from the unsubstituted groups halogen, —CO$_2$R', —CONR'R", —OCOR', hydroxyl, cyano, —NR'R", —COR', —NSO$_2$R', —O(C2-C4 alkenyl), C2-C4 alkenyl, —SO$_2$R', —OCONR'R", —CR'=NOR" and —CF$_3$, and from C1-C4 alkyl and C1-C4 alkoxy groups which are unsubstituted or substituted with from one to four, for example one unsubstituted group selected from halogen, hydroxyl, di(C1-C4 alkyl)amino, cyano, —COR' and —CO$_2$R', wherein R' and R" are independently selected from hydrogen and C1-C4 alkyl. In one aspect of the invention the alkyl and alkoxy substituents on the phenyl and heterocyclyl groups or moieties R1, A1 and A2 optionally bear substituent(s) selected from halogen, hydroxyl, amino, (C1-C4 alkyl)amino, di(C1-C4 alkyl)amino, C1-C4 alkoxy, cyano and —CO$_2$R', for example from hydroxyl, di(C1-C4 alkyl)amino, cyano and —CO$_2$R', wherein R' and R" are independently selected from hydrogen and C1-C4 alkyl.

Preferably the group A1 is unsubstituted phenyl, or phenyl substituted with a group —NR'R", wherein R' and R" are independently hydrogen or C1-C4 alkyl. In one embodiment A1 is unsubstituted phenyl. Preferred substituents on the group A2 are C1-C4 alkyl and —CO₂(C1-C4 alkyl).

In another embodiment, the phenyl and heterocyclyl groups or moieties R1 are typically unsubstituted or substituted with one, two or three unsubstituted groups selected from halogen, C1-C4 alkyl, C1-C4 alkoxy, —CO₂R', —CONR'R", OCOR', hydroxyl, cyano and phenyl, wherein R' and R" are independently selected from hydrogen and C1-C4 alkyl. In this embodiment, the substituents on the phenyl and heterocyclyl groups or moieties are preferably unsubstituted groups selected from halogen, C1-C4 alkyl, C1-C4 alkoxy, —CO₂R', —CONR'R", —OCOR' and cyano, wherein R' and R" are independently selected from hydrogen and C1-C4 alkyl.

The cycloalkyl and alkyl groups and moieties R1 are typically unsubstituted or substituted with one or two unsubstituted groups selected from C1-C4 alkoxy, halogen, hydroxyl, amino, (C1-C4 alkyl)amino, di(C1-C4 alkyl)amino or CO₂ (C1-C4 alkyl), for example C1-C4 alkoxy, halogen, hydroxyl, amino, (C1-C4 alkyl)amino or di(C1-C4 alkyl)amino.

In a preferred embodiment of the invention, R1 is phenyl, pyridinyl, thiophenyl, furanyl, benzimidazolyl, indolyl, dihydroindolyl, unsubstituted C5-C6 cycloalkyl, C1-C4 alkyl which is unsubstituted or substituted with C1-C4 alkoxy or —CO₂(C1-C4 alkyl), -A1-L1-A2 or -L2-A2, wherein A1 is unsubstituted phenyl or phenyl substituted with a group —NR'R" (e.g. A1 is unsubstituted phenyl), L1 is a bond, —NH— or —CONR'R"—, wherein R' and R" are individually selected from hydrogen and C1-C4 alkyl groups and moieties, L2 is C1-C4 alkylene which is unsubstituted or substituted with one or two substituents selected from halogen, C1-C4 alkoxy and —CO₂(C1-C4 alkyl), and A2 is phenyl or a 5- to 6-membered heterocyclyl group containing one, two, three or four heteroatoms selected from N, O and S. In this embodiment, the aryl and heterocyclyl groups R1 and A2 are unsubstituted or substituted with one, two or three substituents selected from the unsubstituted groups halogen, —CO₂R', —CONR'R", OCOR', hydroxyl, cyano, —NR'R", —COR', —NSO₂R', —O(C2-C4 alkenyl), C2-C4 alkenyl, —SO₂R', —OCONR'R", —CR'=NOR" and CF₃, and from C1-C4 alkyl and C1-C4 alkoxy groups which are unsubstituted or substituted with from one to four e.g. one unsubstituted group selected from halogen, hydroxyl, di(C1-C4 alkyl) amino, cyano, —COR' and —CO₂R' (for example selected from hydroxyl, di(C1-C4 alkyl)amino, cyano and —CO₂R'), wherein R' and R" are independently selected from hydrogen and C1-C4 alkyl. Typically only one cyano substituent is present.

In another embodiment of the invention, R1 is phenyl, pyridinyl, thiophenyl, furanyl, unsubstituted C5-C6 cycloalkyl, benzyl or C1-C4 alkyl which is unsubstituted or substituted with C1-C4 alkoxy. In this embodiment the phenyl, pyridinyl, thiophenyl, furanyl and benzyl groups are unsubstituted or substituted with one or two unsubstituted substituents selected from halogen, C1-C4 alkyl, C1-C4 alkoxy, —CO₂R', —CONR'R", —OCOR' and cyano, wherein R' and R" are independently selected from hydrogen and C1-C4 alkyl. Typically only one cyano substituent is present.

In another embodiment, when X is —NR8- and R8 is hydrogen or methyl, R1 is phenyl, phenol, benzoic acid methyl ester, pyridyl, dimethoxyphenyl, benzoic acid-butyl ester, dimethoxyphenyl, cyanophenyl, methoxypyridyl, thienyl carboxylic acid-methylester, N,N-dimethylbenzamide, N-methylbenzamide, benzamide, cyclohexyl, isopropyl, methyl, methoxyethyl or tolyl.

Typically R8 is hydrogen, C1-C8 alkyl, C2-C8 alkenyl or C2-C8 alkynyl, preferably hydrogen or unsubstituted C1-C4 alkyl. Alternatively, when X is NR8, R1 and R8 together form a 5- to 12-membered heterocyclyl group, e.g. a monocyclic, saturated, 5- to 8-membered heterocyclyl ring, which is typically unsubstituted. The heterocyclyl group is typically piperidinyl, morpholinyl, azepanyl or dihydroindolyl e.g. piperidinyl, morpholinyl or azepanyl, preferably piperidinyl.

Typically, R2 is phenyl, a monocyclic, unsaturated 5- to 8-membered heterocyclyl ring or unsubstituted C1-C8 alkyl. The phenyl and heterocyclyl groups are unsubstituted or substituted with one, two or three unsubstituted substituents selected from halogen, C1-C4 alkyl, C1-C4 alkoxy, —CO₂R', —CONR'R", —OCOR' or cyano, wherein R' and R" are independently selected from hydrogen and C1-C4 alkyl. Typically only one cyano substituent is present.

In another embodiment, R2 is unsubstituted or substituted phenyl, unsubstituted or substituted pyridinyl or unsubstituted thiophenyl or furanyl, the substituents being selected from halogen, unsubstituted C1-C4 alkyl, unsubstituted C1-C4 alkoxy or cyano, e.g. halogen, unsubstituted C1-C4 alkyl or unsubstituted C1-C4 alkoxy. In this embodiment R2 is, for example, unsubstituted or substituted phenyl or unsubstituted pyridinyl, thiophenyl or furanyl.

In one embodiment, when R1 is 6-methoxy-pyridinyl, R2 is not pyridyl. In this embodiment, typically when R1 is methoxy-pyridyl, R2 is unsubstituted or substituted phenyl or unsubstituted thiophenyl or furanyl, the substituents being selected from halogen, unsubstituted C1-C4 alkyl or unsubstituted C1-C4 alkoxy. For example, when R1 is pyridyl, R2 may be unsubstituted or substituted phenyl or unsubstituted thiophenyl or furanyl, the substituents being selected from halogen, unsubstituted C1-C4 alkyl or unsubstituted C1-C4 alkoxy.

Typically, when R3, R4, R5 or R6 is aryl, heterocyclyl, —(C1-C4 alkylene)-aryl or (C1-C4 alkylene)-heteroaryl, it is phenyl, benzyl or pyridyl. Typically, none, one or two, preferably none or one, of R3, R4, R5 and R6 is aryl, heterocyclyl, —(C1-C4 alkylene)-aryl or (C1-C4 alkylene)-heterocyclyl. Preferably, no more than one of R3, R4, R5, R6 and R7 is NO₂, and no more than one of R3, R4, R5 and R6 and R7 is CN. R3, R4, R5 and R6 are typically unsubstituted.

In one embodiment, R3, R4, R5 and R6 independently represent phenyl, benzyl, pyridyl, hydrogen, halogen, C1-C8 alkyl, C2-C8 alkenyl, C2-C8 alkynyl, —OR', —CO₂R', CONR'R", —COR', —CN, —NO₂, —NR'R" or —CF₃ wherein R' and R" are independently hydrogen or C1-C4 alkyl and wherein only one or two of R3, R4, R5 and R6 is selected from phenyl, benzyl and pyridyl.

In another embodiment, R3, R4, R5 and R6 independently represent hydrogen, halogen, C1-C8 alkyl, C2-C8 alkenyl, C2-C8 alkynyl, —OR', —CO₂R', CONR'R", —COR', —CN, —NO₂, —NR'R" or —CF₃ wherein R' and R" are independently hydrogen or C1-C4 alkyl. In yet another embodiment, R3, R4, R5 and R6 independently represent hydrogen, halogen, C1-C4 alkyl, or C1-C4 alkoxy, e.g. hydrogen, halogen or C1-C4 alkyl, preferably hydrogen.

Typically, R7 represents hydrogen, halogen, C1-C4 alkyl, C2-C4 alkenyl, C2-C4 alkynyl, —OR', —CO₂R', CONR'R", —COR', —CN, —NO₂, —NR'R" or —CF₃ wherein R' and R" are independently hydrogen or C1-C4 alkyl. In another embodiment R7 represents hydrogen, halogen or C1-C4 alkyl, preferably hydrogen. R7 is typically unsubstituted.

Typically, Z is halogen, OR', SR', —NR'R', —CO₂R', —CONR'R", —COR', —OCOR' or CN, wherein R' and R" are independently hydrogen or C1-C4 alkyl.

In one embodiment of the invention, the indolizinyl derivative is not

N-(6-Methoxy-pyridin-3-yl)-2-oxo-2-(2-pyridin-4-yl-indolizin-3-yl)-acetamide
N-(6-Methoxy-pyridin-3-yl)-2-oxo-2-(2-pyridin-3-yl-indolizin-3-yl)-acetamide
N-(6-Methoxy-pyridin-3-yl)-2-oxo-2-(2-pyridin-2-yl-indolizin-3-yl)-acetamide
Oxo-(2-phenyl-indolizin-3-yl)-thioacetic acid S-(2-methoxy-phenyl) ester
N-(4-Hydroxy-phenyl)-2-oxo-2-(2-phenyl-indolizin-3-yl)-acetamide
(2-Methyl-indolizin-3-yl)-oxo-acetic acid,
2-Oxo-2-(2-phenyl-indolizin-3-yl)-N-thiazol-2-yl-acetamide,
N-Cyclohexyl-2-oxo-2-(2-pyridin-3-yl-indolizin-3-yl)-acetamide
N-Methyl-2-oxo-2-(2-pyridin-3-yl-indolizin-3-yl)-acetamide
N-Isopropyl-2-oxo-2-(2-pyridin-3-yl-indolizin-3-yl)-acetamide
N-Benzyl-2-oxo-2-(2-pyridin-3-yl-indolizin-3-yl)-acetamide
1-Piperidin-1-yl-2-(2-pyridin-3-yl-indolizin-3-yl)-ethane-1,2-dione
N,N-Dimethyl-2-oxo-2-(2-pyridin-3-yl-indolizin-3-yl)-acetamide
2-(8-Methyl-2-phenyl-indolizin-3-yl)-2-oxo-N-p-tolyl-acetamide
2-(8-Methoxy-2-phenyl-indolizin-3-yl)-2-oxo-N-p-tolyl-acetamide
2-(8-Methoxy-2-phenyl-indolizin-3-yl)-N-(6-methoxy-pyridin-3-yl)-2-oxo-acetamide
2-(7-Methyl-2-pyridin-3-yl-indolizin-3-yl)-2-oxo-N-p-tolyl-acetamide
N-(6-Methoxy-pyridin-3-yl)-2-(6-methyl-2-pyridin-3-yl-indolizin-3-yl)-2-oxo-acetamide
N-(6-Methoxy-pyridin-3-yl)-2-(7-methyl-2-pyridin-3-yl-indolizin-3-yl)-2-oxo-acetamide
2-(7-Methoxy-2-phenyl-indolizin-3-yl)-2-oxo-N-p-tolyl-acetamide
N-(4-Acetylamino-phenyl)-2-oxo-2-(2-phenyl-indolizin-3-yl)-acetamide
2-Oxo-2-(2-phenyl-indolizin-3-yl)-N-(4-sulfamoyl-phenyl)-acetamide
1-(2,3-Dihydro-indol-1-yl)-2-(2-pyridin-3-yl-indolizin-3-yl)-ethane-1,2-dione
N-(4-Acetylamino-phenyl)-2-oxo-2-(2-pyridin-3-yl-indolizin-3-yl)-acetamide
N-(4-Methanesulfonylamino-phenyl)-2-oxo-2-(2-pyridin-3-yl-indolizin-3-yl)-acetamide
2-[2-Oxo-2-(2-pyridin-3-yl-indolizin-3-yl)-acetylamino]-benzoic acid ethyl ester
N-(2,6-Dichloro-phenyl)-2-oxo-2-(2-pyridin-3-yl-indolizin-3-yl)-acetamide
2-Oxo-2-(2-pyridin-3-yl-indolizin-3-yl)-N-(4-sulfamoyl-phenyl)-acetamide
N-(3-Hydroxy-phenyl)-2-oxo-2-(2-phenyl-indolizin-3-yl)-acetamide
N-(2,6-Dichloro-phenyl)-2-oxo-2-(2-phenyl-indolizin-3-yl)-acetamide
N-(4-Methoxy-phenyl)-2-(8-methoxy-2-phenyl-indolizin-3-yl)-2-oxo-acetamide
N-(4-Methoxy-phenyl)-2-(7-methoxy-2-phenyl-indolizin-3-yl)-2-oxo-acetamide
N-[3-(3-Dimethylamino-propoxy)-phenyl]-2-oxo-2-(2-phenyl-indolizin-3-yl)-acetamide
N-(4-Acetyl-phenyl)-2-(6-methoxy-2-phenyl-indolizin-3-yl)-2-oxo-acetamide
4-{3-[2-Oxo-2-(2-phenyl-indolizin-3-yl)-acetylamino]-phenoxy}-butyric acid
N-(2-Mercapto-phenyl)-2-oxo-2-(2-phenyl-indolizin-3-yl)-acetamide
N-(4-Methanesulfonyl-phenyl)-2-oxo-2-(2-pyridin-3-yl-indolizin-3-yl)-acetamide
N-(3-Methyl-3H-benzoimidazol-5-yl)-2-oxo-2-(2-pyridin-3-yl-indolizin-3-yl)-acetamide
2-Oxo-N-(2-oxo-2,3-dihydro-1H-indol-5-yl)-2-(2-phenyl-indolizin-3-yl)-acetamide
Diethyl-carbamic acid 2-[2-oxo-2-(2-phenyl-indolizin-3-yl)-acetylamino]-phenyl ester
2-(6-Cyano-2-phenyl-indolizin-3-yl)-N-(4-methoxy-phenyl)-2-oxo-acetamide
2-Methoxy-5-[2-oxo-2-(2-phenyl-indolizin-3-yl)-acetylamino]-benzoic acid
N-(4-Methanesulfonylaminocarbonyl-phenyl)-2-oxo-2-(2-phenyl-indolizin-3-yl)-acetamide,
2-(6-Acetyl-2-phenyl-indolizin-3-yl)-N-(4-methoxy-phenyl)-2-oxo-acetamide or
N-[6-(2-Diethylaminomethyl-pyrrolidin-1-yl)-pyridin-3-yl]-2-oxo-2-(2-phenyl-indolizin-3-yl)-acetamide.

In one embodiment of the invention, the indolizinyl derivative is a derivative of formula (I) in which:

X is —NR8- or —O—;
$X^1$ is O or NOR9, wherein R9 is hydrogen or C1-C4 alkyl which is unsubstituted or substituted with one, two or three substituents selected from halogen, hydroxyl, amino, (C1-C4 alkyl)amino, di(C1-C4 alkyl)amino, C1-C4 alkoxy, —$CO_2$H and —$CO_2$(C1-C4 alkyl);
R1 is phenyl, a 5- to 12-membered heterocyclyl group, C5-C6 cycloalkyl, C1-C4 alkyl, -A1-L1-A2 or -L2-A2;
A1 is phenyl;
L1 is a bond, —NR'— or —CONR'R"—, wherein R' and R" are independently selected from hydrogen and C1-C4 alkyl groups and moieties;
L2 is C1-C4 alkylene which is unsubstituted or substituted with one or two substituents selected from halogen, C1-C4 alkoxy and —$CO_2$(C1-C4 alkyl);
A2 is phenyl or a 5- to 6-membered heterocyclyl group containing one, two, three or four heteroatoms selected from N, O and S;
R8 is hydrogen, C1-C8 alkyl, C2-C8 alkenyl or C2-C8 alkynyl;
or when X is NR8, R1 and R8 may together form a 5- to 12-membered heterocyclyl ring;
R2 is phenyl, a monocyclic, unsaturated 5- to 8-membered heterocyclyl ring or unsubstituted C1-C8 alkyl, wherein the phenyl and heterocyclyl groups are unsubstituted or substituted with one, two or three unsubstituted groups selected from halogen, C1-C4 alkyl, C1-C4 alkoxy, —$CO_2$R', —CONR'R", —OCOR' and cyano, wherein R' and R" are independently selected from hydrogen and C1-C4 alkyl;
R3, R4, R5 and R6 represent phenyl, benzyl, pyridyl, hydrogen, halogen, C1-C8 alkyl, C2-C8 alkenyl, C2-C8 alkynyl, —OR', —$CO_2$R', CONR'R", —COR', —CN, —$NO_2$, —NR'R" or —$CF_3$ wherein R' and R" are independently hydrogen or C1-C4 alkyl; and R7 represents hydrogen, halogen, C1-C4 alkyl, C2-C4 alkenyl, C2-C4 alkynyl, —OR', —CO2R', CONR'R", —COR', —CN, —NO2, —NR'R" or —CF3 wherein R' and R" are independently hydrogen or C1-C4 alkyl;
wherein the alkyl and cycloalkyl groups R1 are unsubstituted or substituted with one or two unsubstituted groups selected from C1-C4 alkoxy, halogen, hydroxyl, amino, (C1-C4 alkyl)amino, di(C1-C4 alkyl)amino or CO2(C1-C4 alkyl); and the phenyl and heterocyclyl groups or moieties R1, A1 and A2 are unsubstituted or substituted with one, two or three substituents selected from the unsubstituted groups halogen, —CO$_2$R', —CONR'R", OCOR', hydroxyl, cyano, —NR'R", —COR', —NSO$_2$R', —O(C2-C4 alkenyl), C2-C4 alkenyl, —SO$_2$R', —OCONR'R" and —CR'=NOR", and from C1-C4 alkyl and C1-C4 alkoxy groups which are unsubstituted or substituted with from one to four, e.g. one, two or three, for example one, unsubstituted group selected from halogen, hydroxyl, amino, (C1-C4 alkyl)amino, di(C1-C4 alkyl)amino, C1-C4 alkoxy, cyano, —COR' and —CO$_2$R' (for example selected from halogen, hydroxyl, amino, (C1-C4 alkyl)amino, di(C1-C4 alkyl)amino, C1-C4 alkoxy, cyano and —CO$_2$R'), wherein R' and R" are independently selected from hydrogen and C1-C4 alkyl.

In another embodiment of the invention,

X is —NR8- or —O—;

$X^1$ is O or NOR9, wherein R9 is a linear C1-C4 alkyl group which is unsubstituted or substituted with a single substituent on the terminal carbon atom, the substituent being selected from di(C1-C4 alkyl)amino and —CO$_2$H;

R1 is phenyl, pyridinyl, thiophenyl, furanyl, benzimidazolyl, indolyl, dihydroindolyl, unsubstituted C5-C6 cycloalkyl, C1-C4 alkyl which is unsubstituted or substituted with C1-C4 alkoxy or —CO$_2$(C1-C4 alkyl), -A1-L1-A2 or -L2-A2, wherein the aryl and heterocyclyl groups are unsubstituted or substituted with one, two or three substituents selected from the unsubstituted groups halogen, —CO$_2$R', —CONR'R", OCOR', hydroxyl, cyano, —NR'R", —COR', —NSO$_2$R', —O(C2-C4 alkenyl), C2-C4 alkenyl, —SO$_2$R', —OCONR'R", —CR'=NOR" and CF$_3$, and from C1-C4 alkyl and C1-C4 alkoxy groups which are unsubstituted or substituted with from one to four unsubstituted groups selected from halogen, hydroxyl, di(C1-C4 alkyl)amino, cyano, —COR' and —CO$_2$R', wherein R' and R" are independently selected from hydrogen and C1-C4 alkyl;

A1 is unsubstituted phenyl or phenyl substituted with a group —NR'R", wherein R' and R" are independently selected from hydrogen and C1-C4 alkyl;

L1 is a bond, —NH— or —CONR'R"—, wherein R' and R" are independently selected from hydrogen and C1-C4 alkyl groups and moieties;

L2 is C1-C4 alkylene which is unsubstituted or substituted with one or two substituents selected from halogen, C1-C4 alkoxy and —CO$_2$(C1-C4 alkyl);

A2 is phenyl or a 5- to 6-membered heterocyclyl group containing one, two, three or four heteroatoms selected from N, O and S, wherein the heterocycle is unsubstituted or substituted with one or two substituents selected from C1-C4 alkyl and CO$_2$(C1-C4 alkyl);

R8 is hydrogen or unsubstituted C1-C4 alkyl; or when X is NR8, R1 and R8 together with the nitrogen atom to which they are attached may form a 5- to 12-membered heterocyclyl group preferably selected from piperidinyl, morpholinyl, azepanyl or dihydroindolyl;

R2 is unsubstituted or substituted phenyl, unsubstituted or substituted pyridinyl, or unsubstituted thiophenyl or furanyl, the substituents being selected from halogen, unsubstituted C1-C4 alkyl, unsubstituted C1-C4 alkoxy and cyano;

R3 to R6 are independently selected from hydrogen, unsubstituted C1-C4 alkyl and unsubstituted C1-C4 alkoxy; and R7 is hydrogen.

In one aspect of this embodiment, R1 is phenyl, pyridinyl, thiophenyl, furanyl, benzimidazolyl, indolyl, dihydroindolyl, unsubstituted C5-C6 cycloalkyl, C1-C4 alkyl which is unsubstituted or substituted with C1-C4 alkoxy or —CO$_2$(C1-C4 alkyl), -A1-L1-A2 or -L2-A2, wherein the aryl and heterocyclyl groups are unsubstituted or substituted with one, two or three substituents selected from the unsubstituted groups halogen, —CO$_2$R', —CONR'R", OCOR', hydroxyl, cyano, —NR'R", —COR', —NSO$_2$R', —O(C2-C4 alkenyl), C2-C4 alkenyl, —SO$_2$R', —OCONR'R", —CR'=NOR" and CF$_3$, and from C1-C4 alkyl and C1-C4 alkoxy groups which are unsubstituted or substituted with one unsubstituted group selected from hydroxyl, di(C1-C4 alkyl)amino, cyano and —CO$_2$R', wherein R' and R" are independently selected from hydrogen and C1-C4 alkyl;

A1 is unsubstituted phenyl;

A2 is phenyl or a 5- to 6-membered heterocyclyl group containing one, two, three or four heteroatoms selected from N, O and S, wherein the heterocycle is unsubstituted or substituted with a C1-C4 alkyl or CO$_2$(C1-C4 alkyl) group;

R2 is unsubstituted or substituted phenyl or unsubstituted pyridinyl, thiophenyl or furanyl, the substituents being selected from halogen, unsubstituted C1-C4 alkyl, unsubstituted C1-C4 alkoxy and cyano; and X, X', L1, L2, and R3 to R8 are as defined above.

In another embodiment of the invention, the indolizinyl derivative is a derivative of formula (I) in which:

X is —NR8- or —O—;

$X^1$ is O;

R1 is phenyl, a monocyclic, unsaturated 5- to 8-membered heterocyclyl ring containing one heteroatom, C5-C6 cycloalkyl, (unsubstituted C1-C2 alkylene)-phenyl, or C1-C4 alkyl, wherein the phenyl and heterocyclyl groups are unsubstituted or substituted with one, two or three unsubstituted groups selected from halogen, C1-C4 alkyl, C1-C4 alkoxy, —CO$_2$R', —CONR'R", —OCOR' and cyano, wherein R' and R" are independently selected from hydrogen and C1-C4 alkyl, and wherein the cycloalkyl and alkyl groups are unsubstituted or substituted with one or two unsubstituted groups selected from C1-C4 alkoxy, halogen, hydroxyl, amino, (C1-C4 alkyl)amino or di(C1-C4 alkyl)amino;

R2 is as defined above with the proviso that when R1 is 6-methoxy pyridinyl, R2 is not pyridinyl; and R3, R4, R5, R6, R7 and R8 are as defined above.

In another embodiment of the invention,

X is —NR8- or —O—;

$X^1$ is O;

R1 is phenyl, a monocyclic, unsaturated 5- to 8-membered heterocyclyl ring containing one heteroatom, C5-C6 cycloalkyl, (unsubstituted C1-C2 alkylene)-phenyl, or C1-C4 alkyl which is unsubstituted or substituted with C1-C4 alkoxy;

R8 is hydrogen, C1-C8 alkyl, C2-C8 alkenyl or C2-C8 alkynyl;

or when X is NR8, R1 and R8 may together form an unsubstituted, monocyclic, saturated, 5- to 8-membered heterocyclyl ring;

R2 is phenyl, a monocyclic, unsaturated 5- to 8-membered heterocyclyl ring or unsubstituted C1-C8 alkyl;

R3, R4, R5 and R6 represent phenyl, benzyl, pyridyl, hydrogen, halogen, C1-C8 alkyl, C2-C8 alkenyl, C2-C8 alkynyl, —OR', —CO$_2$R', CONR'R", —COR', —CN, —NO$_2$, —NR'R" or —CF$_3$ wherein R' and R" are independently hydrogen or C1-C4 alkyl; and R7 represents hydrogen, halogen, C1-C4 alkyl, C2-C4 alkenyl, C2-C4 alkynyl, —OR', —CO$_2$R', CONR'R", —COR', —CN, —NO₂, —NR'R" or —CF₃ wherein R' and R" are independently hydrogen or C1-C4 alkyl;

wherein the phenyl and heterocyclyl groups or moieties of R1 and R2 are unsubstituted or substituted with one, two or three unsubstituted groups selected from halogen, C1-C4 alkyl, C1-C4 alkoxy, —CO₂R', —CONR'R", —OCOR' and cyano, wherein R' and R" are independently selected from hydrogen and C1-C4 alkyl.

In yet another embodiment of the invention, the indolizinyl derivative is of formula (IA):

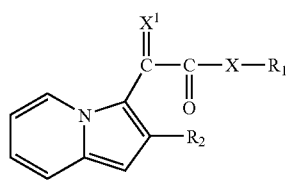

(IA)

wherein:

X is —NR8- or —O—; preferably —NR8-;

R1 is phenyl, pyridinyl, thiophenyl, furanyl, unsubstituted C5-C6 cycloalkyl, benzyl or C1-C4 alkyl which is unsubstituted or substituted with C1-C4 alkoxy, wherein the phenyl, pyridinyl, thiophenyl, furanyl or benzyl groups are unsubstituted or substituted with one or two unsubstituted substituents selected from halogen, C1-C4 alkyl, C1-C4 alkoxy, —CO₂R', —CONR'R", —OCOR' and cyano, wherein R' and R' are independently selected from hydrogen and C1-C4 alkyl;

R2 is unsubstituted or substituted phenyl or unsubstituted pyridinyl, thiophenyl or furanyl, the substituents being selected from halogen, unsubstituted C1-C4 alkyl or unsubstituted C1-C4 alkoxy; and R8 is hydrogen or unsubstituted C1-C4 alkyl; or when X is NR8, R1 and R8 together with the nitrogen atom to which they are attached may form an unsubstituted, monocyclic, saturated 5- to 8-membered heterocyclyl group preferably selected from piperidinyl, morpholinyl or azepanyl.

In this embodiment, when R1 is 6-methoxy-pyridinyl, R2 is typically unsubstituted or substituted phenyl or unsubstituted thiophenyl or furanyl. In an alternative aspect of this embodiment, R2 is unsubstituted or substituted phenyl or unsubstituted thiophenyl or furanyl, the substituents being selected from halogen, unsubstituted C1-C4 alkyl or unsubstituted C1-C4 alkoxy.

The invention specifically provides the following indolizine derivatives of formula (I) as well as their pharmaceutically and agriculturally acceptable salts:

N-(2-Methoxy-phenyl)-2-oxo-2-(2-phenyl-indolizin-3-yl)-acetamide,
4-[2-Oxo-2-(2-phenyl-indolizin-3-yl)-acetylamino]-benzoic acid methyl ester,
2-Oxo-N-phenyl-2-(2-phenyl-indolizin-3-yl)-acetamide,
4-[2-Oxo-2-(2-phenyl-indolizin-3-yl)-acetylamino]-benzoic acid propyl ester,
2-[2-Oxo-2-(2-phenyl-indolizin-3-yl)-acetylamino]-benzoic acid methyl ester,
3-[2-Oxo-2-(2-phenyl-indolizin-3-yl)-acetylamino]-benzoic acid methyl ester,
4-[2-Oxo-2-(-phenyl-indolizin-3-yl)-acetylamino]-benzoic acid propyl ester,
4-[2-Oxo-2-(2-phenyl-indolizin-3-yl)-acetylamino]-benzoic acid butyl ester,
N-(3-Methoxy-phenyl)-2-oxo-2-(2-phenyl-indolizin-3-yl)-acetamide,
N-(4-Methoxy-phenyl)-2-oxo-2-(2-phenyl-indolizin-3-yl)-acetamide,
N-(4-Chloro-phenyl)-2-oxo-2-(2-phenyl-indolizin-3-yl)-acetamide,
N-(4-Cyano-phenyl)-2-oxo-2-(2-phenyl-indolizin-3-yl)-acetamide,
2-Oxo-2-(2-phenyl-indolizin-3-yl)-N-p-tolyl-acetamide,
2-Oxo-2-(2-phenyl-indolizin-3-yl)-N-pyridin-4-yl-acetamide,
2-Oxo-2-(2-phenyl-indolizin-3-yl)-N-pyridin-3-yl-acetamide,
2-Oxo-2-(2-phenyl-indolizin-3-yl)-N-pyridin-2-yl-acetamide,
4-[2-Oxo-2-(2-phenyl-indolizin-3-yl)-acetylamino]-benzoic acid,
N-(2,4-Dimethoxy-phenyl)-2-oxo-2-(2-phenyl-indolizin-3-yl)-acetamide,
N-(6-Methoxy-pyridin-3-yl)-2-oxo-2-(2-phenyl-indolizin-3-yl)-acetamide,
4-[2-Oxo-2-(2-phenyl-indolizin-3-yl)-acetylamino]-benzamide,
N-Methyl-4-[2-oxo-2-(2-phenyl-indolizin-3-yl)-acetylamino]-benzamide,
N,N-Dimethyl-4-[2-oxo-2-(2-phenyl-indolizin-3-yl)-acetamino]-benzamide,
5-[2-Oxo-2-(2-phenyl-indolizin-3-yl)-acetylamino]-thiophene-3-carboxylic acid methyl ester,
N-(4-Methoxy-phenyl)-2-oxo-2-(2-pyridin-4-yl-indolizin-3-yl)-acetamide,
N-(4-Methoxy-phenyl)-2-oxo-2-(2-pyridin-3-yl-indolizin-3-yl)-acetamide,
N-(4-Methoxy-phenyl)-2-oxo-2-(2-pyridin-2-yl-indolizin-3-yl)-acetamide,
N-(4-Methoxy-phenyl)-2-oxo-2-(2-thiophen-2-yl-indolizin-3-yl)-acetamide,
2-(2-Furan-2-yl-indolizin-3-yl)-N-(4-methoxy-phenyl)-2-oxo-acetamide,
2-[2-(4-Fluoro-phenyl)-indolizin-3-yl]-N-(4-methoxy-phenyl)-2-oxo-acetamide,
2-[2-(4-Fluoro-phenyl)-indolizin-3-yl]-2-oxo-N-p-tolyl-acetamide,
N-(2-,4-Dimethoxy-phenyl)-2-[2-(4-fluoro-phenyl)-indolizin-3-yl]-2-oxo-acetamide,
2-[2-(4-Fluoro-phenyl)-indolizin-3-yl]-N-(6-methoxy-pyridin-3-yl)-2-oxo-acetamide,
2-Oxo-2-(2-thiophen-2-yl-indolizin-3-yl)-N-p-tolyl-acetamide,
N-(2,4-Dimethoxy-phenyl)-2-oxo-2-(2-thiophen-2-yl-indolizin-3-yl)-acetamide,
N-(6-Methoxy-pyridin-3-yl)-2-oxo-2-(2-thiophen-2-yl-indolizin-3-yl)-acetamide,
2-(2-Furan-2-yl-indolizin-3-yl)-2-oxo-N-p-tolyl-acetamide,
N-(2,4-Dimethoxy-phenyl)-2-(2-furan-2-yl-indolizin-3-yl)-2-oxo-acetamide,
2-(2-Furan-2-yl-indolizin-3-yl)-N-(6-methoxy-pyridin-3-yl)-2-oxo-acetamide,
2-Oxo-2-(2-pyridin-4-yl-indolizin-3-yl)-N-p-tolyl-acetamide,
N-(2,4-Dimethoxy-phenyl)-2-oxo-2-(2-pyridin-4-yl-indolizin-3-yl)-acetamide,
2-Oxo-2-(2-pyridin-3-yl-indolizin-3-yl)-N-p-tolyl-acetamide,
N-(2,4-Dimethoxy-phenyl)-2-oxo-2-(2-pyridin-3-yl-indolizin-3-yl)-acetamide,
2-Oxo-2-(2-pyridin-2-yl-indolizin-3-yl)-N-p-tolyl-acetamide, N-(2,4-Dimethoxy-phenyl)-2-oxo-2-(2-pyridin-2-yl-indolizin-3-yl)-acetamide,
4-[2-Oxo-2-(2-phenyl-indolizin-3-yl)-acetoxy]-benzoic acid methyl ester,
N-Cyclohexyl-2-oxo-2-(2-phenyl-indolizin-3-yl)-acetamide,
N-Methyl-2-oxo-2-(2-phenyl-indolizin-3-yl)-acetamide,
N-Isopropyl-2-oxo-2-(2-phenyl-indolizin-3-yl)-acetamide,
N-(2-Methoxy-ethyl)-2-oxo-2-(2-phenyl-indolizin-3-yl)-acetamide,
N-Benzyl-2-oxo-2-(2-phenyl-indolizin-3-yl)-acetamide,
N,N-Dimethyl-2-oxo-2-(2-phenyl-indolizin-3-yl)-acetamide,
1-(2-Phenyl-indolizin-3-yl)-2-piperidin-1-yl-ethane-1,2-dione, The invention further specifically provides the following indolizine derivatives of formula (I) as well as their pharmaceutically and agriculturally acceptable salts:

N-(2-Methoxy-ethyl)-2-oxo-2-(2-pyridin-3-yl-indolizin-3-yl)-acetamide,
N-Methyl-2-oxo-N-phenyl-2-(2-phenyl-indolizin-3-yl)-acetamide,
N-Methyl-2-oxo-N-phenyl-2-(2-pyridin-3-yl-indolizin-3-yl)-acetamide,
2-(5-Methyl-2-phenyl-indolizin-3-yl)-2-oxo-N-p-tolyl-acetamide,
N-(6-Methoxy-pyridin-3-yl)-2-(5-methyl-2-phenyl-indolizin-3-yl)-2-oxo-acetamide,
2-(6-Methyl-2-phenyl-indolizin-3-yl)-2-oxo-N-p-tolyl-acetamide,
2-(7-Methyl-2-phenyl-indolizin-3-yl)-2-oxo-N-p-tolyl-acetamide,
N-(6-Methoxy-pyridin-3-yl)-2-(6-methyl-2-phenyl-indolizin-3-yl)-2-oxo-acetamide,
N-(6-Methoxy-pyridin-3-yl)-2-(7-methyl-2-phenyl-indolizin-3-yl)-2-oxo-acetamide,
N-(6-Methoxy-pyridin-3-yl)-2-(8-methyl-2-phenyl-indolizin-3-yl)-2-oxo-acetamide,
2-(6-Methoxy-2-phenyl-indolizin-3-yl)-N-(6-methoxy-pyridin-3-yl)-2-oxo-acetamide,
2-(6-Methoxy-2-phenyl-indolizin-3-yl)-2-oxo-N-p-tolyl-acetamide,
N-(4-Chloro-phenyl)-2-oxo-2-(2-pyridin-3-yl-indolizin-3-yl)-acetamide,
N-(4-Fluoro-phenyl)-2-oxo-2-(2-pyridin-3-yl-indolizin-3-yl)-acetamide,
2-(6-Methyl-2-pyridin-3-yl-indolizin-3-yl)-2-oxo-N-p-tolyl-acetamide,
N-(4-Fluoro-phenyl)-2-oxo-2-(2-phenyl-indolizin-3-yl)-acetamide,
N-(2-Fluoro-phenyl)-2-oxo-2-(2-phenyl-indolizin-3-yl)-acetamide,
2-Oxo-2-(2-phenyl-indolizin-3-yl)-N-(4-trifluoromethyl-phenyl)-acetamide,
2-Oxo-2-(2-phenyl-indolizin-3-yl)-N-o-tolyl-acetamide,
N-(4-Dimethylamino-phenyl)-2-oxo-2-(2-phenyl-indolizin-3-yl)-acetamide,
N-(4-Bromo-phenyl)-2-oxo-2-(2-phenyl-indolizin-3-yl)-acetamide,
N-(4-Acetyl-phenyl)-2-oxo-2-(2-phenyl-indolizin-3-yl)-acetamide,
2-Oxo-2-(2-phenyl-indolizin-3-yl)-N-m-tolyl-acetamide,
N-(2-Chloro-phenyl)-2-oxo-2-(2-phenyl-indolizin-3-yl)-acetamide,
2-[2-Oxo-2-(2-phenyl-indolizin-3-yl)-acetylamino]-benzoic acid ethyl ester,
N-(2,4-Dichloro-phenyl)-2-oxo-2-(2-phenyl-indolizin-3-yl)-acetamide,
N-(4-Fluoro-phenyl)-2-[2-(4-fluoro-phenyl)-indolizin-3-yl]-2-oxo-acetamide,
N-(4-Chloro-phenyl)-2-[2-(4-fluoro-phenyl)-indolizin-3-yl]-2-oxo-acetamide,
N-(2-Fluoro-phenyl)-2-oxo-2-(2-pyridin-3-yl-indolizin-3-yl)-acetamide,
2-Oxo-2-(2-pyridin-3-yl-indolizin-3-yl)-N-(4-trifluoromethyl-phenyl)-acetamide,
2-Oxo-2-(2-pyridin-3-yl-indolizin-3-yl)-N-o-tolyl-acetamide,
N-(4-Bromo-phenyl)-2-oxo-2-(2-pyridin-3-yl-indolizin-3-yl)-acetamide,
2-Oxo-2-(2-pyridin-3-yl-indolizin-3-yl)-N-m-tolyl-acetamide,
N-(2-Chloro-phenyl)-2-oxo-2-(2-pyridin-3-yl-indolizin-3-yl)-acetamide,
N-(4-Acetyl-phenyl)-2-oxo-2-(2-pyridin-3-yl-indolizin-3-yl)-acetamide,
2-Oxo-2-(2-phenyl-indolizin-3-yl)-N-(3-trifluoromethyl-phenyl)-acetamide,
1-(2,3-Dihydro-indol-1-yl)-2-(2-phenyl-indolizin-3-yl)-ethane-1,2-dione,
N-(4-Methanesulfonylamino-phenyl)-2-oxo-2-(2-phenyl-indolizin-3-yl)-acetamide,
N-(3,5-Dichloro-phenyl)-2-oxo-2-(2-phenyl-indolizin-3-yl)-acetamide,
N-[4-(Cyano-dimethyl-methyl)-phenyl]-2-oxo-2-(2-phenyl-indolizin-3-yl)-acetamide,
2-Oxo-2-(2-phenyl-indolizin-3-yl)-N-(3,4,5-trimethoxy-phenyl)-acetamide,
2-Oxo-2-(2-pyridin-3-yl-indolizin-3-yl)-N-(3-trifluoromethyl-phenyl)-acetamide,
N-(2,4-Dichloro-phenyl)-2-oxo-2-(2-pyridin-3-yl-indolizin-3-yl)-acetamide,
N-[4-(Cyano-dimethyl-methyl)-phenyl]-2-oxo-2-(2-pyridin-3-yl-indolizin-3-yl)-acetamide,
2-Oxo-2-(2-pyridin-3-yl-indolizin-3-yl)-N-(3,4,5-trimethoxy-phenyl)-acetamide,
N-(3,5-Dichloro-phenyl)-2-oxo-2-(2-pyridin-3-yl-indolizin-3-yl)-acetamide,
N-[3-(Cyano-dimethyl-methyl)-phenyl]-2-oxo-2-(2-phenyl-indolizin-3-yl)-acetamide,
N-(6-Dimethylamino-pyridin-3-yl)-2-oxo-2-(2-phenyl-indolizin-3-yl)-acetamide,
N-(4-Dimethylamino-phenyl)-2-oxo-2-(2-pyridin-3-yl-indolizin-3-yl)-acetamide,
N-[3-(Cyano-dimethyl-methyl)-phenyl]-2-oxo-2-(2-pyridin-3-yl-indolizin-3-yl)-acetamide,
2-[(E/Z)-Methoxyimino]-N-(4-methoxy-phenyl)-2-(2-phenyl-indolizin-3-yl)-acetamide,
N-(4-Methoxy-phenyl)-2-oxo-2-(2-o-tolyl-indolizin-3-yl)-acetamide,
N-(4-Methoxy-phenyl)-2-oxo-2-(2-m-tolyl-indolizin-3-yl)-acetamide,
N-(4-Methoxy-phenyl)-2-(8-methyl-2-phenyl-indolizin-3-yl)-2-oxo-acetamide,
2-[2-(3-Chloro-phenyl)-indolizin-3-yl]-N-(4-methoxy-phenyl)-2-oxo-acetamide,
2-[2-(3-Cyano-phenyl)-indolizin-3-yl]-N-(4-methoxy-phenyl)-2-oxo-acetamide,
N-(4-Methoxy-phenyl)-2-(5-methyl-2-phenyl-indolizin-3-yl)-2-oxo-acetamide,
N-(4-Methoxy-phenyl)-2-oxo-2-(2-p-tolyl-indolizin-3-yl)-acetamide, N-(4-Methoxy-phenyl)-2-(6-methoxy-2-phenyl-indolizin-3-yl)-2-oxo-acetamide,
N-[3-(2-Dimethylamino-ethoxy)-phenyl]-2-oxo-2-(2-phenyl-indolizin-3-yl)-acetamide,
N-(3-Methyl-3H-benzoimidazol-5-yl)-2-oxo-2-(2-phenyl-indolizin-3-yl)-acetamide,
N-(1-Methyl-1H-benzoimidazol-5-yl)-2-oxo-2-(2-phenyl-indolizin-3-yl)-acetamide,
N-(4-Dimethylamino-phenyl)-2-(6-methoxy-2-phenyl-indolizin-3-yl)-2-oxo-acetamide,
N-(4-{1-[(E/Z)-Methoxyimino]-ethyl}-phenyl)-2-oxo-2-(2-phenyl-indolizin-3-yl)-acetamide,
N-(2,4-Difluoro-phenyl)-2-[2-(3-fluoro-phenyl)-indolizin-3-yl]-2-oxo-acetamide,
2-[2-(3-Cyano-phenyl)-indolizin-3-yl]-N-(2,4-difluoro-phenyl)-2-oxo-acetamide,
N-(5-Chloro-2-methyl-phenyl)-2-oxo-2-(2-phenyl-indolizin-3-yl)-acetamide,
{3-[2-Oxo-2-(2-phenyl-indolizin-3-yl)-acetylamino]-phenoxy}-acetic acid,
N-(2-Allyloxy-4-fluoro-phenyl)-2-oxo-2-(2-phenyl-indolizin-3-yl)-acetamide,
2-Methyl-2-[2-oxo-2-(2-phenyl-indolizin-3-yl)-acetylamino]-propionic acid ethyl ester,
2-Methyl-2-[2-oxo-2-(2-phenyl-indolizin-3-yl)-acetylamino]-3-phenyl-propionic acid ethyl ester,
N-(4-{1-[(E/Z)-Hydroxyimino]-ethyl}-phenyl)-2-oxo-2-(2-phenyl-indolizin-3-yl)-acetamide,
2-Oxo-2-(2-phenyl-indolizin-3-yl)-N-(4-piperidin-1-yl-phenyl)-acetamide,
N-(4-Morpholin-4-yl-phenyl)-2-oxo-2-(2-phenyl-indolizin-3-yl)-acetamide,
N-(4-Isopropyl-phenyl)-2-oxo-2-(2-phenyl-indolizin-3-yl)-acetamide,
N-(6-Dimethylamino-pyridin-3-yl)-2-oxo-2-(2-pyridin-3-yl-indolizin-3-yl)-acetamide,
2-[(E/Z)-2-Dimethylamino-ethoxyimino]-N-(4-methoxy-phenyl)-2-(2-phenyl-indolizin-3-yl)-acetamide,
2-[(E/Z)-3-Dimethylamino-propoxyimino]-N-(4-methoxy-phenyl)-2-(2-phenyl-indolizin-3-yl)-acetamide,
N-(3-Allyl-4-fluoro-2-methoxy-phenyl)-2-oxo-2-(2-phenyl-indolizin-3-yl)-acetamide,
N-[4-(1-Hydroxy-ethyl)-phenyl]-2-oxo-2-(2-phenyl-indolizin-3-yl)-acetamide,
N-(1-Methyl-1H-indol-5-yl)-2-oxo-2-(2-phenyl-indolizin-3-yl)-acetamide,
N-(4-Methanesulfonyl-phenyl)-2-oxo-2-(2-phenyl-indolizin-3-yl)-acetamide,
4-[1-(4-Methoxy-phenylcarbamoyl)-1-(2-phenyl-indolizin-3-yl)-meth-(E/Z)-ylideneaminooxy]-butyric acid,
2-Oxo-2-(2-phenyl-indolizin-3-yl)-N-(4-thiomorpholin-4-yl-phenyl)-acetamide,
2-Oxo-2-(2-phenyl-indolizin-3-yl)-N-(2,3,4-trimethyl-phenyl)-acetamide,
2-Oxo-2-(2-phenyl-indolizin-3-yl)-N-(4-pyrrolidin-1-yl-phenyl)-acetamide,
N-(1-Methyl-2,3-dihydro-1H-indol-5-yl)-2-oxo-2-(2-phenyl-indolizin-3-yl)-acetamide,
N-[4-(4-Methyl-piperazin-1-yl)-phenyl]-2-oxo-2-(2-phenyl-indolizin-3-yl)-acetamide,
N-Benzyl-N-methyl-3-[2-oxo-2-(2-phenyl-indolizin-3-yl)-acetylamino]-benzamide,
N-[4-(2-Methyl-[1,3]dioxolan-2-yl)-phenyl]-2-oxo-2-(2-phenyl-indolizin-3-yl)-acetamide,
N-(2,4-Difluoro-phenyl)-2-[2-(2,4-difluoro-phenyl)-indolizin-3-yl]-2-oxo-acetamide,
Diethyl-carbamic acid 3-[2-oxo-2-(2-phenyl-indolizin-3-yl)-acetylamino]-phenyl ester,
N-(3-Acetyl-phenyl)-2-oxo-2-(2-phenyl-indolizin-3-yl)-acetamide,
1-Methyl-4-{4-[2-oxo-2-(2-phenyl-indolizin-3-yl)-acetylamino]-phenyl}-thiomorpholin-1-ium,
N-(4-Oxazol-2-yl-phenyl)-2-oxo-2-(2-phenyl-indolizin-3-yl)-acetamide,
N-(2,4-Difluoro-phenyl)-2-[2-(2-methoxy-phenyl)-indolizin-3-yl]-2-oxo-acetamide,
2-Oxo-2-(2-phenyl-indolizin-3-yl)-N-[4-(pyridin-2-ylamino)-phenyl]-acetamide,
2-Oxo-2-(2-phenyl-indolizin-3-yl)-N-[4-(1H-tetrazol-5-yl)-phenyl]-acetamide,
2-Oxo-N-[4-(4-oxo-piperidin-1-yl)-phenyl]-2-(2-phenyl-indolizin-3-yl)-acetamide,
N-(4-Dimethylamino-3-methyl-phenyl)-2-oxo-2-(2-phenyl-indolizin-3-yl)-acetamide,
2-Dimethylamino-5-[2-oxo-2-(2-phenyl-indolizin-3-yl)-acetylamino]-benzoic acid,
1-{4-[2-Oxo-2-(2-phenyl-indolizin-3-yl)-acetylamino]-phenyl}-pyrrolidine-2-carboxylic acid methyl ester,
2-Oxo-2-(2-phenyl-indolizin-3-yl)-N-[4-(pyrimidin-2-ylamino)-phenyl]-acetamide,
2-[2-(2-Chloro-phenyl)-indolizin-3-yl]-N-(2,4-difluoro-phenyl)-2-oxo-acetamide,
N-(4-Dimethylaminomethyl-phenyl)-2-oxo-2-(2-phenyl-indolizin-3-yl)-acetamide,
N-(3-Acetyl-4-methoxy-phenyl)-2-oxo-2-(2-phenyl-indolizin-3-yl)-acetamide,
2-[2-(2-Methyl-pyridin-3-yl)-indolizin-3-yl]-2-oxo-N-[4-(2,2,3,3-tetrafluoro-propoxy)-phenyl]-acetamide,
2-Oxo-N-[4-(2-oxo-propyl)-phenyl]-2-(2-phenyl-indolizin-3-yl)-acetamide,
2-Oxo-2-(2-phenyl-indolizin-3-yl)-N-[4-(thiazol-2-ylamino)-phenyl]-acetamide,
2-Oxo-N-[6-(2,2,3,3-tetrafluoro-propoxy)-pyridin-3-yl]-2-(2-o-tolyl-indolizin-3-yl)-acetamide,
N-[4-(3,5-Dimethyl-isoxazol-4-yl)-phenyl]-2-oxo-2-(2-phenyl-indolizin-3-yl)-acetamide,
N-(3-Oxazol-2-yl-phenyl)-2-oxo-2-(2-phenyl-indolizin-3-yl)-acetamide,
N-(6-Dipropylamino-pyridin-3-yl)-2-oxo-2-(2-phenyl-indolizin-3-yl)-acetamide,
N-(4-Diethylamino-3-methyl-phenyl)-2-oxo-2-(2-phenyl-indolizin-3-yl)-acetamide,
N-(4-Oxazol-5-yl-phenyl)-2-oxo-2-(2-phenyl-indolizin-3-yl)-acetamide,
N-(4-Dimethylamino-3-oxazol-2-yl-phenyl)-2-oxo-2-(2-phenyl-indolizin-3-yl)-acetamide,
2-Oxo-2-(2-phenyl-indolizin-3-yl)-N-(4-thiazol-2-yl-phenyl)-acetamide.

Compounds of the invention containing one or more chiral centre may be used in enantiomerically or diastereoisomerically pure form, or in the form of a mixture of isomers. For the avoidance of doubt, the compounds of the invention can, if desired, be used in the form of solvates. Further, for the avoidance of doubt, the compounds of the invention may be used in any tautomeric form.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

The present invention also provides prodrugs of the compounds of the invention. A prodrug is an analogue of a compound of the invention which will be converted in vivo to the desired active compound. Examples of suitable prodrugs include compounds of formula (I) which have been modified at a hydroxyl or carboxylic acid group to form an ester. Further suitable prodrugs include those in which a nitrogen atom of a compound of formula (I) is quaternised by addition of an ester or alkyl ester group. For example, the nitrogen atom of an amine group or heterocyclyl ring on a substituent $R_1$ or $R_2$ may be quaternised by addition of a —$CH_2$—O—COR group, wherein R is typically methyl or tert-butyl.

Certain indolizinyl derivatives of formula (I) are novel. The present invention accordingly provides an indolizinyl derivative of formula (IB) as well as the salts thereof:

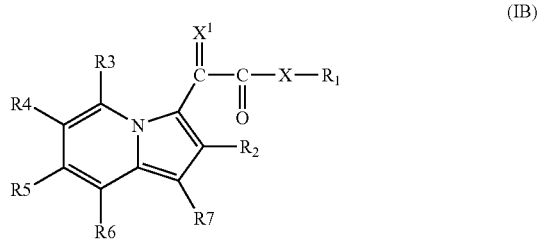

(IB)

wherein:

R3, R4, R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, C1-C4 alkoxy, —$CO_2R'$, —CONR'R", —COR', CN, —$NO_2$, —NR'R", $CF_3$ or —Y—Z, with the proviso that when $X^1$ is O, X is —O—, R1 is ethyl and R4 to R7 are all hydrogen, R3 is not methyl; when $X^1$ is O, X is —NMe-, R1 is methyl, R2 is unsubstituted phenyl and R4 to R7 are all hydrogen, R3 is not hydrogen; and when $X^1$ is O, X is —O—, R1 is hydrogen, R2 is methyl and R4 to R7 are all hydrogen, R3 is not hydrogen; and X, $X^1$, R1, R2, R7, R', R", Y and Z are as defined for the indolizinyl derivatives of formula (I) or (IA), with the proviso that when $X^1$ is NOH, X is —NR8-, —O—, —S—, —SO— or —$SO_2$—,
other than the commercially available compounds listed above.

Typically, in the derivatives of formula (IB), R3, R4, R5 and R6 are unsubstituted. Preferably, no more than one of R3, R4, R5, R6 and R7 is $NO_2$, and no more than one of R3, R4, R5, R6 and R7 is CN. Typically none, one or two, preferably none or one, of R3, R4, R5 and R6 contains an aryl or heterocyclyl group or moiety.

In one embodiment, R3, R4, R5 and R6 independently represent phenyl, benzyl, pyridyl, hydrogen, halogen, C1-C8 alkyl, C2-C8 alkenyl, C2-C8 alkynyl, C1-C4 alkoxy, —$CO_2R'$, CONR'R", —COR', —CN, —$NO_2$, —NR'R" or —$CF_3$ wherein R' and R" are independently hydrogen or C1-C4 alkyl. In another embodiment, R3, R4, R5 and R6 independently represent hydrogen, halogen, C1-C8 alkyl, C2-C8 alkenyl, C2-C8 alkynyl, C1-C4 alkoxy, —$CO_2R'$, CONR'R", —COR', —CN, —$NO_2$, —NR'R" or —$CF_3$ wherein R' and R" are independently hydrogen or C1-C4 alkyl. In yet another embodiment, R3, R4, R5 and R6 independently represent hydrogen, halogen, methoxy or unsubstituted C1-C4 alkyl, for example hydrogen, halogen or unsubstituted C1-C4 alkyl, preferably hydrogen.

Typically, in the derivatives of formula (IB), R1 is phenyl, pyridinyl, thiophenyl, furanyl, benzimidazolyl, indolyl, dihydroindolyl, unsubstituted C5-C6 cycloalkyl, unsubstituted or substituted C1, C3 or C4 alkyl, substituted C2 alkyl, -A1-L1-A2 or -L2-A2, wherein the substituents on the substituted alkyl groups are chosen from C1-C4 alkoxy or —$CO_2$(C1-C4 alkyl), and wherein the aryl and heterocyclyl groups are unsubstituted or substituted with one, two or three substituents selected from the unsubstituted groups halogen, —$CO_2R'$, —CONR'R", OCOR', hydroxyl, cyano, —NR'R", —COR', —$NSO_2R'$, —O(C2-C4 alkenyl), C2-C4 alkenyl, —$SO_2R'$, —OCONR'R", —CR'=NOR" and $CF_3$, and from C1-C4 alkyl and C1-C4 alkoxy groups which are unsubstituted or substituted with one unsubstituted group selected from hydroxyl, di(C1-C4 alkyl)amino, cyano and —$CO_2R'$, wherein R' and R" are independently selected from hydrogen and C1-C4 alkyl.

In a further embodiment, in the derivatives of formula (IB), X is —NR8-, —O—, —S— or —$SO_2$—.

Preferred compounds of the invention are the indolizinyl derivatives of formula (IA) as well as their salts, other than compounds in which X is —NMe-, R1 is methyl, R2 is unsubstituted phenyl and R3 to R7 are hydrogen.

Suitable salts of the compounds of the invention include those mentioned herein as examples of pharmaceutically and agriculturally acceptable salts.

A derivative of formula (I), where $X^1$=NOR9, may be prepared by a process comprising reacting a compound of formula (I), where $X^1$=O, and a compound of formula (A), wherein R9 is hereinbefore defined. Typically, the reaction takes place in the presence of an organic solvent and a base. Preferably the solvent is ethanol and the base is potassium hydroxide. Typically, the reaction is heated to reflux.

(A)

A compound of formula (A) may be prepared by reacting a compound of formula (B) with conc. hydrochloric acid, wherein R9 is hereinbefore defined. Typically, the reaction is heated to reflux overnight.

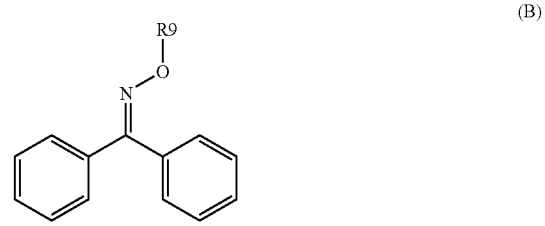

(B)

A compound of formula (B) may be prepared by reacting a compound of formula (C) with diphenyl-methanone oxime. In the compound of formula (C), Hal is defined as a halogen atom, typically chlorine or bromine, and R9 is hereinbefore defined. Typically, the reaction takes place in the presence of an organic solvent and a base. Preferably the solvent is DMSO or acetonitrile and the base is potassium hydroxide or potassium carbonate. The temperature required for the reaction to occur is dependent upon the reagents used.

Hal-R9 (C)

A derivative of formula (I), where X1=O, may be prepared by a process comprising reacting a compound of formula (II), wherein R2, R3, R4, R5, R6 and R7 are as hereinbefore defined, with a compound of formula (III), wherein R1 and X are as hereinbefore defined. Typically, the reaction takes place in the presence of an organic solvent and a base. Preferably the solvent is dichloromethane and the base is triethylamine. Typically, the reaction is carried out at 0° C. initially while the reagents are added and then stirred at room temperature until the reaction is complete. Compounds of formula (III) are typically available from commercial sources or can be prepared by known methods. Details of the synthesis of certain compounds of formula (III) are provided hereinafter.

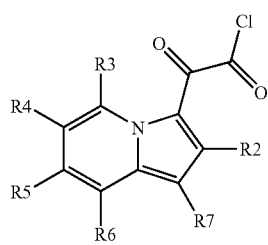

(II)

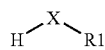

(III)

A compound of formula (II) may be prepared by reacting a compound of formula (IV), wherein R2, R3, R4, R5, R6 and R7 are as hereinbefore defined, with preferably oxalyl chloride. Typically the reaction takes place in an organic solvent. Preferably, the solvent is a tetrahydrofuran, a mixture of tetrahydrofuran/toluene, or diethyl ether. Typically, the reaction is carried out at 0° C. initially while the reagents are added and then stirred at room temperature until the reaction is complete.

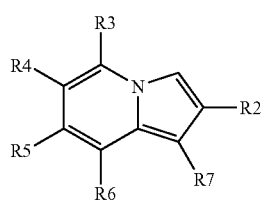

(IV)

A compound of formula (IV) may be prepared by reacting a compound of formula (V), wherein R2, R3, R4, R5, R6, and R7 are as hereinbefore defined, with a base. Preferably the solvent is water and the base is NaHCO$_3$. Typically, the reaction is heated to reflux.

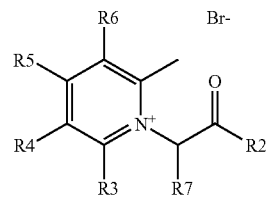

(V)

A compound of formula (V) may be prepared by reacting a compound of formula (VI), wherein R2 is hereinbefore defined, with a compound of formula (VII), wherein R3, R4, R5, R6, R7 are as hereinbefore defined. Typically, the reaction takes place in the presence of an organic solvent. Preferably the solvent is methanol. Typically, the reaction is heated to reflux.

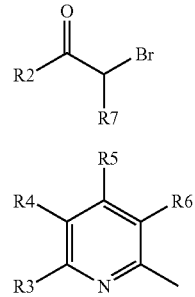

(VI)

(VII)

Compounds of formula (VI) are available from standard commercial sources or may be prepared by reacting a compound of formula (VIII), which are available from standard commercial sources, wherein R2 is hereinbefore defined, with a suitable brominating agent. Typically, the brominating conditions are hydrobromic acid in acetic acid, followed by pyridinium tribromide or bromine in dioxane/ether. Typically, the reaction is kept at room temperature.

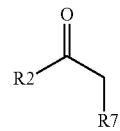

(VIII)

Many of the starting materials referred to in the reactions described above are available from commercial sources or can be prepared by analogy with known methods.

The compounds of the invention have antifungal activity. Accordingly, they may be used in a method of treating a subject suffering from or susceptible to a fungal disease, which method comprises administering to said subject an effective amount of an indolizinyl derivative of formula (I) or (IA) or a pharmaceutically acceptable salt thereof. The indolizinyl derivatives of formula (I) or (IA) or the pharmaceutically acceptable salts thereof may also be used in the manufacture of a medicament for use in the prevention or treatment of a fungal disease.

Preferably, the fungal disease comprises an infection by a fungus, more preferably an Ascomycete, and even more preferably, an organism selected from the genera *Aspergillus; Blumeria; Candida; Colletotrichium; Cryptococcus;*

*Enzcephalitozoon; Fusarium; Histoplasma; Leptosphaeria; Mycosphaerella; Neurospora, Phytophthora; Plasmopara; Pneumocystis; Pyricularia; Pythium; Puccinia; Rhizoctonia; Trichophyton*; and *Ustilago*.

Preferably, the fungal disease comprises an infection by an organism of the genus *Aspergillus* or *Candida*, for example *Aspergillus*.

Preferably, the fungal disease comprises an infection by an organism selected from the species *Aspergillus flavus; Aspergillus fumigatus; Aspergillus nidulans; Aspergillus niger; Aspergillus parasiticus; Aspergillus terreus; Blumeria graminis; Candida albicans; Candida cruzei; Candida glabrata; Candida parapsilosis; Candida tropicalis; Colletotrichium trifolii, Cryptococcus neoformans; Encephalitozoon cuniculi; Fusarium graminarium; Fusarium solani; Fusarium sporotrichoides; Histoplasma capsulata; Leptosphaeria nodorum; Mycosphaerella graminicola; Phytophthora capsici; Phytophthora infestans; Plasmopara viticola; Pneumocystis jiroveci; Puccinia coronata; Puccinia graminis; Pyricularia oryzae; Pythium ultimum; Rhizoctonia solani; Trichophyton interdigitale; Trichophyton rubrum*; and *Ustilago maydis*.

Preferably, the fungal disease comprises an infection by *Aspergillus fumigatus*.

Examples of fungal diseases, which can be prevented or treated using the compounds of the invention, include both systemic and superficial infections. The fungal diseases include invasive fungal diseases caused by *Aspergillus* and *Candida* species such as aspergillosis or candidiasis, but also local forms of these infections. The compounds of the invention are particularly useful against diseases caused by *Aspergillus* species, for which a fungicidal drug is required which has lower toxicity than amphotericin. The invention also provides for the treatment of dermatological infections.

The diseases caused by *Aspergillus* species include diseases caused by *A. fumigatus, A. flavus, A. terreus* and *A. niger*.

The diseases cause by *Candida* species include diseases caused by *C. albicans, C. glabrata, C. krusei, C. tropicalis* and *C. parapsillosis*.

The relative importance of the human fungal pathogens by prevalence is approximately, for *Aspergillus* species:

A. *fumigatus* 85%
A. *flavus* 8%
A. *terreus* 5%
A. *niger* 2% and for *Candida* species:

C. *albicans* 80%
C. *glabrata* 9%
C. *parapsillosis* 5%
C. *tropicalis* 4%
C. *krusei* 2%

Examples of systemic infections which might be prevented or treated using the compounds of the invention include: systemic candidiasis; pulmonary aspergillosis, e.g. in immunosuppressed patients such as bone marrow recipients or AIDS patients; systemic aspergillosis; cryptococcal meningitis; rhinocerebral mucomycosis; blastomycosis; histoplasmosis; coccidiomycosis; paracoccidiomycosis; and disseminated sporotrichosis.

Examples of superficial infections, which can be prevented or treated using the compounds of the invention, include: ring worm; athlete's foot; tinea unguium (nail infection); candidiasis of skin, mouth or vagina; and chronic mucocutaneous candidiasis.

The present invention includes a pharmaceutical composition comprising a compound according to the invention and a pharmaceutically acceptable carrier or diluent. Said pharmaceutical composition typically contains up to 85 wt % of a compound of the invention. More typically, it contains up to 50 wt % of a compound of the invention. Preferred pharmaceutical compositions are sterile and pyrogen free. Further, the pharmaceutical compositions provided by the invention typically contain a compound of the invention which is a substantially pure optical isomer.

The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, either subcutaneously, intravenously, intramuscularly, intrasternally, transdermally or by infusion techniques. The compounds may also be administered as suppositories.

A compound of the invention is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginte, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

A therapeutically effective amount of a compound of the invention is administered to a patient. A typical daily dose is up to 50 mg per kg of body weight, for example from 0.001 to 50 mg per kg of body weight, according to the activity of the specific compound, the age, weight and conditions of the subject to be treated, the type and severity of the disease and the frequency and route of administration. Preferably, daily dosage levels are from 0.05 mg to 2 g, preferably from 0.1 mg to 10 mg. The compound of the invention is typically administered to the patient in a non-toxic amount.

The present invention also provides a method of controlling a fungal disease of a plant, which comprises applying to the locus of the plant a derivative of formula (I) or an agriculturally acceptable salt thereof.

The compounds of the invention may, for example, be applied to the seeds of the plants, to the medium (e.g. soil or water) in which the plants are grown, or to the foliage of the plants.

Examples of fungal diseases of plants which can be controlled using the compounds of the invention include fungal diseases caused by the following plant pathogens: *Blumeria graminis; Colletotrichium trifolii; Fusarium graminarium; Fusarium solani; Fusarium sporotrichoides; Leptosphaeria nodorum; Magnaporthe grisea; Mycosphaerella graminicola; Neurospora crassa; Phytophthora capsici; Phytophthora infestans; Plasmopara viticola; Puccinia coronata; Puccinia graminis; Pyricularia oryzae; Pythium ultimum; Rhizoctonia solani; Trichophyton rubrum*; and *Ustilago maydis*.

The present invention includes a composition comprising a compound of the invention, or an agriculturally acceptable salt thereof, and an agriculturally acceptable carrier or diluent. Said agricultural composition typically contains up to 85 wt % of a compound of the invention. More typically, it contains up to 50 wt % of a compound of the invention.

Suitable agriculturally acceptable salts include salts with agriculturally acceptable acids, both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Salts may also be formed with agriculturally acceptable bases such as alkali metal (e.g. sodium or potassium) and alkaline earth metal (e.g. calcium or magnesium) hydroxides and organic bases such as alkyl amines, aralkyl amines or heterocyclic amines. A preferred agriculturally acceptable salt is the hydrochloride salt.

The compounds of the invention may be applied in combination with inert carriers or diluents, as in aqueous sprays, granules and dust formulations in accordance with established practice in the art. An aqueous spray is usually prepared by mixing a wettable powder or emulsifiable concentrate formulation of a compound of the invention with a relatively large amount of water to form a dispersion.

Wettable powders may comprise an intimate, finely divided mixture of a compound of the invention, an inert solid carrier and a surface-active agent. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates may comprise a solution of a compound of the invention in a liquid carrier which is a mixture of a water-immiscible solvent and a surfactant, including an emulsifier. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

The fungicide formulations desirably contain from 0.1 percent to 95 percent by weight of the compound of the invention and from 0.1 to 75 percent of an inert carrier or surfactant. The direct application to plant seeds prior to planting may be accomplished in some instances by mixing either a powdered solid compound of the invention or a dust formulation with seed to obtain a substantially uniform coating which is very thin and represents only one or two percent by weight or less, based on the weight of the seed. In some instances, however, a non-phytotoxic solvent such as methanol is conveniently employed as a carrier to facilitate the uniform distribution of the compound of the invention on the surface of the seed.

When a compound of the invention is to be applied to the soil, as for pre-emergence protection, granular formulations or dusts are sometimes more convenient than sprays. A typical granular formulation comprises a compound of the invention dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound is sprayed on the granules while they are being agitated in a suitable mixing apparatus, after which the granules are dried with a current of air during continued agitation. Dust formulations customarily employ essentially the same inert diluents as wettable powders and granules, but are well-mixed in powder form and do not usually contain emulsifiers. Dusts may contain some surface active agents to facilitate uniform distribution of the active ingredient in the formulation and to improve the uniformity and adhesion of the dust coating on seeds and plants. The colloidal dispersion of dust formulations in the air is usually prevented by incorporation of a minor amount of an oily or waxy material in the formulation to cause agglomeration of colloidal size particles. In this way the dust may be applied to seeds or plants without generation of an air-polluting aerosol.

The following examples illustrate the invention but are not intended to limit the scope of the invention. In this regard, it is important to understand that the particular assay used in the Examples section is designed only to provide an indication of anti-fungal activity. There are many assays available to determine such activity, and a negative result in any one particular assay is therefore not determinative.

Reference Example 1

1-(2-Chloro-pyridin-3-yl)-ethanone a) Preparation of 2-chloro-nicotinoyl chloride 2-Chloro nicotinic acid (5 g, 31.8 mmol) was heated to reflux with redistilled thionyl chloride (5.6 g, 47 mmol) for 8 hr, resulting in a clear solution. The reaction mixture was concentrated to dryness and the traces of thionyl chloride co-distilled with toluene (15 ml) to give 2-chloro-nicotinoyl chloride (5.2 g, 94%) as oil.

b) Preparation of 1-(2-chloro-pyridin-3-yl)ethanone

Triethylamine (7.4 g, 73 mmol) was added to a solution of diethyl malonate (5.6 g, 35 mmol) and anhydrous magnesium chloride (1.9 g, 20 mmol) in toluene (15 ml) under inert atmosphere. After stirring for 1 hr at room temperature, a solution of 2-chloro nicotinoyl chloride (5.2 g, 29 mmol) in toluene (5 ml) was added and the reaction mixture was stirred at room temperature for a further 1 hr. The reaction was quenched with ice cold 2N hydrochloric acid (20 ml), and the organic layer was separated and concentrated to dryness. The resultant residue was dissolved in a mixture of 3:2 DMSO-water and heated at 120-130° C. for 6 hr. The reaction mixture was cooled to room temperature and diluted with ethyl acetate (100 ml). The organic layer was washed once with bicarbonate solution, then several times with water, and finally with brine. The organic layer was then dried over anhydrous sodium sulfate, filtered and concentrated to dryness under reduced pressure to yield 1-(2-chloro-pyridin-3-yl)ethanone (1 g, 25%) as oil.

Reference Example 2

2-Bromo-1-pyridin-3-yl-ethanone

To a solution of 3-acetyl pyridine (2.71 ml, 24.74 mmol) in acetic acid (7.5 ml) was added 33% hydrobromic acid in acetic acid (7.5 ml) and then pyridinium tribromide (8.70 g, 27.21 mmol). The reaction mixture was stirred at room temperature for 12 hr to give a solid. The solid was filtered, washed with acetic acid and hexane and then dried under vacuum to give 2-bromo-1-pyridin-3-yl-ethanone 3.61 g (52%).

Reference Examples 3 to 7

The compounds set out below were prepared in the same way as in Example 2, using appropriate starting materials.

| Example | Compound |
| --- | --- |
| 3 | 2-Bromo-1-pyridin-2-yl-ethanone |
| 4 | 2-Bromo-1-pyridin-4-yl-ethanone |
| 5 | 2-Bromo-1-(4-fluoro-phenyl)-ethanone |
| 6 | 2-Bromo-1-thiophen-2-yl-ethanone |
| 7 | 2-Bromo-1-furan-2-yl-ethanone |

Reference Example 8

2-Bromo-1-m-tolyl-ethanone

To a solution of 1-m-tolyl-ethanone (6.0 g, 44.72 mmol) in dioxane (5 ml), bromine (7.14 g, 44.72 mmol) in dioxane (10 ml) and ether (15 ml) was added and stirred at room temperature for 5 hr. The reaction mixture was poured into ice water and the compound was extracted using ethyl acetate. The organic layer was washed with water and brine, dried over anhydrous sodium sulfate, filtered and then evaporated to give crude 2-bromo-1-m-tolyl-ethanone, 7.6 g (80%). The crude compound obtained was used in the next step without further purification.

Reference Examples 9 to 15

The compounds set out below were prepared in the same way as in Example 8, using appropriate starting materials.

| Example | Compound |
| --- | --- |
| 9 | 2-Bromo-1-o-tolyl-ethanone |
| 10 | 2-Bromo-1-p-tolyl-ethanone |
| 11 | 3-(2-Bromo-acetyl)-benzonitrile |
| 12 | 2-Bromo-1-(3-fluoro-phenyl)-ethanone |
| 13 | 2-Bromo-1-(2,4-difluoro-phenyl)-ethanone |
| 14 | 2-Bromo-1-(3-chloro-phenyl)-ethanone |
| 15 | 2-Bromo-1-(2-chloro-pyridin-3-yl)-ethanone |

Reference Example 16

2-Methyl-1-(2-oxo-2-phenyl-ethyl)-pyridinium bromide

2-Picoline (10.0 g, 0.1 mol) was added to a solution of alpha-bromoacetophenone (21.4 g, 0.1 mol) in methanol (150 ml). The solution was heated to reflux for 1 hr. The solvent was evaporated under vacuum to yield a solid, which was recrystallised from ethyl acetate/methanol. The resulting white solid was dried under vacuum to give 2-methyl-1-(2-oxo-2-phenyl-ethyl)-pyridinium bromide (18.0 g, 86%).

Reference Examples 17 to 38

The compounds set out below were prepared in the same way as in Example 16, using appropriate starting materials.

| Example | Compound |
| --- | --- |
| 17 | 2-Methyl-1-(2-oxo-2-pyridin-2-yl-ethyl)-pyridinium bromide |
| 18 | 2-Methyl-1-(2-oxo-2-pyridin-3-yl-ethyl)-pyridinium bromide |
| 19 | 2-Methyl-1-(2-oxo-2-pyridin-4-yl-ethyl)-pyridinium bromide |
| 20 | 1-[2-(4-Fluoro-phenyl)-2-oxo-ethyl]-2-methyl-pyridinium bromide |
| 21 | 2-Methyl-1-(2-oxo-2-thiophen-2-yl-ethyl)-pyridinium bromide |
| 22 | 1-(2-Furan-2-yl-2-oxo-ethyl)-2-methyl-pyridinium bromide |
| 23 | 2,6-Dimethyl-1-(2-oxo-2-phenyl-ethyl)-pyridinium bromide |
| 24 | 2,5-Dimethyl-1-(2-oxo-2-phenyl-ethyl)-pyridinium bromide |
| 25 | 2,4-Dimethyl-1-(2-oxo-2-phenyl-ethyl)-pyridinium bromide |
| 26 | 2,3-Dimethyl-1-(2-oxo-2-phenyl-ethyl)-pyridinium bromide |
| 27 | 5-Methoxy-2-methyl-1-(2-oxo-2-phenyl-ethyl)-pyridinium bromide |
| 28 | 2,5-Dimethyl-1-(2-oxo-2-pyridin-3-yl-ethyl)-pyridinium bromide |
| 29 | 2-Methyl-1-(2-oxo-2-o-tolyl-ethyl)-pyridinium bromide |
| 30 | 2-Methyl-1-(2-oxo-2-m-tolyl-ethyl)-pyridinium bromide |
| 31 | 2-Methyl-1-(2-oxo-2-p-tolyl-ethyl)-pyridinium bromide |
| 32 | 1-[2-(3-Cyano-phenyl)-2-oxo-ethyl]-2-methyl-pyridinium bromide |
| 33 | 1-[2-(3-Fluoro-phenyl)-2-oxo-ethyl]-2-methyl-pyridinium bromide |
| 34 | 1-[2-(3-Chloro-phenyl)-2-oxo-ethyl]-2-methyl-pyridinium bromide |
| 35 | 1-[2-(2-Chloro-phenyl)-2-oxo-ethyl]-2-methyl-pyridinium bromide |
| 36 | 1-[2-(2,4-Difluoro-phenyl)-2-oxo-ethyl]-2-methyl-pyridinium bromide |
| 37 | 1-[2-(2-Methoxy-phenyl)-2-oxo-ethyl]-2-methyl-pyridinium bromide |
| 38 | 1-[2-(2-chloro-pyridin-3-yl)-2-oxo-ethyl]-2-methyl-pyridinium bromide |

Reference Example 39

2-Phenyl-indolizine

A solution of sodium hydrogen carbonate (10.5 g, 119.8 mmol) in water (125 ml) was added to 2-methyl-1-(2-oxo-2-phenyl-ethyl)-pyridinium bromide (35.0 g, 119.8 mmol) and the reaction heated to reflux for 30 min. The resultant solid was filtered, washed with water and then dried under vacuum to yield 2-phenyl-indolizine (16.0 g, 70%).

Reference Examples 40 to 61

The compounds set out below were prepared in the same way as in Example 39, using appropriate starting materials.

| Example | Compound |
|---|---|
| 40 | 2-Pyridin-2-yl-indolizine |
| 41 | 2-Pyridin-3-yl-indolizine |
| 42 | 2-Pyridin-4-yl-indolizine |
| 43 | 2-(4-Fluoro-phenyl)-indolizine |
| 44 | 2-Thiophen-2-yl-indolizine |
| 45 | 2-Furan-2-yl-indolizine |
| 46 | 5-Methyl-2-phenyl-indolizine |
| 47 | 6-Methyl-2-phenyl-indolizine |
| 48 | 7-Methyl-2-phenyl-indolizine |
| 49 | 8-Methyl-2-phenyl-indolizine |
| 50 | 6-Methoxy-2-phenyl-indolizine |
| 51 | 6-Methyl-2-pyridin-3-yl-indolizine |
| 52 | 2-o-Tolyl-indolizine |
| 53 | 2-m-Tolyl-indolizine |
| 54 | 2-p-Tolyl-indolizine |
| 55 | 3-Indolizin-2-yl-benzonitrile |
| 56 | 2-(3-Fluoro-phenyl)-indolizine |
| 57 | 2-(3-Chloro-phenyl)-indolizine |
| 58 | 2-(2-Chloro-phenyl)-indolizine |
| 59 | 2-(2,4-Difluoro-phenyl)-indolizine |
| 60 | 2-(2-Methoxy-phenyl)-indolizine |
| 61 | 2-(2-chloro-pyridin-3-yl)-indolizine |

Reference Example 62

Oxo-(2-thiophen-2-yl-indolizin-3-yl)-acetyl chloride

To an ice-cold solution of 2-thiophen-2-yl-indolizine (0.5 g, 2.51 mmol) in THF (8 ml) was added oxalyl chloride (0.3 ml, 3.48 mmol). The reaction mixture was stirred at room temperature for 30 min. The solvent was evaporated under vacuum. The crude product was recrystallized from dichloromethane-hexane to give oxo-(2-thiophen-2-yl-indolizin-3-yl)-acetyl chloride (0.3 g, 41%).

Reference Examples 63 to 84

The compounds set out below were prepared in the same way as in Example 62, using appropriate starting materials.

| Example | Compound |
|---|---|
| 63 | Oxo-(2-phenyl-indolizin-3-yl)-acetyl chloride |
| 64 | Oxo-(2-pyridin-2-yl-indolizin-3-yl)-acetyl chloride |
| 65 | Oxo-(2-pyridin-3-yl-indolizin-3-yl)-acetyl chloride |
| 66 | Oxo-(2-pyridin-4-yl-indolizin-3-yl)-acetyl chloride |
| 67 | [2-(4-Fluoro-phenyl)-indolizin-3-yl]-oxo-acetyl chloride |
| 68 | (2-Furan-2-yl-indolizin-3-yl)-oxo-acetyl chloride |
| 69 | (5-Methyl-2-phenyl-indolizin-3-yl)-oxo-acetyl chloride |
| 70 | (6-Methyl-2-phenyl-indolizin-3-yl)-oxo-acetyl chloride |
| 71 | (7-Methyl-2-phenyl-indolizin-3-yl)-oxo-acetyl chloride |
| 72 | (8-Methyl-2-phenyl-indolizin-3-yl)-oxo-acetyl chloride |
| 73 | (6-Methoxy-2-phenyl-indolizin-3-yl)-oxo-acetyl chloride |
| 74 | (6-Methyl-2-pyridin-3-yl-indolizin-3-yl)-oxo-acetyl chloride |
| 75 | Oxo-(2-o-tolyl-indolizin-3-yl)-acetyl chloride |
| 76 | Oxo-(2-m-tolyl-indolizin-3-yl)-acetyl chloride |
| 77 | Oxo-(2-p-tolyl-indolizin-3-yl)-acetyl chloride |
| 78 | [2-(3-Cyano-phenyl)-indolizin-3-yl]-oxo-acetyl chloride |
| 79 | [2-(3-Fluoro-phenyl)-indolizin-3-yl]-oxo-acetyl chloride |
| 80 | [2-(3-Chloro-phenyl)-indolizin-3-yl]-oxo-acetyl chloride |
| 81 | [2-(2-Chloro-phenyl)-indolizin-3-yl]-oxo-acetyl chloride |
| 82 | [2-(2,4-Difluoro-phenyl)-indolizin-3-yl]-oxo-acetyl chloride |
| 83 | [2-(2-Methoxy-phenyl)-indolizin-3-yl]-oxo-acetyl chloride |
| 84 | [2-(2-Chloro-pyridin-3-yl)-indolizin-3-yl]-oxo-acetyl chloride |

Reference Example 85

5-Amino-thiophene-3-carboxylic acid methyl ester a) Preparation of 3-thiophene carboxylic acid methyl ester To a solution of 3-thiophene carboxylic acid (2.0 g, 15.60 mmol) in methanol (30 ml) was added a catalytic amount of sulphuric acid (0.5 ml) and the reaction mixture was heated to reflux for 2 hr. The solvent was removed under reduced pressure and the residue was poured into ice-cold water and extracted with ethyl acetate. The organic layer was washed with water, concentrated and dried to give 3-thiophene carboxylic acid methyl ester (1.8 g, 81%).

b) Preparation of 5-nitro-thiophene-3-carboxylic acid methyl ester

To a solution of 3-thiophene carboxylic acid methyl ester (1.8 g, 12.68 mmol) in acetic acid (7.5 ml) was added a mixture of nitric acid (0.67 ml), acetic acid (7.5 ml) and acetic anhydride (4.3 ml) at 0-10° C. The reaction mixture was stirred at 40° C. for 1 hr and then poured into crushed ice. The solid was filtered, washed with cold water and dried. The compound was recrystallised using ether/hexane to give 5-nitro-thiophene-3-carboxylic acid methyl ester (1.0 g, 42%).

c) Preparation of 5-amino-thiophene-3-carboxylic acid methyl ester

To a solution of 5-nitro-thiophene-3-carboxylic acid methyl ester (0.5 g, 2.67 mmol) in aqueous acetic acid (5 ml) was added iron powder (1.04 g, 18.6 mmol) and the reaction mixture was heated to reflux for 3 hr. The reaction mixture was filtered and triethylamine was added to the filtrate. The compound was extracted with ethyl acetate and the organic layer was washed with water, concentrated and dried to yield crude compound. The compound was purified by silica gel column chromatography, using ethyl acetate/hexane as eluent, to yield 5-amino-thiophene-3-carboxylic acid methyl ester (0.1 g, 24%).

Reference Example 86

4-Amino-benzoyl chloride

Thionyl chloride (10 ml) was added to 4-aminobenzoic acid (1.0 g, 7.29 mmol) and the solution was heated to reflux for 16 hr. Thionyl chloride was removed under vacuum to yield 4-amino-benzoyl chloride (1.13 g, 100%).

Reference Example 87

4-Amino-benzamide

To an ice-cold solution of 4-amino-benzoyl chloride (0.38 g, 2.45 mmol) in tetrahydrofuran (2 ml) was added aqueous ammonia solution (15 ml). The reaction mixture was stirred at room temperature for 12 hr. The solvent was removed under vacuum, water added and the compound was extracted into ethyl acetate. The organic layer was dried and concentrated under vacuum. The crude compound was purified using silica gel column chromatography, using chloroform/methanol as eluent, to yield 4-amino-benzamide (0.1 g, 30%).

Reference Examples 88 to 89

The compounds set out below were prepared in the same way as in Example 87, using appropriate starting materials.

| Example | Compound |
|---------|----------|
| 88 | 4-Amino-N-methylbenzamide |
| 89 | 4-Amino-N,N-dimethylbenzamide |

Reference Example 90

2-Amino-2-methyl-propionic acid ethyl ester

2-Amino-2-methyl-propionic acid (1.0 g, 9.69 mmol) was dissolved in ethanol (15 ml) and cooled to 0° C. Thionyl chloride (1.7 g, 14.53 mmol, 1.5 eq) was added to the reaction mixture, which was then heated to reflux overnight. The solvent was evaporated and the residue was partitioned between water and ethyl acetate. The organic layer was concentrated and dried to give 2-amino-2-methyl-propionic acid ethyl ester (0.8 g, 63%). The crude compound was used in the next stage without purification.

Reference Example 91

The compound set out below was prepared in the same way as in Example 90, using appropriate starting materials.

| Example | Compound |
|---------|----------|
| 91 | 2-Amino-2-methyl-3-phenyl-propionic acid ethyl ester |

Reference Example 92

2-Allyloxy-4-fluoro-1-nitro-benzene

Allyl bromide (3.4 g, 28 mmol, 1.5 eq) was added to a mixture of 5-fluoro-2-nitro-phenol (3.0 g, 19 mmol, 1 eq) and potassium carbonate (5.2 g, 38 mmol, 2 eq) in anhydrous acetonitrile (25 ml) and the mixture was heated to reflux for 6 hr. The reaction mixture was filtered and washed with acetonitrile and the filtrate concentrated to dryness to give 2-allyloxy-4-fluoro-1-nitro-benzene (2.8 g, 75%). The crude compound was used in the next stage without purification.

Reference Example 93

2-Allyl-1-fluoro-3-methoxy-4-nitro-benzene a) Preparation of 2-allyl-3-fluoro-6-nitro-phenol 2-Allyloxy-4-fluoro-1-nitro-benzene (2.0 g, 10.1 mmol) was heated by microwave radiation at 180° C. for 30 min in a closed test tube. The crude compound was purified by column chromatography over silica gel using ethyl acetate and hexane (1:4) as eluent to give 2-allyl-3-fluoro-6-nitro-phenol (1.5 g, 70%).

b) Preparation of 2-allyl-1-fluoro-3-methoxy-4-nitro-benzene

Methyl iodide (5.3 g, 37.9 mmol, 5 eq) was added to a solution of 2-allyl-3-fluoro-6-nitro-phenol (1.5 g, 7.5 mmol) and potassium carbonate (2.1 g, 15.1 mmol, 2 eq) in anhydrous acetonitrile (20 ml) and the reaction mixture was heated to reflux for 6 hr. The reaction mixture was filtered and washed with acetonitrile and the filtrate was concentrated to dryness to yield 2-allyl-1-fluoro-3-methoxy-4-nitro-benzene (1.2 g, 75%). The crude compound was used in the next stage without purification.

Reference Example 94

2-Allyloxy-4-fluoro-phenylamine

Tin (II) chloride hydrate (8.5 g, 38 mmol, 5 eq) was added to a solution of 2-allyloxy-4-fluoro-1-nitro-benzene (1.5 g, 7.6 mmol) in ethyl acetate (20 ml) at room temperature and the mixture was stirred for 4 hr. The reaction mixture was neutralized with triethylamine and then partitioned between water and ethyl acetate. The organic layer was separated, dried over anhydrous sodium sulfate, filtered and concentrated to dryness to give 2-allyloxy-4-fluoro-phenylamine (0.6 g, 50%). The crude compound was used in the next stage without purification.

Reference Example 95

The compound set out below was prepared in the same way as in Example 94, using appropriate starting materials.

| Example | Compound |
|---------|----------|
| 95 | 3-allyl-4-fluoro-2-methoxy-phenylamine |

Reference Example 96

1-(4-Amino-phenyl)-ethanol

To a solution of 4-amino acetophenone (0.5 g, 3.7 mmol) in methanol (10 ml), was added sodium borohydride (0.27 g, 7.4 mmol, 2 eq) at 0° C. The reaction mixture was stirred for 3 hr at room temperature. The solvent was evaporated and water was added. The compound was extracted with ethyl acetate, then the organic layer was dried over anhydrous sodium sulfate, filtered and concentrated to dryness to yield pure 1-(4-amino-phenyl)-ethanol (0.4 g, 80%).

Reference Example 97

1-Methyl-5-nitro-1H-indole

To a solution of 5-nitro-1H-indole (2.0 g, 12.3 mmol) in acetone (20 ml), powdered potassium hydroxide (3.4 g, 60.7 mmol, 5 eq) was added followed by the addition methyl iodide (2.61 g, 18.5 mmol, 1.5 eq) at 0° C. The reaction mixture was heated to reflux for 10 hr. The solvent was evaporated and water was added. The compound was extracted with ethyl acetate, dried over anhydrous sodium sulphate, filtered and the organic layer was concentrated to dryness to yield 1-methyl-5-nitro-1H-indole (2.0 g, 92%). The crude compound was used in the next stage without purification.

Reference Example 98

1-Methyl-5-nitro-2,3-dihydro-1H-indole

To 5-nitroindoline (1.0 g, 6.1 mmol) in acetone (12 ml), powdered potassium hydroxide (1.7 g, 30.5 mmol, 5 eq) was added followed by the addition of methyl iodide (1.2 g, 9.1 mmol, 1.5 eq) at 0° C. The reaction mixture was stirred at room temperature overnight. The solvent was evaporated and water was added and the compound was extracted with ethyl acetate. The organic layer was dried over anhydrous sodium sulfate, filtered and concentrated to dryness to yield 1-methyl-5-nitro-2,3-dihydro-1H-indole (1.0 g, 92%). The crude compound was used in the next stage without purification.

Reference Example 99

1-Methyl-1H-indol-5-ylamine

To 1-methyl-5-nitro-1H-indole (0.5 g, 2.84 mmol) in ethyl acetate (10 ml), tin (II) chloride hydrate (2.5 g, 11.4 mmol, 4 eq) was added and the reaction mixture stirred overnight at room temperature. The reaction mixture was basified with aqueous sodium hydroxide solution (pH 8) and the compound extracted using ethyl acetate. The crude compound obtained was purified by column chromatography over silica gel using ethyl acetate/hexane (1:1) as eluent to give 1-methyl-1H-indol-5-ylamine (120 mg, 27%).

Reference Example 100

The compound set out below was prepared in the same way as in Example 99, using appropriate starting materials.

| Example | Compound |
|---------|----------|
| 100 | 1-Methyl-2,3-dihydro-1H-indol-5-ylamine |

Reference Example 101

2-(3-Amino-phenyl)-2-methyl-propionitrile a) Preparation of 2-methyl-2-(3-nitrophenyl)-propionitrile To an ice-cold slurry of 50% sodium hydride (2.17 g, 90.4 mmol) in anhydrous THF (15 ml), was slowly added a solution of (3-nitro-phenyl)-acetonitrile (2.2 g, 13.58 mmol) in anhydrous THF (5 ml). After 30 min, methyl iodide (6.67 ml, 107 mmol) was slowly added. The reaction mixture was allowed to warm to room temperature and stirred overnight. It was then quenched with ice-water. The compound was then extracted with ethyl acetate, the organic layer separated and washed with water, dried over anhydrous sodium sulphate, filtered and concentrated to oil. Column chromatography over silica gel by eluting with ethyl acetate/pet ether (5:95) gave 2-methyl-2-(3-nitrophenyl)-propionitrile (1.1 g, 43%) as a solid.

b) Preparation of 2-(3-amino-phenyl)-2-methyl-propionitrile

2-Methyl-2-(3-nitrophenyl)-propionitrile (0.5 g) was hydrogenated over 10% Pd—C in methanol (10 ml) at atmospheric pressure until no further gas uptake was observed. The reaction mixture was then filtered over celite and concentrated to oil. Column chromatography over silica gel by eluting with ethyl acetate/pet ether (1:9) gave 2-(3-aminophenyl)-2-methyl-propionitrile (0.35 g, 83%) as an oil.

Reference Example 102

2-(4-aminophenyl)-2-methyl propionitrile a) Preparation of 2-methyl-2-(4-nitro-phenyl)-propionitrile 40% sodium hydroxide solution (4 ml) was added to tetrabutyl-ammonium iodide (341 mg, 0.924 mmol) and a solution of (4-nitro-phenyl)-acetonitrile (1 g, 6.17 mmol) in dichloromethane (10 ml) under vigorous stirring. After 30 min, the reaction mixture was cooled to 0° C. and methyl iodide (1.536 ml, 24.67 mmol) was added. The reaction mixture was allowed to warm to room temperature and stirred overnight. The reaction mixture was diluted with dichloromethane and water, the organic layer separated and washed with water, dried and concentrated to oil. The crude compound was purified by column chromatography over silica gel using ethyl acetate/pet ether (1:9) as eluent to give 2-methyl-2-(4-nitro-phenyl)-propionitrile (0.6 g, 51%).

b) Preparation of 2-(4-aminophenyl)-2-methyl propionitrile 2-methyl-2-(4-nitro-phenyl)-propionitrile was dissolved in ethyl acetate (20 ml) and treated with stannous chloride dihydrate (3.52 g, 15.86 mmol). After stirring overnight at room temperature, the reaction mixture was basified with aqueous sodium carbonate. The organic layer was separated, washed with water, dried and concentrated to oil. The crude compound was purified by column chromatography over silica gel using ethyl acetate/pet ether (1:9) as eluent to give 2-(4-aminophenyl)-2-methyl propionitrile (0.45 g, 89%) as oil.

Reference Example 103

1-Methyl-2,3-dihydro-1H-indol-5-ylamine a) Preparation of 1-methyl-5-nitro-2,3-dihydro-1H-indole To a solution of 5-nitro-2,3-dihydro-1H-indole (1 g, 6.09 mmol) in acetone (12 ml) was added powdered potassium hydroxide (1.7 g, 30.45 mmol), followed by methyl iodide (1.2 g, 9.14 mmol) and stirred overnight at ambient temperature. The solvent was evaporated under vacuum to give a residue, to which water was added and the product extracted with ethyl acetate. Drying and concentration of the organic layer yielded 1-methyl-5-nitro-2,3-dihydro-1H-indole (1 g, 92%) as solid.

b) Preparation of 1-methyl-2,3-dihydro-1H-indol-5-ylamine

To a solution of 1-methyl-5-nitro-2,3-dihydro-1H-indole (0.2 g, 1.13 mmol) in ethyl acetate (12 ml) was added stannous chloride dihydrate (1.26 g, 5.6 mmol) and the reaction mixture was stirred overnight at room temperature. The reaction was then neutralized with aqueous sodium hydroxide solution. The organic layer was separated, washed with water, dried, and then concentrated to oil. The crude compound was purified by column chromatography over silica gel using ethyl acetate/pet ether (1:1) as eluent to give 1-methyl-2,3-dihydro-1H-indol-5-ylamine (0.12 g, 72%) as solid.

Reference Example 104

4-Thiomorpholin-4-yl-phenylamine a) Preparation of 4-(4-nitro-phenyl)-thiomorpholine A mixture of 1-chloro-4-nitro benzene (1.5 g, 9.5 mmol) and thiomorpholine (1.0 g, 9.7 mmol) was refluxed in n-butanol overnight. The solvent was evaporated under reduced pressure to give a residue, which on triturating with water gave a precipitate. The solid was filtered and washed thoroughly with water, followed by a small amount of pet ether to yield crude solid. Recrystallisation with ethanol yielded 4-(4-nitro-phenyl)-thiomorpholine (1.5 g, 71%).

b) Preparation of 4-thiomorpholin-4-yl-phenylamine

Stannous chloride dihydrate (10 g, 44.4 mmol) was added to a solution of 4-(4-nitro-phenyl)-thiomorpholine (2 g, 8.9 mmol) in ethyl acetate and stirred at room temperature for 4 hr. Water was added and the reaction mixture was neutralized with triethyl amine. The organic layer was dried over anhydrous sodium sulphate, filtered and concentrated under reduced pressure to yield 4-thiomorpholin-4-yl-phenylamine (1.2 g, 60%) as a solid.

Reference Example 105

4-(4-Methyl-piperazin-1-yl)-phenylamine a) Preparation of 1-methyl-4-(4-nitro-phenyl)-piperazine A mixture of 1-chloro-4-nitro benzene (3 g, 19 mmol), 1-methyl piperazine (2.28 g, 22.8 mmol) and ethyl-diisopropylamine (2 ml) in THF (20 ml) was stirred at room temperature for 12 hr. The reaction mixture was concentrated under reduced pressure to give a residue, which was then partitioned between dichloromethane and water. The organic layer was separated and evaporated under reduced pressure to give crude compound, which was purified by column chromatography over silica gel, using ethyl acetate as eluent, to yield 1-methyl-4-(4-nitro-phenyl)-piperazine (1.8 g, 44%) as solid.

b) Preparation of 4-(4-methyl-piperazin-1-yl)-phenylamine

1-Methyl-4-(4-nitro-phenyl)-piperazine (200 mg) was hydrogenated over 10% Pd—C (20 mg) in methanol (20 ml) at atmospheric pressure until no further gas uptake was observed. The reaction mixture was then filtered over celite and concentrated to give a crude solid. Column chromatography over silica gel using 4% methanol in dichloromethane gave 4-(4-methyl-piperazin-1-yl)-phenylamine (110 mg, 64%) as solid.

Reference Example 106

1-(4-Aminophenyl)-ethanone-O-methyl-oxime

To a solution of 4-amino acetophenone (650 mg, 4.8 mmol) and O-methyl-hydroxylamine hydrochloride (800 mg, 9.6 mmol) in ethanol (10 ml) was added a drop of conc. hydrochloric acid and the reaction was heated to reflux for 2 hr. The solvent was evaporated under reduced pressure and ethyl acetate was added, washed with water, dried over anhydrous sodium sulphate, and then filtered. Evaporation yielded 1-(4-aminophenyl)-ethanone-O-methyl-oxime (700 mg, 89%) as a solid.

Reference Example 107

The compound set out below was prepared in the same way as in Example 106, using appropriate starting materials.

| Example | Compound |
| --- | --- |
| 107 | 1-(4-Amino-phenyl)-ethanone oxime |

Reference Example 108

4-Methanesulphonyl-phenylamine a) Preparation of 1-methanesulfonyl-4-nitro-benzene MCPBA (5 g, 29.58 mmol) was added to a solution of 4-nitro-benzenethiol (1 g, 5.91 mmol) in dichloromethane (30 ml) at 0° C. and stirred at this temperature for 2 hr. Water was added, and then the organic layer was separated, dried and concentrated to oil. Column chromatography over silica gel using ethyl acetate/pet ether (15:85) as eluent gave 1-methanesulfonyl-4-nitro-benzene (750 mg, 63%) as a solid.

b) Preparation of 4-methanesulphonyl-phenylamine

A solution of 1-methanesulfonyl-4-nitro-benzene (500 mg, 2.48 mmol) in methanol (20 ml) was hydrogenated over 10% Pd—C (100 mg) at atmospheric pressure until no further gas uptake was observed. The reaction mixture was then filtered over celite and concentrated to give a residue, which was recrystallized from ethanol to yield 4-methanesulphonyl-phenylamine (276 mg, 65%) as solid.

Reference Example 109

Mixture of 1-methyl-1H-benzimidazol-5-yl amine and 3-methyl-3H-benzimidazol-5-yl amine Powdered potassium hydroxide (5.1 g, 92 mmol) was added to a solution of 6-nitro-1H-benzoimidazole (3 g, 18.4 mmol) in acetone (30 ml) in an ice bath and stirred for 30 min. Methyl iodide (1.7 ml, 27.6 mmol) was added and the reaction mixture was stirred for 3 hr at room temperature. The solvent was evaporated under reduced pressure to give a residue to which was added water and ethyl acetate. The organic layer was separated and washed with water, dried and concentrated to dryness to yield a mixture of 1-methyl-6-nitro-1H-benzoimidazole and 1-methyl-5-nitro-1H-benzoimidazole (3.2 g, 98%) as oil. The mixture of isomers (3.2 g, 18.07 mmol) was dissolved in methanol (50 ml) and hydrogenated at atmospheric pressure over 10% Pd—C (300 mg) until no further gas uptake was observed. The reaction mixture was then filtered over celite and concentrated to yield a mixture of 1-methyl-1H-benzimidazol-5-yl amine and 3-methyl-3H-benzimidazol-5-yl amine (2.53 g, 95%) as solid. The mixture was used in the next stage without purification.

Reference Example 110

(3-Aminophenoxy)-acetic acid ethyl ester a) Preparation of (3-nitrophenoxy)-acetic acid ethyl ester

Powdered sodium hydroxide (1 g, 28.77 mmol) was added to a solution of 3-nitro phenol (2 g, 14.35 mmol) in DMF (15 ml) and cooled in an ice-bath. Ethyl bromoacetate (3.2 ml, 28.77 mmol) was added, and the reaction mixture was heated at 90° C. for 7 hr. The reaction mixture was cooled and quenched with ice water. The product was extracted with ethyl acetate, washed with water and dried. Concentration under reduced pressure gave (3-nitrophenoxy)-acetic acid ethyl ester (2.2 g, 68%) as oil.

b) Preparation of (3-amino-phenoxy)-acetic acid ethyl ester

A solution of (3-nitrophenoxy)-acetic acid ethyl ester (500 mg, 2.22 mmol) in methanol (20 ml) was hydrogenated over 10% Pd—C (50 mg) at atmospheric pressure until no further gas uptake was observed. The reaction mixture was then filtered over celite and concentrated to yield a residue which was purified over neutral alumina using ethyl acetate-hexane to give (3-amino-phenoxy)-acetic acid ethyl ester (330 mg, 77%) as oil.

Reference Example 111

3-Amino-N-benzyl-N-methyl benzamide a) Preparation of N-benzyl-N-methyl-3-nitro-benzamide

To a solution of N-methyl benzylamine (600 mg, 5 mmol) and triethylamine (1.5 ml, 10 mmol) in anhydrous THF (15 ml), was slowly added 3-nitro benzoyl chloride (1 g, 5.4 mmol) and stirred overnight at room temperature. The solvent was evaporated to give a residue which was dissolved in ethyl acetate and washed thoroughly with water. The organic layer was dried and evaporated to give N-benzyl-N-methyl-3-nitro-benzamide (350 mg, 27%) as solid.

b) Preparation of 3-Amino-N-benzyl-N-methyl benzamide

To a solution of N-benzyl-N-methyl-3-nitro-benzamide (320 mg, 1.18 mmol) in ethyl acetate (10 ml) was added stannous chloride dihydrate (1.34 g, 5.95 mmol) and then stirred for 3 hr at room temperature. The reaction mixture was washed with dilute sodium hydroxide solution, then water. The organic layer was separated, dried and then evaporated to give 3-amino-N-benzyl-N-methyl-benzamide (270 mg, 95%) as solid.

Reference Example 112

1-(4-Aminophenyl)-piperidin-4-one a) Preparation of 1-(4-nitro-phenyl)-piperidin-4-one

To 4-piperidone hydrochloride (2.17 g, 16.0 mmol) in acetonitrile (20 ml) was added triethylamine (3.9 ml) and potassium carbonate (2.9 g, 21.0 mmol). After stirring for 20 min at room temperature, 1-fluoro-4-nitrobenzene (1 g, 7.09 mmol) was added and the reaction mixture was heated to reflux for 12 hr. The reaction mixture was then cooled and filtered and the filtrate concentrated under reduced pressure to give a residue. The residue was dissolved in water, extracted with ethyl acetate, dried and evaporated to give 1-(4-nitrophenyl)-piperidin-4-one (0.6 g, 38%).

b) Preparation of 1-(4-aminophenyl)-piperidin-4-one

A solution of 1-(4-nitro-phenyl)-piperidin-4-one (150 mg, 0.68 mmol) was dissolved in methanol (4 ml) and hydrogenated over 10% Pd/C (20 mg) at atmospheric pressure until no further gas uptake was observed. The reaction mixture was then filtered over celite and concentrated to yield the crude compound, which was purified by column chromatography using ethyl acetate/hexane (3:2) to give 1-(4-aminophenyl)-piperidin-4-one (75 mg, 57%).

Reference Example 113

4-(2-methyl-[1,3]-dioxolan-2-yl)-phenylamine a) Preparation of 2-methyl-2-(4-nitro-phenyl)-[1,3]dioxolane 4-nitro acetophenone (3 g, 18.18 mmol), ethylene glycol (1.35 g, 21.81 mmol) and p-toluene sulfonic acid (0.62 g) were taken in toluene and heated to reflux using a Dean-Stark water separator, until no more water was collected. The reaction mixture was cooled, water was added and the toluene layer separated. The aqueous layer was washed again with toluene and the toluene washings combined, dried and evaporated under reduced pressure to give 2-methyl-2-(4-nitrophenyl)-[1,3]dioxolane (2.7 g, 71%) as oil.

b) Preparation of 4-(2-methyl-[1,3]-dioxolan-2-yl)-phenylamine

To a solution of 2-methyl-2-(4-nitro-phenyl)-[1,3]dioxolane (100 mg, 0.48 mmol) in benzene (6 ml) was added iron powder (700 mg, 12.5 mmol) and 3 drops of water and then heated to reflux for 30 min. The reaction mixture was cooled, filtered and the filtrate was evaporated to give 4-(2-methyl-[1,3]-dioxolan-2-yl)-phenylamine (60 mg, 70%).

Reference Example 114

Diethyl-carbamic acid 3-aminophenyl ester a) Preparation of diethyl-carbamic acid-3-nitro-phenyl ester

To slurry of 50% sodium hydride (340 mg, 14.2 mmol) in anhydrous THF was added 3-nitrophenol (1 g, 7.1 mmol) at 0° C. After 10 min at 0-5° C., diethyl carbamyl chloride (1.5 g, 111.0 mmol) was added and the reaction mixture heated to reflux for 12 hr. The reaction mixture was cooled, ice water added, and filtered. The filtrate was concentrated to give the crude product, which was purified by column chromatography over silica gel, using hexane/ethyl acetate (85:15) as eluent to afford diethyl-carbamic acid-3-nitro-phenyl ester (300 mg, 17%).

b) Preparation of diethyl-carbamic acid 3-aminophenyl ester

To a solution of diethyl-carbamic acid-3-nitro-phenyl ester (300 mg, 1.26 mmol) in ethyl acetate (5 ml) was added stannous chloride dihydrate (1.08 g, 4.8 mmol) and stirred for 6 hr at room temperature. The reaction mixture was diluted with ethyl acetate and washed with sodium hydroxide solution. The organic layer was separated, washed with brine, dried and concentrated under reduced pressure to give diethyl-carbamic acid 3-aminophenyl ester (120 mg, 45%).

Reference Example 115

4-Oxazol-2-yl-phenylamine a) Preparation of 2-(4-nitro-phenyl)-oxazole

A mixture of p-nitro benzaldehyde (3 g, 19.8 mmol) and 2,2-diethoxy-ethylamine (2.64 g, 19.8 mmol) was heated at 100° C. for 2 hrs. The reaction mixture was cooled to room temperature and sulphuric acid (20 ml) was added. The resultant solution was added slowly to a mixture of phosphorus pentoxide (10 g) and sulphuric acid (3 ml) at 180° C. and the temperature was maintained for 30 min. The reaction mixture was cooled to room temperature and basified with saturated ammonium hydroxide solution. The resultant solid was filtered and recrystallised with ether to give 2-(4-nitro-phenyl)-oxazole (1 g, 26%).

b) Preparation of 4-oxazol-2-yl-phenylamine

A solution of 2-(4-nitro-phenyl)-oxazole (400 mg, 2.1 mmol) in methanol (10 ml) was hydrogenated over 10% Pd/C at 30 psi until no further gas uptake was observed. The reaction mixture was then filtered over celite and concentrated to give a residue which was purified by column chromatography using ethyl acetate/pet ether (3:7) to yield 4-oxazol-2-yl-phenylamine (300 mg, 89%).

Reference Example 116

The compound set out below was prepared in the same way as in Example 115, using appropriate starting materials.

| Example | Compound |
|---------|----------|
| 116 | (3-Oxazol-2-yl-phenylamine) |

Reference Example 117

N-Pyridin-2-yl-benzene-1,4-diamine a) Preparation of (4-nitro-phenyl)-pyridin-2-yl-amine To a solution of 4-nitro aniline (2 g, 14.48 mmol) and 2-bromo pyridine (3.43 g, 21.72 mmol) in DMSO (12 ml) was added powdered potassium hydroxide (3.24 g, 57.92 mmol) at room temperature and the reaction mixture was heated at 100° C. for 15 hr. The reaction mixture was diluted with ethyl acetate, and water added. The organic layer was separated, washed with brine, dried and evaporated to give crude material. Purification by column chromatography using hexane/ethyl acetate (96:4) yielded (4-nitro-phenyl)-pyridin-2-yl-amine (0.28 g, 9%).

b) Preparation of N-pyridin-2-yl-benzene-1,4-diamine

To a solution of (4-nitro-phenyl)-pyridin-2-yl-amine (280 mg, 1.3 mmol) in ethyl acetate (10 ml) was added stannous chloride dihydrate (1.17 g, 5.2 mmol) and stirred overnight at room temperature. The reaction mixture was diluted with ethyl acetate and washed with 10% sodium hydroxide solution. The organic layer was separated, washed with brine, dried and evaporated to dryness. Purification by column chromatography using ethyl acetate/hexane (2:3) yielded N-pyridin-2-yl-benzene-1,4-diamine (80 mg, 33%).

Reference Example 118

4-amino-2-methyl-N,N-dimethyl aniline a) Preparation of dimethyl-(2-methyl-4-nitro-phenyl)-amine To 2-methyl-4-nitro aniline (4 g, 26.2 mmol) in 30% sodium hydroxide solution (6 ml), cooled using an ice-bath, was added dimethyl sulphate (7.4 ml, 78.86 mmol). The reaction mixture was then heated to reflux for 6 hr. The reaction was then cooled to room temperature and adjusted to pH 9. The product was extracted with ethyl acetate, the organic layer washed with water, dried and evaporated. Purification by column chromatography using hexane/ethyl acetate (98:2) gave dimethyl-(2-methyl-4-nitro-phenyl)-amine (2 g, 43%).

b) Preparation of 4-amino-2-methyl-N,N-dimethyl aniline

A solution of dimethyl-(2-methyl-4-nitro-phenyl)-amine (0.49 g, 2.74 mmol) in methanol (10 ml) was hydrogenated over 10% Pd/C at 30 psi until no further gas uptake was observed. The reaction mixture was then filtered over celite and the filtrate evaporated to yield 4-amino-2-methyl-N,N-dimethyl aniline (0.3 g, 73%).

Reference Example 119

4-Dimethylaminomethyl-phenylamine a) Preparation of dimethyl-(4-nitro-benzyl)-amine To a mixture of 4-nitrobenzyl bromide (4 g, 18.5 mmol) and potassium carbonate (7.65 g, 55.5 mmol) in acetonitrile (50 ml) at 0-5° C. was added 40% aqueous dimethyl amine solution (1.5 eq). After 1 hr at room temperature, the solvent was evaporated; the crude material was dissolved in water and extracted with ethyl acetate. The organic layer was dried and concentrated to give dimethyl-(4-nitro-benzyl)-amine (2.8 g, 84%)

b) Preparation of 4-dimethylaminomethyl-phenylamine

To a solution of dimethyl-(4-nitro-benzyl)-amine (1 g, 5.55 mmol) in acetic acid (10 ml) was added activated iron powder (3 g) and the reaction mixture was stirred for 5 hr at 80° C. The reaction mixture was filtered; the filtrate diluted with water and neutralized with 10% sodium hydroxide solution. The product was extracted with ethyl acetate, the organic layer was dried and evaporated to give a residue. Purification by column chromatography using chloroform/methanol (98:2) to give 4-dimethylaminomethyl-phenylamine (0.7 g, 85%)

Reference Example 120

1-(4-Amino-phenyl)-pyrrolidine-2-carboxylic acid methyl ester a) Preparation of 1-(4-nitro-phenyl)-pyrrolidine-2-carboxylic acid A mixture of 1-chloro-4-nitrobenzene (3 g, 19 mmol), L-proline (2.19 g, 19.0 mmol) and triethylamine (10.6 ml, 76 mmol) were dissolved in DMSO (15 ml) then heated at 90° C. for 24 hr. The reaction mixture was concentrated under reduced pressure, the residue treated with water and extracted with dichloromethane. The organic layer was washed with brine, dried and evaporated to a residue. Purification by column chromatography using dichloromethane/methanol (97:3) gave 1-(4-nitro-phenyl)-pyrrolidine-2-carboxylic acid (0.9 g, 20%).

b) Preparation of 1-(4-nitro-phenyl)-pyrrolidine-2-carboxylic acid methyl ester

A solution of 1-(4-nitro-phenyl)-pyrrolidine-2-carboxylic acid (0.75 g, 3.17 mmol) in methanol (20 ml) was cooled to 0° C. Thionyl chloride (0.71 ml, 9.51 mmol) was added dropwise and then the reaction mixture was stirred at room temperature overnight. The reaction mixture was evaporated to dryness and then diluted with dichloromethane. The organic layer was washed with bicarbonate solution, water and dried. Evaporation to dryness yielded 1-(4-nitrophenyl)-pyrrolidine-2-carboxylic acid methyl ester (0.58 g, 73%).

c) Preparation of 1-(4-amino-phenyl)-pyrrolidine-2-carboxylic acid methyl ester

A solution of 1-(4-nitro-phenyl)-pyrrolidine-2-carboxylic acid methyl ester (0.55 g, 2.2 mmol) in methanol (15 ml) was hydrogenated over 10% Pd—C (50 mg) at 30 psi until no further gas uptake was observed. The reaction mixture was then filtered over celite and the filtrate evaporated to yield 1-(4-amino-phenyl)-pyrrolidine-2-carboxylic acid methyl ester (0.35 g, 72%).

Reference Example 121

4-(1H-Tetrazol-5-yl)-phenylamine

A mixture of p-amino benzonitrile (2 g, 16.9 mmol), triethylamine hydrochloride (3.49 g, 25.38 mmol) and sodium azide (1.65 g, 25.38 mmol) were taken in anhydrous toluene (20 ml) and heated to reflux for 24 hr. The reaction mixture was cooled to room temperature and neutralized with dilute hydrochloric acid. The resultant precipitate was filtered, washed with water then dried to give 4-(1H-tetrazol-5-yl)-phenylamine (1.2 g, 44%).

Reference Example 122

5-amino-2-dimethylamino-benzoic acid a) Preparation of 2-dimethylamino-5-nitro-benzoic acid 2-Chloro-5-nitrobenzoic acid (2 g, 9.9 mmol) was dissolved in of 8% sodium hydroxide solution (10 ml) at room temperature. 40% dimethyl amine aqueous solution (1.5 eq) was added and the reaction mixture was heated to reflux for 3 days. The reaction mixture was neutralized with dilute hydrochloric acid and extracted with ethyl acetate. The organic layer was dried and evaporated and the residue crystallized with ether/pet ether to give 2-dimethylamino-5-nitro-benzoic acid (1.14 g, 57%).

b) Preparation of 5-amino-2-dimethylamino-benzoic acid

A solution of 2-dimethylamino-5-nitro-benzoic acid (200 mg, 0.95 mmol) in methanol (15 ml) was hydrogenated over 10% Pd/C (20 mg) at 30 psi until no further gas uptake was observed. The reaction mixture was then filtered over celite and the filtrate evaporated to yield the crude product. Recrystallisation using pet. ether yielded 5-amino-2-dimethylamino-benzoic acid (110 mg, 70%).

Reference Example 123

3-(2-Dimethylamino-ethoxy)-phenylamine a) Preparation of dimethyl-[2-(3-nitro-phenoxy)-ethyl]-amine 3-Nitro phenol (1 g, 7.19 mmol) was added to a solution of potassium hydroxide (1.6 g, 28.76 mmol) in anhydrous DMSO (6 ml) at room temperature. After 30 min, (2-chloroethyl)-dimethyl-amine hydrochloride (1.03 g, 7.19 mmol) was added and the reaction mixture was heated at 80-90° C. for 12 hr. The reaction mixture was cooled to room temperature and diluted with ice water. The product was extracted with toluene and the organic layer was washed with 5% sodium hydroxide solution, then brine and dried. Evaporation under reduced pressure gave dimethyl-[2-(3-nitro-phenoxy)-ethyl]-amine (600 mg, 40%) as oil.

b) Preparation of 3-(2-dimethylamino-ethoxy)-phenylamine

A solution of dimethyl-[2-(3-nitro-phenoxy)-ethyl]-amine (500 mg, 2.38 mmol) in methanol (20 ml) was hydrogenated over 10% Pd—C at 30 psi until no further gas uptake was observed. The reaction mixture was then filtered over celite and concentrated to yield 3-(2-dimethylamino-ethoxy)-phenylamine (365 mg, 85%) as viscous oil.

Reference Example 124

1-(4-Amino-phenyl)-propan-2-one a) Preparation of (4-nitro-phenyl)-acetyl chloride To mixture of p-nitrophenylacetic acid (1 g, 5.5 mmol) in benzene (10 ml) was added thionyl chloride (0.8 ml) at room temperature. The reaction mixture was heated to reflux for 12 hr and then cooled. The excess thionyl chloride and benzene were removed in vacuo to obtain (4-nitro-phenyl)-acetyl chloride (1 g, 91%).

b) Preparation of 2-[2-(4-nitro-phenyl)-acetyl]-malonic acid diethyl ester $MgCl_2$ (0.34 g) was added to a mixture of diethylmalonate (0.91 ml) and triethylamine (1.74 ml) in dry toluene (12 ml).

The mixture was then stirred for 1 hr at room temperature. (4-nitro-phenyl)-acetyl chloride (1 g) was then added at 0° C. under nitrogen atmosphere and stirring was continued for 1 hr at room temperature. Conc. hydrochloric acid (3 ml) was added to quench the reaction. The reaction mixture was partitioned between ethyl acetate and water. The organic layer was separated, washed with water and brine, dried over sodium sulphate, filtered and then evaporated to afford 2-[2-(4-nitro-phenyl)-acetyl]-malonic acid diethyl ester (1.4 g, 86%).

c) Preparation of 1-(4-nitro-phenyl)-propan-2-one

2-[2-(4-Nitro-phenyl)-acetyl]-malonic acid diethyl ester (1.4 g) was taken up in a mixture of DMSO (8 ml) and water (4 ml) and heated at 150° C. with stirring for 10 hr. The product was extracted with ethyl acetate (50 ml). The organic layer was washed with water, aqueous sodium bicarbonate solution and brine. The organic layer was then dried over sodium sulphate, filtered and evaporated. Purification by column chromatography over silica gel using ethyl acetate and hexane (6:94) as eluent yielded 1-(4-nitro-phenyl)-propan-2-one (160 mg, 24%).

d) Preparation of 1-(4-amino-phenyl)-propan-2-one 1-(4-nitro-phenyl)-propan-2-one (150 mg) was dissolved in methanol (5 ml) and then Pd/C (50 mg) was added. The resulting reaction mixture was stirred for 10 hr at room temperature under hydrogen pressure. The reaction mixture was filtered over celite and the filtrate evaporated. Purification by column chromatography over silica gel using ethyl acetate and hexane (1:9) as eluent gave 1-(4-amino-phenyl)-propan-2-one (60 mg, 48%).

Reference Example 125

1-(5-Amino-2-methoxy-phenyl)-ethanone a) Preparation of 2-methoxy-5-nitro-benzoic acid 2-Chloro-5-nitro-benzoic acid (3 g, 14 mmol) was added to a solution of freshly prepared sodium methoxide (from sodium (1.36 g, 56 mmol) in dry methanol (15 ml)) and the reaction was heated to reflux for 12 hr. Methanol was evaporated and the reaction mass diluted with water (25 ml). Conc hydrochloric acid was added until the pH was ~2. The reaction mixture was stirred at room temperature for 30 min, then the precipitate was filtered and washed with water. Drying at 60-70° C. yielded 2-methoxy-5-nitro benzoic acid (2.4 g, 81%).

b) Preparation of 2-methoxy-5-nitro-benzoyl chloride

2-Methoxy-5-nitro benzoic acid (500 mg, 2.5 mmol) was heated to reflux with thionyl chloride (5 ml) for 4 hr. The excess thionyl chloride was evaporated under reduced pressure to yield 2-methoxy-5-nitro-benzoyl chloride (0.55 g, 100%), which was used as such for the next step.

c) 1-(2-Methoxy-5-nitro-phenyl)-ethanone

Anhydrous magnesium chloride (150 mg, 1.6 mmol) was added to a solution of diethyl malonate (440 mg, 2.76 mmol) and triethylamine (670 mg, 6.5 mmol) in dry toluene (10 ml) at room temperature under inert atmosphere. After stirring for 1 hr, the reaction was cooled to 0° C. and 2-methoxy-5-nitro benzoyl chloride (550 mg, 2.3 mmol) was added. The reaction mixture was allowed to attain room temperature then stirred for 30 min before adding 6N hydrochloric acid (15 ml). The organic layer was separated, washed with water and dried. Concentration under reduced pressure gave a residue to which was added 1:1 DMSO-water (10 ml). The mixture was heated to 140° C. for 2 hr, then cooled to RT and diluted with ethyl acetate (50 ml). The organic layer was washed successively with water, bicarbonate solution, and brine, then dried. Evaporation under reduced pressure gave 1-(2-Methoxy-5-nitro-phenyl)-ethanone (350 mg, 70%) as a solid.

d) Preparation of 1-(5-amino-2-methoxy-phenyl)-ethanone

A solution of 1-(2-methoxy-5-nitro-phenyl)-ethanone (350 mg, 1.8 mmol) in methanol (20 ml) was hydrogenated over 10% Pd—C (70 mg) at atmospheric pressure until no further absorption of gas took place. The reaction mixture was then filtered over celite and the filtrate concentrated under reduced pressure to give 1-(5-amino-2-methoxy-phenyl)-ethanone (250 mg, 85%) as a solid.

Reference Example 126

N-Thiazol-2-yl-benzene-1,4-diamine a) Preparation of (4-nitro-phenyl)-thiazol-2-yl-amine A mixture of 2-aminothiazole (2 g, 19.97 mmol), 1-fluoro-4-nitro benzene (2.25 g, 15.97 mmol) and potassium carbonate (11 g, 79.88 mmol) were heated together in DMF (15 ml) at 100-110° C. for 12 h. The reaction mixture was cooled to room temperature and filtered. The filtrate was diluted with ethyl acetate and washed repeatedly with water and finally with brine. The organic layer was dried and concentrated to give a residue, which was chromatographed over silica gel using 0-14% EtOAc-hexane to isolate a mixture of (4-nitro-phenyl)-thiazol-2-yl amine and bis-(4-nitrophenyl)-thiazol-2-yl-amine (1 g, 22.6%), as solid. The mixture was used in the next step without further purification.

b) Preparation of N-thiazol-2-yl-benzene-1,4-diamine

Zinc powder (1.2 g, 18.46 mmol) was added to a solution of 400 mg of a mixture of (4-nitro-phenyl)-thiazol-2-yl-amine and bis-(4-nitrophenyl)-thiazol-2-yl amine in acetic acid (8 ml) and then heated at 65-70° C. for 2 hr. The reaction mixture was concentrated under reduced pressure and diluted with ethyl acetate. The organic layer was washed with dilute sodium hydroxide solution, then water, brine and dried. Evaporation yielded a crude mixture which was chromatographed over silica gel using 1% methanol in chloroform to give N-thiazol-2-yl-benzene-1,4-diamine (75 mg, 21.7%), as a solid.

Reference Example 127

6-(2,2,3,3-Tetrafluoro-propoxy)-pyridin-3-ylamine a) Preparation of 5-nitro-2-(2,2,3,3-tetrafluoro-propoxy)-pyridine 1,1,2,2-Tetrafluoro-3-iodo propane (0.5 g, 2 mmol) was added to a mixture of 5-nitro-2-hydroxy pyridine (860 mg, 6.1 mmol) and potassium carbonate (1.4 g, 10 mmol) in DMF (10 ml) and the reaction heated at reflux for 6 hr. The reaction mixture was cooled to room temperature and filtered. The filtrate was diluted with ethyl acetate (50 ml), washed successively with bicarbonate solution, water, brine, and dried. Concentration to dryness yielded 5-nitro-2-(2,2,3,3-tetrafluoro-propoxy)pyridine (394 mg, 75%) as an oil.

b) Preparation of 6-(2,2,3,3-tetrafluoro propoxy)-pyridin-3-ylamine

A solution of 5-nitro-2-(2,2,3,3-tetrafluoro-propoxy)pyridine (1.5 g, 0.6 mmol) in methanol (30 ml) was hydrogenated over 10% Pd—C (150 mg) at atmospheric pressure until no further gas was absorbed. The reaction mixture was filtered over celite and the filtrate concentrated to dryness to yield 6-(2,2,3,3-tetrafluoro propoxy)-pyridin-3-ylamine (600 mg, 50%) as solid.

Reference Example 128

4-(2,2,3,3-Tetrafluoro-propoxy)-phenylamine a) Preparation of 1-nitro-4-(2,2,3,3-tetrafluoro propoxy)benzene To a solution of 4-nitro phenol (860 mg, 6.1 mmol) in DMF (10 ml) was added potassium carbonate (1.4 g, 10 mmol) and 1,1,2,2-tetrafluoro-3-iodo-propane (500 mg, 2 mmol). The reaction mixture was heated at 100-110° C. for 6 hr, then cooled to room temperature and filtered. The filtrate was diluted with ethyl acetate (100 ml), then washed once with 5% sodium hydroxide solution, several times with water, and finally brine. The organic layer was then dried over anhydrous sodium sulfate, filtered, and evaporated to dryness to give 1-nitro-4-(2,2,3,3-tetrafluoro-propoxy)-benzene (360 mg, 68%) as solid.

b) Preparation of 4-(2,2,3,3-tetrafluoro propoxy) aniline

Iron powder (1.3 g, 23.2 mol) was added to a solution of 1-nitro-4-(2,2,3,3-tetrafluoro-propoxy)-benzene (600 mg, 2.4 mmol) in acetic acid (4 ml) and heated at 50-60° C. for 1 hr. The reaction mixture was filtered hot over celite and washed with ethyl acetate. The filtrate was washed with water, 5% sodium hydroxide solution, brine and then dried over anhydrous sodium sulfate. The filtrate was evaporated to dryness to yield 4-(2,2,3,3-tetrafluoro-propoxy)-phenylamine (300 mg, 56.7%) as solid.

Reference Example 129

4-(3,5-Dimethyl-isoxazol-4-yl)-phenylamine a) Preparation of 3-(4-nitrophenyl)-pentane-2,4-dione A mixture of pentane-2,4-dione (4.41 g, 40 mmol), 1-iodo-4-nitrobenzene (5 g, 20 mmol) and potassium carbonate (11 g, 80 mmol) were heated in DMSO (15 ml) at 120° C. for 3 hr. The reaction mixture was cooled to room temperature, diluted with water (100 ml), and then extracted with ethyl acetate. The organic layer was washed with water, brine and dried. Evaporation gave a residue which was chromatographed over silica gel eluting with ethyl acetate/pet ether (5:95) to give 3-(4-nitrophenyl)-pentane-2,4-dione (2.67 g, 60%) as solid.

b) Preparation of 3,5-dimethyl-4-(4-nitrophenyl)-isoxazole

A mixture of 3-(4-nitrophenyl)-pentane-2,4-dione (50 mg, 0.22 mmol), hydroxylamine hydrochloride (15 mg, 0.22 mmol) and pyridine (17 mg, 0.22 mmol) in ethanol (10 ml) was heated to reflux overnight. Evaporation of the solvent gave a residue which was partitioned between water and ethyl acetate. The organic layer was separated, washed with water, then brine and dried. Evaporation to dryness yielded 3,5-dimethyl-4-(4-nitrophenyl)-isoxazole (44 mg, 90%) as solid.

c) Preparation of 4-(3,5-dimethyl-isoxazol-4-yl)-phenylamine

To a solution of 3,5-dimethyl-4-(4-nitrophenyl)-isoxazole (50 mg, 0.22 mmol) in ethanol (10 ml) was added tin (52 mg, 0.44 mmol), followed by dropwise addition of concentrated hydrochloric acid (1 ml) and the reaction was stirred at room temperature for 2 hr. The reaction mixture was filtered and the filtrate evaporated to dryness. The resultant residue was diluted with water, basified with saturated bicarbonate solution, then extracted with ethyl acetate. The organic layer was washed with water, dried and concentrated to dryness to yield 4-(3,5-dimethyl-isoxazol-4-yl)-phenylamine (40 mg, 90%) as solid.

Reference Example 130

N2,N2-Dipropyl-pyridine-2,5-diamine a) Preparation of (5-nitro-pyridin-2-yl)-dipropylamine N,N-dipropylamine (3 ml, 22 mmol) was added to a solution of 2-chloro-5-nitropyridine (500 mg, 3.15 mmol) in acetonitrile (7 ml) and heated to reflux overnight. The reaction mixture was diluted with water and extracted with ethyl acetate. The organic layer was then washed with water, brine and dried. Evaporation to dryness gave (5-nitro-pyridin-2-yl)-dipropylamine (630 mg, 90%) as oil.

b) Preparation of N2,N2-dipropyl-pyridine-2,5-diamine

A solution of (5-nitro-pyridin-2-yl)-dipropylamine (630 mg, 2.82 mmol) in methanol (10 ml) was hydrogenated over 10% Pd—C (130 mg) at room temperature and atmospheric pressure until no further gas absorption occurred. The reaction mixture was filtered over celite and the filtrate was concentrated to an oil. Purification by column chromatography over silica gel using 0-20% ethyl acetate in pet ether yielded N2,N2-dipropyl-pyridine-2,5-diamine (336 mg, 46.5%) as oil.

Reference Example 131

N1,N1-Diethyl-2-methyl-benzene-1,4-diamine a) Preparation of diethyl-(2-methyl-4-nitro-phenyl)-amine 3N Sulfuric acid (20 ml) was added dropwise to a stirred solution of 20% acetaldehyde (10 ml, 45.45 mmol) in THF (10 ml) at 0° C. After 15 min, this mixture was added to a solution of 2-methyl-4-nitro aniline (1 g, 6.6 mmol) in THF (10 ml). Sodium borohydride (1.5 g, 40.5 mmol) was added portion-wise and the reaction mixture was stirred at room temperature for 2 hr. The reaction mixture was then diluted with water (60 ml), basified with sodium carbonate, and extracted with ethyl acetate. The organic layer was washed with water, brine and dried. Evaporation to dryness gave a residue, which was chromatographed over silica gel using 0-3% ethyl acetate in pet ether to give diethyl-(2-methyl-4-nitro-phenyl)-amine (720 mg, 50%) as oil.

b) Preparation of N1,N1-Diethyl-2-methyl-benzene-1,4-diamine

A solution of diethyl-(2-methyl-4-nitro-phenyl)-amine (340 mg, 1.634 mmol) in methanol (10 ml) was hydrogenated over 10% Pd—C (50 mg) at room temperature and atmospheric pressure until no more gas absorption occurred. The reaction mixture was filtered over celite and the filtrate concentrated to dryness to give N1,N1-Diethyl-2-methyl-benzene-1,4-diamine (243 mg, 46.5%) as oil.

Reference Example 132

4-Oxazol-5-yl-phenylamine a) Preparation of 5-(4-nitro-phenyl)-oxazole

A mixture of 4-nitro benzaldehyde (500 mg, 3.31 mmol), tosylmethyl isocyanide (640 mg, 3.31 mmol) and potassium carbonate (1.37 g, 9.9 mmol) were heated to reflux in methanol (10 ml) for 2 hr. Evaporation of the solvent yielded a residue, which was diluted with water and extracted into ethyl acetate. The organic layer was washed with water and brine, dried and concentrated under reduced pressure to yield 5-(4-nitro-phenyl)-oxazole (600 mg, 95%) as solid.

b) Preparation of 4-oxazol-5-yl-phenylamine

To a solution of 5-(4-nitro-phenyl)-oxazole (500 mg, 2.6 mmol) in ethanol (10 ml) was added tin (620 mg, 5.2 mmol), followed by dropwise addition of concentrated hydrochloric acid (1 ml) and then the reaction was stirred at room temperature for 2 hr. The reaction mixture was filtered and the filtrate evaporated to dryness. The resultant residue was diluted with water (10 ml), basified with saturated bicarbonate solution, then extracted with ethyl acetate. The organic layer was separated, washed with water, dried and concentrated to dryness to yield 4-oxazol-5-yl-phenylamine (380 mg, 90%) as solid.

Reference Example 133

N1,N1-Dimethyl-2-oxazol-2-yl-benzene-1,4-diamine a) Preparation of 2-dimethylamino-5-nitro-benzoic acid 2-Chloro-5-nitro benzoic acid (2 g, 10 mmol) was added to 40% dimethylamine aq. solution (20 ml) at room temperature and then heated at 60-65° C. for 3 hr. The reaction mixture was chilled to 0° C. and acidified with dilute acetic acid. The mixture was then extracted with ethyl acetate, and the organic layer washed with water, then brine and dried. Evaporation of the solvent yielded 2-dimethylamino-5-nitro-benzoic acid (2.1 g, 91%), as a solid.

b) Preparation of N-(2,2-dimethoxyethyl)-2-dimethylamino-5-nitro benzamide

A mixture of 2-dimethylamino-5-nitro benzoic acid (300 mg, 1.42 mmol) and thionyl chloride (0.41 ml 5.7 mmol) in dry chloroform (5 ml) was heated to reflux for 3 hr. The excess thionyl chloride was evaporated to give a residue, which was then dissolved in acetone (2 ml). This was then added dropwise to a mixture of 2,2-dimethoxy-ethylamine (0.15 ml, 1.44 mmol) and sodium bicarbonate (120 mg, 1.44 mmol) in 2:1 acetone-water (12 ml) at 0° C. and stirred overnight at room temperature. The reaction mixture was diluted with water and extracted with ethyl acetate. The organic layer was washed with water and then brine, dried and concentrated to yield of N-(2,2-dimethoxyethyl)-2-dimethylamino-5-nitro benzamide (313 mg, 79%) as solid.

c) Preparation of dimethyl-(4-nitro-2-oxazol-2-yl-phenyl)-amine

A solution of N-(2,2-dimethoxyethyl)-2-dimethylamino-5-nitro benzamide (1.1 g, 3.7 mmol) in methane sulphonic acid (5 ml) was added to a slurry of phosphorus pentoxide (2.6 g, 18.51 mmol) in methane sulphonic acid (15 ml) and refluxed overnight. The reaction mixture was cooled to room temperature, poured onto ice water, and then basified with dilute sodium hydroxide and extracted with ethyl acetate. The organic layer was washed with brine, dried and concentrated to a residue. Purification by chromatography over silica gel using 5-30% ethyl acetate/pet ether gave dimethyl-(4-nitro-2-oxazol-2-yl-phenyl)-amine (150 mg, 60%) as solid.

d) Preparation of N1,N1-dimethyl-2-oxazol-2-yl-benzene-1,4-diamine

Iron powder (0.15 g, 2.574 mmol) was added to a solution of dimethyl-(4-nitro-2-oxazol-2-yl-phenyl)-amine (200 mg, 0.86 mmol) in acetic acid (3 ml) and stirred overnight at room temperature. The reaction mixture was poured into ice water and basified with dilute sodium hydroxide solution and then filtered. The filtrate was extracted with ethyl acetate, and the organic layer was washed with water, then brine and dried. Evaporation to dryness gave N1,N1-dimethyl-2-oxazol-2-yl-benzene-1,4-diamine (150 mg, 88.2%) as oil.

Reference Example 134

4-Thiazol-2-yl-phenylamine a) Preparation of 2-phenyl-thiazole

To a solution of thiobenzamide (1 g, 7.3 mmol) in THF (10 ml) was added a solution of 2-bromo-1,1-diethoxy-ethane (1.4 g, 7.3 mmol) in THF (5 ml) and the reaction was heated at reflux overnight. The reaction mixture was cooled to room temperature and diluted with water (50 ml). The solution was basified with dilute sodium hydroxide and extracted with ethyl acetate: pet ether (1:4). The organic layer was then washed with water, brine and dried. Evaporation gave a residue which was purified by column chromatography over silica gel using EtOAc/pet ether as eluent to give 2-phenyl thiazole (400 mg, 34%) as solid.

b) Preparation of 2-(4-nitrophenyl)-thiazole

A solution of 2-phenyl thiazole (200 mg, 1.24 mmol) in conc. sulphuric acid (0.5 ml) was cooled to 0° C. The nitrating mixture (made up of 0.5 ml of conc. nitric acid and 0.5 ml of conc. sulfuric acid) was added dropwise and stirred at 0° C. for 1 hr. The reaction was quenched with ice water and basified with sodium hydroxide solution. The resultant precipitate was filtered and washed with water. Purification by column chromatography over silica gel using EtOAc/pet ether gave 2-(4-nitrophenyl) thiazole (150 mg, 58.6%) as solid.

c) Preparation of 4-thiazol-2-yl-phenylamine

Iron powder (0.5 g, 8.92 mmol) was added portion wise to a solution of 2-(4-nitrophenyl)-thiazole (200 mg, 0.97 mmol) in acetic acid (5 ml) and stirred at room temperature for 2 hr. The reaction mixture was diluted with water, basified with dilute sodium hydroxide, filtered and the filtrate was extracted with ethyl acetate. The organic layer was washed with water, brine and dried. Evaporation of the solvent yielded 4-thiazol-2-yl-phenylamine (150 mg, 88%) as solid.

Example 135

2-Oxo-2-(2-phenyl-indolizin-3-yl)-N-p-tolyl-acetamide

To an ice-cold solution of oxo-(2-phenyl-indolizin-3-yl)-acetyl chloride (0.5 g, 1.76 mmol) and p-toluidine (0.21 g, 1.94 mmol) in dichloromethane (10 ml) was added triethylamine (0.5 ml, 3.52 mmol). The reaction mixture was stirred at room temperature for 1 hr. The solvent was evaporated under vacuum. Column chromatography on silica gel afforded 2-oxo-2-(2-phenyl-indolizin-3-yl)-N-p-tolyl-acetamide (0.4 g, 65%).

Examples 136 to 293

The compounds set out below were prepared in the same way as in Example 135, using appropriate starting materials.

| Example | Compound |
|---|---|
| 136 | 2-Oxo-N-phenyl-2-(2-phenyl-indolizin-3-yl)-acetamide |
| 137 | N-(2-Methoxy-phenyl)-2-oxo-2-(2-phenyl-indolizin-3-yl)-acetamide |
| 138 | N-(3-Methoxy-phenyl)-2-oxo-2-(2-phenyl-indolizin-3-yl)-acetamide |
| 139 | N-(4-Methoxy-phenyl)-2-oxo-2-(2-phenyl-indolizin-3-yl)-acetamide |
| 140 | 4-[2-Oxo-2-(2-phenyl-indolizin-3-yl)-acetylamino]-benzoic acid methyl ester |
| 141 | 3-[2-Oxo-2-(2-phenyl-indolizin-3-yl)-acetylamino]-benzoic acid methyl ester |
| 142 | 2-[2-Oxo-2-(2-phenyl-indolizin-3-yl)-acetylamino]-benzoic acid methyl ester |
| 143 | 4-[2-Oxo-2-(2-phenyl-indolizin-3-yl)-acetylamino]-benzoic acid propyl ester |
| 144 | 4-[2-Oxo-2-(2-phenyl-indolizin-3-yl)-acetylamino]-benzoic acid butyl ester |
| 145 | N-(2,4-Dimethoxy-phenyl)-2-oxo-(2-phenyl-indolizin-3-yl)-acetamide |
| 146 | N-(6-Methoxy-pyridin-3-yl)-2-oxo-2-(2-phenyl-indolizin-3-yl)-acetamide |
| 147 | N-(4-Methoxy-phenyl)-2-oxo-2-(2-pyridin-3-yl-indolizin-3-yl)-acetamide |
| 148 | N-(4-Methoxy-phenyl)-2-oxo-2-(2-thiophen-2-yl-indolizin-3-yl)-acetamide |
| 149 | N-(2,4-Dimethoxy-phenyl)-2-[2-(4-fluoro-phenyl)-indolizin-3-yl]-2-oxo-acetamide |
| 150 | N-(4-Cyano-phenyl)-2-oxo-2-(2-phenyl-indolizin-3-yl)-acetamide |
| 151 | 2-Oxo-2-(2-phenyl-indolizin-3-yl)-N-pyridin-2-yl-acetamide |
| 152 | 2-Oxo-2-(2-phenyl-indolizin-3-yl)-N-pyridin-3-yl-acetamide |
| 153 | N-Methyl-4-[2-oxo-2-(2-phenyl-indolizin-3-yl)-acetylamino]-benzamide |
| 154 | 5-[2-Oxo-2-(2-phenyl-indolizin-3-yl)-acetylamino]-thiophene-3-carboxylic acid methyl ester |
| 155 | 2-[2-(4-Fluoro-phenyl)-indolizin-3-yl]-N-(4-methoxy-phenyl)-2-oxo-acetamide |
| 156 | 2-[2-(4-Fluoro-phenyl)-indolizin-3-yl]-2-oxo-N-p-tolyl-acetamide |
| 157 | 2-[2-(4-Fluoro-phenyl)-indolizin-3-yl]-N-(6-methoxy-pyridin-3-yl)-2-oxo-acetamide |
| 158 | 2-Oxo-2-(2-phenyl-indolizin-3-yl)-N-pyridin-4-yl-acetamide |
| 159 | 4-[2-Oxo-2-(2-phenyl-indolizin-3-yl)-acetylamino]-benzoic acid |
| 160 | N,N-Dimethyl-4-[2-oxo-2-(2-phenyl-indolizin-3-yl)-acetylamino]-benzamide |
| 161 | 4-[2-Oxo-2-(2-phenyl-indolizin-3-yl)-acetylamino]-benzamide |
| 162 | N-(4-Methoxy-phenyl)-2-oxo-2-(2-pyridin-4-yl-indolizin-3-yl)-acetamide |
| 163 | N-(4-Methoxy-phenyl)-2-oxo-2-(2-pyridin-2-yl-indolizin-3-yl)-acetamide |
| 164 | 2-(2-Furan-2-yl-indolizin-3-yl)-N-(4-methoxy-phenyl)-2-oxo-acetamide |
| 165 | 2-Oxo-2-(2-thiophen-2-yl-indolizin-3-yl)-N-p-tolyl-acetamide |
| 166 | N-(2,4-Dimethoxy-phenyl)-2-oxo-2-(2-thiophen-2-yl-indolizin-3-yl)-acetamide |
| 167 | N-(6-Methoxy-pyridin-3-yl)-2-oxo-2-(2-thiophen-2-yl-indolizin-3-yl)-acetamide |
| 168 | 2-(2-Furan-2-yl-indolizin-3-yl)-2-oxo-N-p-tolyl-acetamide |
| 169 | N-(2,4-Dimethoxy-phenyl)-2-(2-furan-2-yl-indolizin-3-yl)-2-oxo-acetamide |
| 170 | 2-(2-Furan-2-yl-indolizin-3-yl)-N-(6-methoxy-pyridin-3-yl)-2-oxo-acetamide |
| 171 | 2-Oxo-2-(2-pyridin-4-yl-indolizin-3-yl)-N-p-tolyl-acetamide |
| 172 | N-(2,4-Dimethoxy-phenyl)-2-oxo-2-(2-pyridin-4-yl-indolizin-3-yl)-acetamide |
| 173 | 2-Oxo-2-(2-pyridin-3-yl-indolizin-3-yl)-N-p-tolyl-acetamide |
| 174 | N-(2,4-Dimethoxy-phenyl)-2-oxo-2-(2-pyridin-3-yl-indolizin-3-yl)-acetamide |
| 175 | 2-Oxo-2-(2-pyridin-2-yl-indolizin-3-yl)-N-p-tolyl-acetamide |
| 176 | N-(2,4-Dimethoxy-phenyl)-2-oxo-2-(2-pyridin-2-yl-indolizin-3-yl)-acetamide |
| 177 | 4-[2-Oxo-2-(2-phenyl-indolizin-3-yl)-acetoxy]-benzoic acid methyl ester |
| 178 | N-Cyclohexyl-2-oxo-2-(2-phenyl-indolizin-3-yl)-acetamide |
| 179 | N-Methyl-2-oxo-2-(2-phenyl-indolizin-3-yl)-acetamide |
| 180 | N-Isopropyl-2-oxo-2-(2-phenyl-indolizin-3-yl)-acetamide |
| 181 | N-(2-Methoxy-ethyl)-2-oxo-2-(2-phenyl-indolizin-3-yl)-acetamide |
| 182 | N-Benzyl-2-oxo-2-(2-phenyl-indolizin-3-yl)-acetamide |
| 183 | N,N-Dimethyl-2-oxo-2-(2-phenyl-indolizin-3-yl)-acetamide |
| 184 | 1-(2-Phenyl-indolizin-3-yl)-2-piperidin-1-yl-ethane-1,2-dione |
| 185 | N-(2-Methoxy-ethyl)-2-oxo-2-(2-pyridin-3-yl-indolizin-3-yl)-acetamide |
| 186 | N-Methyl-2-oxo-N-phenyl-2-(2-phenyl-indolizin-3-yl)-acetamide |
| 187 | N-Methyl-2-oxo-N-phenyl-2-(2-pyridin-3-yl-indolizin-3-yl)-acetamide |
| 188 | 2-(5-Methyl-2-phenyl-indolizin-3-yl)-2-oxo-N-p-tolyl-acetamide |
| 189 | N-(6-Methoxy-pyridin-3-yl)-2-(5-methyl-2-phenyl-indolizin-3-yl)-2-oxo-acetamide |
| 190 | 2-(6-Methyl-2-phenyl-indolizin-3-yl)-2-oxo-N-p-tolyl-acetamide |

| Example | Compound |
|---|---|
| 191 | 2-(7-Methyl-2-phenyl-indolizin-3-yl)-2-oxo-N-p-tolyl-acetamide |
| 192 | N-(6-Methoxy-pyridin-3-yl)-2-(6-methyl-2-phenyl-indolizin-3-yl)-2-oxo-acetamide |
| 193 | N-(6-Methoxy-pyridin-3-yl)-2-(7-methyl-2-phenyl-indolizin-3-yl)-2-oxo-acetamide |
| 194 | N-(6-Methoxoy-pyridin-3-yl)-2-(8-methyl-2-phenyl-indolizin-3-yl)-2-oxo-acetamide |
| 195 | 2-(6-Methoxy-2-phenyl-indolizin-3-yl)-N-(6-methoxy-pyridin-3-yl)-2-oxo-acetamide |
| 196 | 2-(6-Methoxy-2-phenyl-indolizin-3-yl)-2-oxo-N-p-tolyl-acetamide |
| 197 | N-(4-Chloro-phenyl)-2-oxo-2-(2-pyridin-3-yl-indolizin-3-yl)-acetamide |
| 198 | N-(4-Fluoro-phenyl)-2-oxo-2-(2-pyridin-3-yl-indolizin-3-yl)-acetamide |
| 199 | 2-(6-Methyl-2-pyridin-3-yl-indolizin-3-yl)-2-oxo-N-p-tolyl-acetamide |
| 200 | N-(4-Fluoro-phenyl)-2-oxo-2-(2-phenyl-indolizin-3-yl)-acetamide |
| 201 | N-(2-Fluoro-phenyl)-2-oxo-2-(2-phenyl-indolizin-3-yl)-acetamide |
| 202 | 2-Oxo-2-(2-phenyl-indolizin-3-yl)-N-o-tolyl-acetamide |
| 203 | N-(4-Dimethylamino-phenyl)-2-oxo-2-(2-phenyl-indolizin-3-yl)-acetamide |
| 204 | N-(4-Bromo-phenyl)-2-oxo-2-(2-phenyl-indolizin-3-yl)-acetamide |
| 205 | N-(4-Acetyl-phenyl)-2-oxo-2-(2-phenyl-indolizin-3-yl)-acetamide |
| 206 | 2-Oxo-2-(2-phenyl-indolizin-3-yl)-N-m-tolyl-acetamide |
| 207 | N-(2-Chloro-phenyl)-2-oxo-2-(2-phenyl-indolizin-3-yl)-acetamide |
| 208 | 2-[2-Oxo-2-(2-phenyl-indolizin-3-yl)-acetylamino]-benzoic acid ethyl ester |
| 209 | N-(4-Fluoro-phenyl)-2-[2-(4-fluoro-phenyl)-indolizin-3-yl]-2-oxo-acetamide |
| 210 | N-(4-Chloro-phenyl)-2-[2-(4-fluoro-phenyl)-indolizin-3-yl]-2-oxo-acetamide |
| 211 | N-(2-Fluoro-phenyl)-2-oxo-2-(2-pyridin-3-yl-indolizin-3-yl)-acetamide |
| 212 | 2-Oxo-2-(2-pyridin-3-yl-indolizin-3-yl)-N-(4-trifluoromethyl-phenyl)-acetamide |
| 213 | 2-Oxo-2-(2-pyridin-3-yl-indolizin-3-yl)-N-o-tolyl-acetamide |
| 214 | N-(4-Bromo-phenyl)-2-oxo-2-(2-pyridin-3-yl-indolizin-3-yl)-acetamide |
| 215 | 2-Oxo-2-(2-pyridin-3-yl-indolizin-3-yl)-N-m-tolyl-acetamide |
| 216 | N-(2-Chloro-phenyl)-2-oxo-2-(2-pyridin-3-yl-indolizin-3-yl)-acetamide |
| 217 | N-(4-Acetyl-phenyl)-2-oxo-2-(2-pyridin-3-yl-indolizin-3-yl)-acetamide |
| 218 | 1-(2,3-Dihydro-indol-1-yl)-2-(2-phenyl-indolizin-3-yl)-ethane-1,2-dione |
| 219 | N-(4-Methanesulfonylamino-phenyl)-2-oxo-2-(2-phenyl-indolizin-3-yl)-acetamide |
| 220 | N-(3,5-Dichloro-phenyl)-2-oxo-2-(2-phenyl-indolizin-3-yl)-acetamide |
| 221 | N-[4-(Cyano-dimethyl-methyl)-phenyl]-2-oxo-2-(2-phenyl-indolizin-3-yl)-acetamide |
| 222 | 2-Oxo-2-(2-phenyl-indolizin-3-yl)-N-(3,4,5-trimethoxy-phenyl)-acetamide |
| 223 | 2-Oxo-2-(2-pyridin-3-yl-indolizin-3-yl)-N-(3-trifluoromethyl-phenyl)-acetamide |
| 224 | N-(2,4-Dichloro-phenyl)-2-oxo-2-(2-pyridin-3-yl-indolizin-3-yl)-acetamide |
| 225 | N-[4-(Cyano-dimethyl-methyl)-phenyl]-2-oxo-2-(2-pyridin-3-yl-indolizin-3-yl)-acetamide |
| 226 | 2-Oxo-2-(2-pyridin-3-yl-indolizin-3-yl)-N-(3,4,5-trimethoxy-phenyl)-acetamide |
| 227 | N-(3,5-Dichloro-phenyl)-2-oxo-2-(2-pyridin-3-yl-indolizin-3-yl)-acetamide |
| 228 | N-[3-(Cyano-dimethyl-methyl)-phenyl]-2-oxo-2-(2-phenyl-indolizin-3-yl)-acetamide |
| 229 | N-(6-Dimethylamino-pyridin-3-yl)-2-oxo-2-(2-phenyl-indolizin-3-yl)-acetamide |
| 230 | N-(4-Dimethylamino-phenyl)-2-oxo-2-(2-pyridin-3-yl-indolizin-3-yl)-acetamide |
| 231 | N-[3-(Cyano-dimethyl-methyl)-phenyl]-2-oxo-2-(2-pyridin-3-yl-indolizin-3-yl)-acetamide |
| 232 | N-(4-Methoxy-phenyl)-2-oxo-2-(2-o-tolyl-indolizin-3-yl)-acetamide |
| 233 | N-(4-Methoxy-phenyl)-2-oxo-2-(2-m-tolyl-indolizin-3-yl)-acetamide |
| 234 | N-(4-Methoxy-phenyl)-2-(8-methyl-2-phenyl-indolizin-3-yl)-2-oxo-acetamide |
| 235 | 2-[2-(3-Chloro-phenyl)-indolizin-3-yl]-N-(4-methoxy-phenyl)-2-oxo-acetamide |
| 236 | 2-[2-(3-Cyano-phenyl)-indolizin-3-yl]-N-(4-methoxy-phenyl)-2-oxo-acetamide |
| 237 | N-(4-Methoxy-phenyl)-2-(5-methyl-2-phenyl-indolizin-3-yl)-2-oxo-acetamide |
| 238 | N-(4-Methoxy-phenyl)-2-oxo-2-(2-p-tolyl-indolizin-3-yl)-acetamide |
| 239 | N-(4-Methoxy-phenyl)-2-(6-methoxy-2-phenyl-indolizin-3-yl)-2-oxo-acetamide |
| 240 | N-[3-(2-Dimethylamino-ethoxy)-phenyl]-2-oxo-2-(2-phenyl-indolizin-3-yl)-acetamide |
| 241 | N-(3-Methyl-3H-benzoimidazol-5-yl)-2-oxo-2-(2-phenyl-indolizin-3-yl)-acetamide and N-(1-Methyl-1H-benzoimidazol-5-yl)-2-oxo-2-(2-phenyl-indolizin-3-yl)-acetamide |
| 242 | N-(4-Dimethylamino-phenyl)-2-(6-methoxy-2-phenyl-indolizin-3-yl)-2-oxo-acetamide |
| 243 | N-(4-{1-[(E/Z)-Methoxyimino]-ethyl}-phenyl)-2-oxo-2-(2-phenyl-indolizin-3-yl)-acetamide |
| 244 | N-(2,4-Difluoro-phenyl)-2-[2-(3-fluoro-phenyl)-indolizin-3-yl]-2-oxo-acetamide |
| 245 | 2-[2-(3-Cyano-phenyl)-indolizin-3-yl]-N-(2,4-difluoro-phenyl)-2-oxo-acetamide |
| 246 | N-(5-Chloro-2-methyl-phenyl)-2-oxo-2-(2-phenyl-indolizin-3-yl)-acetamide |
| 247 | N-(2-Allyloxy-4-fluoro-phenyl)-2-oxo-2-(2-phenyl-indolizin-3-yl)-acetamide |
| 248 | 2-Methyl-2-[2-oxo-2-(2-phenyl-indolizin-3-yl)-acetylamino]-propionic acid ethyl ester |
| 249 | 2-Methyl-2-[2-oxo-2-(2-phenyl-indolizin-3-yl)-acetylamino]-3-phenyl-propionic acid ethyl ester |
| 250 | N-(4-{1-[(E/Z)-Hydroxyimino]-ethyl}-phenyl)-2-oxo-2-(2-phenyl-indolizin-3-yl)-acetamide |
| 251 | N-(4-Morpholin-4-yl-phenyl)-2-oxo-2-(2-phenyl-indolizin-3-yl)-acetamide |
| 252 | N-(4-Isopropyl-phenyl)-2-oxo-2-(2-phenyl-indolizin-3-yl)-acetamide |
| 253 | N-(6-Dimethylamino-pyridin-3-yl)-2-oxo-2-(2-pyridin-3-yl-indolizin-3-yl)-acetamide |
| 254 | N-(3-Allyl-4-fluoro-2-methoxy-phenyl)-2-oxo-2-(2-phenyl-indolizin-3-yl)-acetamide |
| 255 | N-[4-(1-Hydroxy-ethyl)-phenyl]-2-oxo-2-(2-phenyl-indolizin-3-yl)-acetamide |
| 256 | N-(1-Methyl-1H-indol-5-yl)-2-oxo-2-(2-phenyl-indolizin-3-yl)-acetamide |
| 257 | N-(4-Methanesulfonyl-phenyl)-2-oxo-2-(2-phenyl-indolizin-3-yl)-acetamide |
| 258 | 2-Oxo-2-(2-phenyl-indolizin-3-yl)-N-(4-thiomorpholin-4-yl-phenyl)-acetamide |
| 259 | 2-Oxo-2-(2-phenyl-indolizin-3-yl)-N-(2,3,4-trimethyl-phenyl)-acetamide |
| 260 | 2-Oxo-2-(2-phenyl-indolizin-3-yl)-N-(4-pyrrolidin-1-yl-phenyl)-acetamide |
| 261 | N-(1-Methyl-2,3-dihydro-1H-indol-5-yl)-2-oxo-2-(2-phenyl-indolizin-3-yl)-acetamide |
| 262 | N-[4-(4-Methyl-piperazin-1-yl)-phenyl]-2-oxo-2-(2-phenyl-indolizin-3-yl)-acetamide |
| 263 | N-Benzyl-N-methyl-3-[2-oxo-2-(2-phenyl-indolizin-3-yl)-acetylamino]-benzamide |
| 264 | N-[4-(2-Methyl-[1,3]dioxolan-2-yl)-phenyl]-2-oxo-2-(2-phenyl-indolizin-3-yl)-acetamide |
| 265 | N-(2,4-Difluoro-phenyl)-2-[2-(2,4-difluoro-phenyl)-indolizin-3-yl]-2-oxo-acetamide |
| 266 | Diethyl-carbamic acid 3-[2-oxo-2-(2-phenyl-indolizin-3-yl)-acetylamino]-phenyl ester |
| 267 | N-(3-Acetyl-phenyl)-2-oxo-2-(2-phenyl-indolizin-3-yl)-acetamide |

-continued

| Example | Compound |
|---|---|
| 268 | N-(4-Oxazol-2-yl-phenyl)-2-oxo-2-(2-phenyl-indolizin-3-yl)-acetamide |
| 269 | N-(2,4-Difluoro-phenyl)-2-[2-(2-methoxy-phenyl)-indolizin-3-yl]-2-oxo-acetamide |
| 270 | 2-Oxo-2-(2-phenyl-indolizin-3-yl)-N-[4-(pyridin-2-ylamino)-phenyl]-acetamide |
| 271 | 2-Oxo-2-(2-phenyl-indolizin-3-yl)-N-[4-(1H-tetrazol-5-yl)-phenyl]-acetamide |
| 272 | 2-Oxo-N-[4-(4-oxo-piperidin-1-yl)-phenyl]-2-(2-phenyl-indolizin-3-yl)-acetamide |
| 273 | N-(4-Dimethylamino-3-methyl-phenyl)-2-oxo-2-(2-phenyl-indolizin-3-yl)-acetamide |
| 274 | 2-Dimethylamino-5-[2-oxo-2-(2-phenyl-indolizin-3-yl)-acetylamino]-benzoic acid |
| 275 | 1-{4-[2-Oxo-2-(2-phenyl-indolizin-3-yl)-acetylamino]-phenyl}-pyrrolidine-2-carboxylic acid methyl ester |
| 276 | 2-Oxo-2-(2-phenyl-indolizin-3-yl)-N-[4-(pyrimidin-2-ylamino)-phenyl]-acetamide |
| 277 | 2-[2-(2-Chloro-phenyl)-indolizin-3-yl]-N-(2,4-difluoro-phenyl)-2-oxo-acetamide |
| 278 | N-(4-Dimethylaminomethyl-phenyl)-2-oxo-2-(2-phenyl-indolizin-3-yl)-acetamide |
| 279 | N-(3-Hydroxy-phenyl)-2-oxo-2-(2-phenyl-indolizin-3-yl)-acetamide |
| 280 | {3-[2-Oxo-2-(2-phenyl-indolizin-3-yl)-acetylamino]-phenoxy}-acetic acid ethyl ester |
| 281 | N-(4-Chloro-phenyl)-2-oxo-2-(2-phenyl-indolizin-3-yl)-acetamide |
| 282 | N-(3-Acetyl-4-methoxy-phenyl)-2-oxo-2-(2-phenyl-indolizin-3-yl)-acetamide |
| 283 | 2-[2-(2-Methyl-pyridin-3-yl)-indolizin-3-yl]-2-oxo-N-[4-(2,2,3,3-tetrafluoro-propoxy)-phenyl]-acetamide |
| 284 | 2-Oxo-N-[4-(2-oxo-propyl)-phenyl]-2-(2-phenyl-indolizin-3-yl)-acetamide |
| 285 | 2-Oxo-2-(2-phenyl-indolizin-3-yl)-N-[4-(thiazol-2-ylamino)-phenyl]-acetamide |
| 286 | 2-Oxo-N-[6-(2,2,3,3-tetrafluoro-propoxy)-pyridin-3-yl]-2-(2-o-tolyl-indolizin-3-yl)-acetamide |
| 287 | N-[4-(3,5-Dimethyl-isoxazol-4-yl)-phenyl]-2-oxo-2-(2-phenyl-indolizin-3-yl)-acetamide |
| 288 | N-(3-Oxazol-2-yl-phenyl)-2-oxo-2-(2-phenyl-indolizin-3-yl)-acetamide |
| 289 | N-(6-Dipropylamino-pyridin-3-yl)-2-oxo-2-(2-phenyl-indolizin-3-yl)-acetamide |
| 290 | N-(4-Diethylamino-3-methyl-phenyl)-2-oxo-2-(2-phenyl-indolizin-3-yl)-acetamide |
| 291 | N-(4-Oxazol-5-yl-phenyl)-2-oxo-2-(2-phenyl-indolizin-3-yl)-acetamide |
| 292 | N-(4-Dimethylamino-3-oxazol-2-yl-phenyl)-2-oxo-2-(2-phenyl-indolizin-3-yl)-acetamide |
| 293 | 2-Oxo-2-(2-phenyl-indolizin-3-yl)-N-(4-thiazol-2-yl-phenyl)-acetamide |

Example 294

{3-[2-Oxo-2-(2-phenyl-indolizin-3-yl)-acetylamino]-phenoxy}-acetic acid

To a solution of {3-[2-Oxo-2-(2-phenyl-indolizin-3-yl)-acetylamino]-phenoxy}-acetic acid ethyl ester (0.4 g, 0.90 mmol) in methanol (3 ml) was added lithium hydroxide (38 mg, 1.8 mmol) and a few drops of water. The reaction mixture was stirred at room temperature for 30 min, and then concentrated under reduced pressure. The reaction mixture was diluted with water (10 ml) and adjusted to pH 3 with 2N hydrochloric acid. The product was extracted with ether and the organic layer dried over sodium sulphate, filtered, then evaporated to dryness to yield {3-[2-oxo-2-(2-phenyl-indolizin-3-yl)-acetylamino]-phenoxy}-acetic acid (0.2 g, 53%).

Example 295

2-[(E/Z)-2-Dimethylamino-ethoxyimino]-N-(4-methoxy-phenyl)-2-(2-phenyl-indolizin-3-yl)-acetamide a) Preparation of diphenyl-methanone O-(2-dimethylaminoethyl)-oxime To a solution of diphenyl-methanone oxime (2 g, 10 mmol) and (2-chloro-ethyl)-dimethyl-amine hydrochloride (1.5 g, 10.4 mmol) in DMSO (20 ml) was added powdered potassium hydroxide (800 mg, 14.3 mmol) and the reaction mixture stirred overnight. The reaction mixture was diluted with water and then extracted with ethyl acetate. The organic layer was washed thoroughly with water and brine, then dried over anhydrous sodium sulphate and filtered. Concentration of the organic layer under reduced pressure gave diphenyl-methanone O-(2-dimethylaminoethyl)-oxime (700 mg, 26%) as a solid.

b) Preparation of O-(2-dimethylaminoethyl)-hydroxylamine hydrochloride

To diphenyl-methanone O-(2-dimethylaminoethyl)-oxime (700 mg, 2.61 mmol) was added conc. hydrochloric acid (10 ml) and the reaction was heated to reflux overnight. The reaction mixture was cooled and washed with ether. The aqueous layer was then concentrated under reduced pressure to yield O-(2-dimethylaminoethyl)-hydroxylamine hydrochloride (200 mg, 44%) as a white solid.

c) Preparation of 2-[(E/Z)-2-Dimethylamino-ethoxyimino]-N-(4-methoxy-phenyl)-2-(2-phenyl-indolizin-3-yl)-acetamide (mixture of isomers)

To a mixture of N-(4-methoxy-phenyl)-2-oxo-2-(2-phenyl-indolizin-3-yl)-acetamide (500 mg, 1.35 mmol) and O-(2-dimethylaminoethyl)-hydroxylamine hydrochloride (1 g, 5.65 mmol) in ethanol was added powdered potassium hydroxide (750 mg, 13.5 mmol) and the reaction mixture was heated to reflux overnight. The reaction mixture was concentrated to give a residue which was diluted with water and extracted with dichloromethane. The organic layer was washed with water and brine, dried over anhydrous sodium sulfate, filtered and evaporated to a solid. Column chromatography over silica gel using acetone as eluent gave 2-[(E/Z)-2-dimethylamino-ethoxyimino]-N-(4-methoxy-phenyl)-2-(2-phenyl-indolizin-3-yl)-acetamide (120 mg, 20%) as a solid.

Example 296

The compound set out below was prepared in the same way as in Example 295, using the same stepwise process and the appropriate starting materials.

| Example | Compound |
|---|---|
| 296 | 2-[(E/Z)-3-Dimethylamino-propoxyimino]-N-(4-methoxy-phenyl)-2-(2-phenyl-indolizin-3-yl)-acetamide |

Example 297

4-[1-(4-Methoxy-phenylcarbamoyl)-1-(2-phenyl-indolizin-3-yl)-meth-(E/Z)-ylideneaminooxy]-butyric acid a) Preparation of 4-benzhydrilideneaminoxy-butyric acid ethyl ester

To a solution of diphenyl-methanone oxime (4 g, 20.3 mmol) in acetonitrile (25 ml) was added anhydrous potassium carbonate (5.6 g, 40.6 mmol) and the reaction stirred for 30 min at room temperature. Ethyl-4-bromo butyrate (4 g, 19.2 mmol) was added and the reaction mixture was heated to reflux overnight. The reaction mixture was cooled to room temperature, filtered and washed with acetonitrile. Concentration of the filtrate gave a crude compound, which was purified by column chromatography using ethyl acetate/pet ether (4:96) to give 4-benzhydrilideneaminoxy-butyric acid ethyl ester (4.08 g, 63%) as oil.

b) Preparation of 4-aminooxy-butyric acid methyl ester hydrochloride

A mixture of 4-benzhydrilideneaminoxy-butyric acid ethyl ester (4.08 g, 13.1 μmol) and 6N hydrochloric acid was heated to reflux for 2 hr. The reaction mixture was cooled to room temperature and washed with ether. The aqueous layer separated and concentrated to dryness to give a residue, to which methanol (20 ml) was added. Evaporation yielded 4-aminooxy-butyric acid methyl ester hydrochloride (1.5 g, 54%) as a solid.

c) Preparation of 4-[1-(4-Methoxy-phenylcarbamoyl)-1-(2-phenyl-indolizin-3-yl)-meth-(E/Z)-ylideneaminooxy]-butyric acid (mixture of isomers)

To a solution of 4-aminooxy-butyric acid methyl ester hydrochloride (600 mg, 2.9 mmol) and N-(4-methoxy-phenyl)-2-oxo-2-(2-phenyl-indolizin-3-yl)-acetamide (400 mg, 1.08 mmol) in ethanol was added powdered potassium hydroxide (600 mg, 10.5 mmol) and the reaction heated overnight at reflux. The reaction mixture was concentrated to a residue and water was added and acidified to pH 6 with dilute hydrochloric acid. The product was extracted with dichloromethane and washed with water, dried and concentrated to give a residue. Purification by column chromatography using ethyl acetate as eluent yielded 4-[1-(4-methoxy-phenylcarbamoyl)-1-(2-phenyl-indolizin-3-yl)-meth-(E/Z)-ylideneaminooxy]-butyric acid (mixture of isomers) (45 mg, 9%) as a solid.

Example 298

2-[(E/Z)-Methoxyimino]-N-(4-methoxy-phenyl)-2-(2-phenyl-indolizin-3-yl)-acetamide A mixture of N-(4-methoxy-phenyl)-2-oxo-2-(2-phenyl-indolizin-3-yl)-acetamide (0.8 g, 2.16 mmol), methoxylamine hydrochloride (330 mg, 4 mmol, 2 eq) and sodium hydroxide (0.8 g, 10 eq) in methanol/water was heated to reflux overnight. The reaction mixture was concentrated to give a residue which was diluted with water and extracted with dichloromethane. The organic layer was washed with water and brine, dried over anhydrous sodium sulfate, filtered and evaporated to yield 2-[(E/Z)-methoxyimino]-N-(4-methoxy-phenyl)-2-(2-phenyl-indolizin-3-yl)-acetamide (50 mg, 6%).

Example 299

1-Methyl-4-{4-[2-oxo-2-(2-phenyl-indolizin-3-yl)-acetylamino]-phenyl}-thiomorpholin-1-ium iodide Methyl iodide (1.6 g, 11.26 mmol) was added to a solution of 2-oxo-2-(2-phenyl-indolizin-3-yl)-N-(4-thiomorpholin-4-yl-phenyl)-acetamide (1 g, 2.2 mmol) in anhydrous THF (25 ml) and then heated to reflux for 8 hr. The reaction mixture was cooled and the resultant precipitate was filtered and washed with cold THF. The solid was dried at 40° C. yielding 1-methyl-4-{4-[2-oxo-2-(2-phenyl-indolizin-3-yl)-acetylamino]-phenyl}-thiomorpholin-1-ium iodide (600 mg, 58%).

Examples 300 to 307 are available commercially and have also been shown to have anti-fungal activity in accordance with the present invention.

Example 300

1-Morpholin-4-yl-2-(2-phenyl-indolizin-3-yl)-ethane-1,2-dione

Example 301

1-Azepan-1-yl-2-(2-phenyl-indolizin-3-yl)-ethane-1,2-dione

Example 302

N-Ethyl-2-oxo-N-phenyl-2-(2-phenyl-indolizin-3-yl)-acetamide

Example 303

N-(1,5-Dimethyl-3-oxo-2-phenyl-2,3-dihydro-1-pyrazol-4-yl)-2-oxo-2-(2-phenyl-indolizin-3-yl)-acetamide

Example 304

2-Oxo-2-(2-phenyl-indolizin-3-yl)-N-(4-trifluoromethyl-phenyl)-acetamide

Example 305

N-(2,4-Dichloro-phenyl)-2-oxo-2-(2-phenyl-indolizin-3-yl)-acetamide

Example 306

2-Oxo-2-(2-phenyl-indolizin-3-yl)-N-(3-trifluoromethyl-phenyl)-acetamide

Example 307

2-Oxo-2-(2-phenyl-indolizin-3-yl)-N-(4-piperidin-1-yl-phenyl)-acetamide

Analytical data for compounds representative of Examples 135 to 299

| Example | NMR Data | MS Spectrum |
|---|---|---|
| 135 | ¹H (CDCl₃, 300 MHz) 9.76 (1H, d); 8.24 (1H bs); 7.62 (1H, d); 7.48-7.45 (2H, m); 7.36-7.31 (4H, m); 7.12 (2H, d); 7.08 (2H, d); 7.08-6.98 (1H, m); 6.67 (1H, s); 2.31 (3H, s) | 355 (M + H) |
| 136 | ¹H (CDCl₃, 300 MHz) 9.75 (1H, d); 8.28 (1H, bs); 7.61 (1H, d); 7.47-7.44 (2H, m); 7.33-7.19 (8H, m); 7.11-7.06 (1H, m); 7.02-6.97 (1H, m); 6.65 (1H, s) | 340 (M + H) |
| 141 | ¹H (CDCl₃, 300 MHz) 9.76 (2H, d); 8.31 (1H, bs); 7.77-7.72 (2H, m); 7.61 (1H, d); 7.52 (1H, m); 7.46-7.43 (2H, m); 7.34-7.27 (5H, m); 7.00 (1H, t); 6.65 (1H, s); 3.92 (3H, s) | 399 (M + H) |
| 142 | ¹H (CDCl₃, 300 MHz) 11.82 (1H, bs); 9.89 (1H, d); 8.02 (1H, m); 7.95 (1H, d); 7.60 (1H, d); 7.45-7.20 (7H, m); 7.10-7.04 (1H, m); 7.01-6.96 (1H, m); 7.01-6.96 (1H, m); 6.63 (1H, s); 3.97 (3H, s) | 399 (M + H) |
| 144 | ¹H (CDCl₃, 300 MHz) 9.76 (1H, d); 8.45 (1H, bs); 7.95 (2H, d); 7.61 (1H, d); 7.42 (1H, m); 7.35-7.26 (6H, m); 7.00 (1H, t); 6.66 (1H, s); 4.30 (2H, t); 1.79-1.70 (2H, m); 1.51-1.41 (2H, m); 1.00 (3H, t) | 441 (M + H) |
| 145 | ¹H (CDCl₃, 300 MHz) 9.79 (1H, d); 8.63 (1H, bs); 7.56 (2H, m); 7.44 (2H, m); 7.27 (4H, m); 6.98 (1H, m); 6.64 (1H, s); 6.46 (1H, d); 6.33 (1H, dd); 3.89 (3H, s); 3.78 (3H, s) | 401 (M + H) |
| 146 | ¹H (CDCl₃, 300 MHz) 9.76 (1H, d); 8.14 (1H, bs); 7.96 (1H, d); 7.61 (1H, d); 7.45 (3H, m); 7.31 (4H, m); 7.01 (1H, m); 6.65 (1H, s); 6.63 (1H, d); 3.90 (3H, s) | 372 (M + H) |
| 147 | ¹H (CDCl₃, 300 MHz) 9.77 (1H, d); 8.68 (1H, s); 8.55 (1H, d); 8.35 (1H, bs); 7.78 (1H, d); 7.64 (1H, d); 7.33 (1H, t); 7.28 (1H, m); 7.19 (2H, d); 7.04 (1H, t); 6.81 (2H, d); 6.67 (1H, s); 3.78 (3H, s) | 372 (M + H) |
| 148 | ¹H (CDCl₃, 300 MHz) 9.69 (1H, d); 8.19 (1H, bs); 7.59 (1H, d); 7.32 (1H, m); 7.28 (3H, m); 7.11 (1H, m); 6.99 (2H, m); 6.85 (2H, m); 6.69 (1H, s); 3.80 (3H, s) | 377 (M + H) |
| 149 | ¹H (CDCl₃, 300 MHz) 9.79 (1H, dd); 8.66 (1H, bs); 6.46 (1H, d); 7.60 (1H, d); 7.40 (2H, m); 7.30 (1H, m); 6.97 (3H, m); 6.61 (1H, s); 6.48 (1H, d); 6.38 (1H, dd); 3.89 (3H, s); 3.80 (3H, s) | 419 (M + H) |
| 150 | ¹H (CDCl₃, 300 MHz) 9.75 (1H, d); 8.49 (1H, bs); 7.63 (1H, d); 7.55 (1H, d); 7.41 (2H, m); 7.37-7.26 (6H, m); 7.03 (1H, m); 6.67 (1H, s) | 365 (M + H) |
| 152 | ¹H (CDCl₃, 300 MHz) 9.77 (1H, d); 8.38 (3H, bs); 7.62 (2H, m); 7.43 (2H, m); 7.36-7.28 (4H, m); 7.17 (1H, m); 7.02 (1H, m); 6.66 (1H, s) | 342 (M + H) |
| 155 | ¹H (CDCl₃, 300 MHz) 9.74 (1H, d); 8.21 (1H, bs); 7.60 (1H, d); 7.40 (2H, m); 7.31 (1H, m); 7.17 (2H, m); 7.00 3H, m); 6.82 (2H, m); 6.61 (1H, s); 3.79 (3H, s) | 389 (M + H) |
| 156 | ¹H (CDCl₃, 300 MHz) 9.74 (1H, d); 8.26 (1H, bs); 7.60 (1H, d); 7.40 (2H, m); 7.30 (1H, t); 7.11 (2H, d); 7.09 (2H, d); 6.99 (3H, m); 6.61 (1H, s); 2.31 (3H, s) | 373 (M + H) |
| 157 | ¹H (CDCl₃, 300 MHz) 9.75 (1H, d); 8.21 (1H, bs); 8.01 (1H, d); 7.58 (2H, m); 7.40 (2H, m); 7.33 (1H, t); 7.01 (3H, m); 6.65 (1H, d); 6.62 (1H, s); 3.91 (3H, s) | 390 (M + H) |
| 158 | ¹H (CDCl₃, +2 drops of DMSO-d6 300 MHz) 9.77 (1H, d); 9.28 (1H, bs); 8.38 (2H, d); 7.60 (1H, d); 7.37 (2H, m); 7.30 (1H, M); 7.18 (5H, m); 6.99 (1H, m); 6.62 (1H, s) | 342 (M + H) |
| 159 | ¹H (CDCl₃, +2 drops of DMSO-d6 300 MHz) 9.85 (1H, d); 9.42 (1H, bs); 7.93 (2H, d); 7.62 (1H, m); 7.42 (2H, m); 7.33 (3H, m); 7.18 (3H, m); 7.01 (1H, m); 6.64 (1H, s) | 385 (M + H) |
| 160 | ¹H(DMSO-d6 300 MHz) 10.66 (1H, s); 9.88 (1H, d); 7.87 (1H, d); 7.49 (1H, t); 7.39 (2H, d); 7.26 (4H, m); 7.11 (3H, m); 6.76 (1H, s); 2.94 (6H, s) | 412 (M + H) |
| 161 | ¹H (CDCl₃, +2 drops of DMSO-d6 300 MHz) 9.86 (1H, d); 9.57 (1H, bs); 7.73 (2H, d); 7.63 (1H, d); 7.44 (2H, m); 7.33 (3H, m); 7.20 (3H, m); 7.01 (1H, t); 6.63 (1H, s) | 384 (M + H) |
| 162 | ¹H (CDCl₃, 300 MHz) 9.76 (1H, d); 8.57 (2H, d); 8.43 (1H, bs); 7.66 (1H, d); 7.37 (3H, m); 7.20 (2H, d); 7.06 (1H, t); 6.84 (2H, d); 6.70 (1H, s); 3.78 (3H, s) | 372 (M + H) |
| 164 | ¹H (CDCl₃, 300 MHz) 9.63 (1H, d); 8.36 (1H, bs); 7.57 (1H, d); 7.46 (2H, d); 7.28 (2H, m); 6.95 (1H, m); 6.89 (2H, d); 6.71 (1H, s); 6.67 (1H, d); 6.47 (1H, m); 3.81 (3H, s) | 361 (M + H) |
| 165 | ¹H (CDCl₃, 300 MHz) 9.69 (1H, dd); 8.22 (1H, bs); 7.58 (1H, m); 7.30 (2H, m); 7.22 (2H, d); 7.10 (3H, m); 6.97 (2H, m); 6.69 (1H, s); 2.31 (3H, s) | 361 (M + H) |
| 166 | ¹H (CDCl₃, 300 MHz) 9.72 (1H, d); 8.68 (1H, bs); 7.81 (1H, d); 7.58 (1H, d); 7.27 (2H, m); 7.09 (2H, d); 6.93 (2H, m); 6.68 (1H, s); 6.48 (1H, d); 6.40 (1H, dd); 3.89 (3H, s); 3.79 (3H, s) | 407 (M + H) |
| 167 | ¹H (CDCl₃, 300 MHz) 9.68 (1H, d); 8.14 (1H, bs); 8.06 (1H, d); 7.65 (1H, dd); 7.58 (1H, d); 7.32 (2H, d); 7.12 (1H, d); 7.01 (2H, m); 6.69 (2H, d); 3.91 (3H, s) | 378 (M + H) |
| 168 | ¹H (CDCl₃, 300 MHz) 9.63 (1H, dd); 8.39 (1H, bs); 7.54 (1H, d); 7.45 (2H, d); 7.28 (2H, m); 7.16 (2H, m); 6.96 (1H, m); 6.71 (1H, s); 6.66 (1H, dd); 6.46 (1H, m); 2.33 (3H, s) | 343 (M + H) |
| 169 | ¹H (CDCl₃, 300 MHz) 9.66 (1H, d); 8.88 (1H, bs); 8.10 (1H, d); 7.56 (1H, d); 7.24 (2H, m); 6.94 (1H, m); 6.71 (1H, s); 6.66 (1H, d); 6.52 (1H, d); 6.44 (2H, m); 3.92 (3H, s); 3.81 (3H, s) | 391 (M + H) |

-continued

Analytical data for compounds representative of Examples 135 to 299

| Example | NMR Data | MS Spectrum |
|---|---|---|
| 170 | $^1$H (CDCl$_3$, 300 MHz) 9.64 (1H, d); 8.38 (1H, bs); 8.25 (1H, d); 7.91 (1H, dd); 7.56 (1H, m); 7.30 (2H, m); 6.97 (1H, m); 6.71 (2H, d); 6.66 (1H, m); 6.48 (1H, m); 3.94 (3H, s) | 362 (M + H) |
| 171 | $^1$H (CDCl$_3$, 300 MHz) 9.75 (1H, d); 8.55 (2H, m); 8.50 (1H, bs); 7.64 (1H, d); 7.34 (3H, m); 7.15-7.02 (5H, m); 6.68 (1H, s); 2.30 (3H, s) | 356 (M + H) |
| 172 | $^1$H (CDCl$_3$, 300 MHz) 9.76 (1H, d); 8.88 (1H, bs); 8.52 (2H, m); 7.61 (2H, m); 7.36 (3H, m); 7.04 (1H, t); 6.67 (1H, s); 6.48 (1H, d); 6.37 (1H, dd); 3.90 (3H, s); 3.78 (3H, s) | 402 (M + H) 400 (M − H) |
| 173 | $^1$H (CDCl$_3$, 300 MHz) 9.78 (1H, d); 8.68 (1H, d); 8.55 (1H, dd); 8.41 (1H, bs); 7.78 (1H, m); 7.65 (1H, d); 7.35 (1H, m); 7.27 (1H, m); 7.16 (2H, d); 7.08 (3H, m); 6.68 (1H, s); 2.31 (3H, s) | 356 (M + H) |
| 174 | $^1$H (CDCl$_3$, 300 MHz) 9.80 (1H, d); 8.78 (2H, d); 8.50 (1H, m); 7.77 (1H, d); 7.61 (2H, m); 7.32 (1H, t); 7.21 (1H, m); 7.02 (1H, t); 6.66 (1H, s); 6.46 (1H, m); 6.35 (1H, m); 3.88 (3H, s); 3.78 (3H, s) | 402 (M + H) |
| 175 | $^1$H (CDCl$_3$, 300 MHz) 9.60 (1H, d); 8.72 (1H, bs); 8.47 (1H, d); 7.73 (2H, m); 7.60 (1H, d); 7.27-7.16 (4H, m); 6.96 (3H, m); 6.79 (1H, s); 2.26 (3H, s) | 356 (M + H) |
| 176 | $^1$H (CDCl$_3$, 300 MHz) 9.67 (1H, d); 8.91 (1H, bs); 8.32 (1H, d); 7.75 (3H, m); 7.61 (1H, d); 7.24 (1H, m); 7.12 (1H, m); 6.96 (1H, m); 6.80 (1H, s); 6.51 (1H, m); 6.37 (1H, dd); 3.91 (3H, s); 3.79 (3H, s) | 402 (M + H) 400 (M − H) |
| 178 | $^1$H (CDCl$_3$, 300 MHz) 9.70 (1H, d); 7.57 (1H, d); 7.44-7.36 (5H, m); 7.26 (1H, m); 6.94 (1H, m); 6.60 (1H, s); 6.29 (1H, bd); 3.33 (1H, m); 1.68 (4H, m); 1.20 (6H, m) | 347 (M + H) |
| 179 | $^1$H (CDCl$_3$, 300 MHz) 9.75 (1H, d); 7.55 (1H, d); 7.42-7.37 (5H, m); 7.27 (1H, m); 6.96 (1H, m); 6.60 (1H, s); 2.51 (3H, d) | 279 (M + H) |
| 180 | $^1$H (CDCl$_3$, 300 MHz) 9.71 (1H, d); 7.57 (1H, d); 7.44-7.31 (5H, m); 7.25 (1H, m); 6.94 (1H, m); 6.59 (1H, s); 6.21 (1H, bd); 3.61 (1H, m); 1.03 (3H, s); 1.00 (3H, s) | 307 (M + H) |
| 181 | $^1$H (CDCl$_3$, 300 MHz) 9.77 (1H, d); 7.57 (1H, d); 7.45-7.36 (5H, m); 7.26 (1H, m); 6.96 (1H, m); 6.59 (2H, m); 3.33 (3H, s); 3.28 (2H, t); 3.10 (2H, q) | 323 (M + H) |
| 182 | $^1$H (CDCl$_3$, 300 MHz) 9.74 (1H, d); 7.58 (1H, d); 7.45-7.17 (11H, m); 6.95 (1H, t); 6.60 (2H, m); 4.09 (2H, d) | 355 (M + H) |
| 183 | $^1$H (CDCl$_3$, 300 MHz) 10.00 (1H, d); 9.98 (1H, d); 7.59-7.27 (6H, m); 6.99 (1H, m); 6.52 (1H, s); 2.76 (3H, s); 2.34 (3H, s) | 293 (M + H) |
| 196 | $^1$H (CDCl$_3$, 300 MHz) 9.51 (1H, d); 8.18 (1H, bs); 7.50 (1H, d); 7.42 (2H, m); 7.27 (3H, m); 7.13 (1H, d); 7.10 (1H, d); 7.06 (3H, m); 6.59 (1H, s); 3.92 (3H, s); 2.29 (3H, s) | 385 (M + H) |
| 200 | $^1$H (CDCl$_3$, 300 MHz) 9.75 (1H, d); 8.24 (1H, bs); 7.61 (1H, d); 7.44 (2H, m); 7.31 (4H, m); 7.16 (2H, m); 6.96 (3H, m); 6.65 (1H, s) | 359 (M + H) |
| 201 | $^1$H (CDCl$_3$, 300 MHz) 7.79 (1H, d); 8.43 (1H, s); 7.66 (2H, m); 7.44 (2H, m); 7.32 (3H, m); 7.03 (5H, m); 6.65 (1H, s) | 359 (M + H) |
| 202 | $^1$H (CDCl$_3$, 300 MHz) 9.74 (1H, d); 8.25 (1H, s); 7.60 (1H, d); 7.47 (2H, m); 7.34 (6H, m); 7.16 (1H, m); 7.04 (3H, m); 6.65 (1H, s); 2.33 (3H, s) | 355 (M + H) |
| 203 | $^1$H (CDCl$_3$, 300 MHz) 9.73 (1H, d); 8.11 (1H, s); 7.59 (1H, d); 7.46 (2H, m); 7.32 (5H, m); 7.07 (2H, m); 6.97 (1H, m); 6.64 (3H, m); 2.90 (6H, s) | 384 (M + H) |
| 204 | $^1$H (CDCl$_3$, 300 MHz) 9.74 (1H, d); 8.27 (1H, s); 7.61 (2H, d); 7.34 (7H, m); 7.03 (3H, m), 6.65 (1H, s) | 419, 421 (M + H) |
| 205 | $^1$H (CDCl$_3$, 300 MHz) 9.76 (1H, d); 8.46 (1H, s); 7.88 (2H, d); 7.62 (1H, d); 7.44 (2H, m); 7.32 (6H, m), 7.02 (1H, m); 6.66 (1H, s); 2.56 (3H, s) | 383 (M + H) |
| 206 | $^1$H (CDCl$_3$, 300 MHz) 9.75 (1H, d); 8.22 (1H, s); 7.61 (1H, d); 7.45 (2H, m); 7.30 (4H, m); 7.13 (1H, m); 6.98 (4H, m); 6.65 (1H, s) 2.29 (3H, s) | 355 (M + H) |
| 212 | $^1$H (CDCl$_3$, 300 MHz) 9.79 (1H, d); 8.67 (1H, s); 8.56 (2H, m); 7.81 (1H, d); 7.66 (1H, d); 7.54 (1H, d), 7.38 (3H, d); 7.26 (1H, m); 7.08 (1H, m); 2.29 (3H, s) | 410 (M + H) |
| 220 | $^1$H (CDCl$_3$, 300 MHz) 9.74 (1H, d); 8.29 (1H, s); 7.62 (1H, d); 7.42-7.29 (6H, m); 7.10 (2H, m), 7.02 (1H, m); 6.65 (1H, s) | 409 (M + H) |
| 221 | $^1$H (CDCl$_3$, 300 MHz) 9.75 (1H, d); 8.32 (1H, s); 7.61 (1H, d); 7.44 (2H, m); 7.32 (6H, m), 7.22 (2H, d); 7.00 (1H, m); 6.62 (1H, s); 1.69 (3H, s); 1.55 (3H, s) | 406 (M + H) |
| 223 | $^1$H (CDCl$_3$, 300 MHz) 9.78 (1H, d); 8.63 (2H, d); 8.53 (1H, dd); 7.79 (1H, dt); 7.65 (1H, d), 7.49 (1H, m); 7.44-7.30 (6H, m); 7.28 (1H, m); 7.08 (1H, m); 6.67 (1H, m) | 408 (M + H) |
| 228 | $^1$H (CDCl$_3$, 300 MHz) 9.76 (1H, dd); 8.35 (1H, s); 7.61 (1H, d); 7.45 (2H, m); 7.43-7.27 (7H, m); 7.16 (1H, m); 7.00 (1H, m); 6.65 (1H, s); 1.66 (3H, s); 1.57 (3H, s) | 406 (M − H) 408 (M + H) |
| 229 | $^1$H (CDCl$_3$, 300 MHz) 9.74 (1H, dd); 8.05 (1H, s); 7.94 (1H, d); 7.60 (1H, m); 7.45 (2H, m), 7.39 (5H, m); 7.01 (1H, m); 6.64 (1H, s); 6.39 (1H, d); 3.05 (6H, s) | 383 (M + H) |
| 232 | $^1$H (CDCl$_3$, 300 MHz) 9.76 (1H, d); 7.89 (1H, s); 7.58 (1H, d); 7.32 (2H, m); 7.20 (3H, m), 7.00 (4H, m); 6.76 (2H, d); 6.54 (1H, s); 3.76 (3H, s); 2.34 (3H, s) | 383 (M − H) 385 (M + H) |
| 233 | $^1$H (CDCl$_3$, 300 MHz) 9.72 (1H, d); 8.14 (1H, s); 7.58 (1H, d); 7.32 (2H, m); 7.22 (3H, m), 7.15 (3H, m), 6.96 (1H, m); 6.77 (2H, d); 6.63 (1H, s); 3.78 (3H, s); 2.19 (3H, s) | 385 (M + H) |

-continued

Analytical data for compounds representative of Examples 135 to 299

| Example | NMR Data | MS Spectrum |
|---|---|---|
| 235 | $^1$H (CDCl$_3$, 300 MHz) 9.73 (1H, d); 8.24 (1H, s); 7.61 (1H, d); 7.44 (1H, m); 7.34 (3H, m); 7.23 (3H, m), 7.02 (1H, m); 6.82 (2H, m); 6.64 (1H, s); 3.79 (3H, s) | 405 (M + H) |
| 238 | $^1$H (CDCl$_3$, 300 MHz) 9.73 (1H, d); 8.10 (1H, s); 7.58 (1H, d); 7.35 (3H, m); 7.12 (4H, m); 6.96 (1H, m); 6.79 (2H, m); 6.61 (1H, s); 3.78 (3H, s); 2.31 (3H, s) | 383 (M − H) |
| 240 | $^1$H (CDCl$_3$, 300 MHz) 9.75 (1H, d); 8.25 (1H, s); 7.60 (1H, m); 7.45 (2H, m); 7.32 (4H, m); 7.16 (1H, t), 7.01 (1H, m); 6.89 (1H, m); 6.75-6.64 (3H, m); 3.97 (2H, t); 2.71 (2H, t); 2.35 (6H, s) | 428 (M + H) |
| 243 | $^1$H (CDCl$_3$, 300 MHz) 9.74 (1H, d); 8.35 (1H, s); 7.60 (3H, m); 7.45 (2H, m); 7.33 (6H, m); 6.99 (1H, t), 6.56 (1H, s); 3.98 (3H, s); 2.18 (3H, s) | 412 (M + H) |
| 246 | $^1$H (CDCl$_3$, 300 MHz) 9.73 (1H, d); 8.18 (1H, s); 7.60 (1H, d); 7.46-7.23 (7H, m); 7.07 (3H, m); 6.56 (1H, s); 2.27 (3H, s) | 389 (M + H) |
| 250 | $^1$H (DMSO-d6 300 MHz) 11.07 (1H, s); 10.60 (1H, s); 9.86 (1H, d); 7.86 (1H, d); 7.60-7.29 (5H, m); 7.25-6.82 (6H, m); 6.75 (1H, s), 2.10 (3H, s) | 398 (M + H) |
| 251 | $^1$H (CDCl$_3$, 300 MHz) 9.73 (1H, d); 8.17 (1H, s); 7.60 (1H, d); 7.47 (2H, m); 7.33 (4H, m); 7.12 (2H, d), 7.01 (1H, m); 6.81 (2H, d); 6.64 (1H, s); 3.86 (4H, m); 3.12 (4H, m) | 426 (M + H) |
| 252 | $^1$H (CDCl$_3$, 300 MHz) 9.74 (1H, d); 8.24 (1H, s); 7.60 (1H, m); 7.47 (2H, m); 7.34 (4H, m); 7.10 (4H, m); 6.99 (1H, m); 6.65 (1H, s); 2.85 (1H, m); 1.22 (6H, d) | 383 (M + H) |
| 256 | $^1$H (CDCl$_3$, 300 MHz) 9.75 (1H, d); 8.28 (1H, s); 7.60 (1H, d); 7.49 (3H, m); 7.30 (4H, m); 7.20 (1H, d), 7.00 (3H, m); 6.65 (1H, s); 6.39 (1H, m); 3.76 (3H, s) | 394 (M + H) |
| 258 | $^1$H (CDCl$_3$, 300 MHz) 9.73 (1H, d); 8.18 (1H, s); 7.59 (1H, d); 7.45 (2H, m); 7.31 (4H, m); 7.09 (2H, d), 6.98 (1H, t); 6.79 (2H, d); 6.64 (1H, s); 3.46 (4H, m); 2.74 (4H, m) | 442 (M + H) |
| 259 | $^1$H (CDCl$_3$, 300 MHz) 9.73 (1H, d); 8.18 (1H, s); 7.59 (1H, d); 7.48 (2H, m); 7.35 (4H, m); 6.98 (1H, m), 6.87 (2H, m); 6.64 (1H, s); 2.20 (9H, m) | 383 (M + H) |
| 260 | $^1$H (CDCl$_3$, 300 MHz) 9.72 (1H, d); 8.09 (1H, s); 7.58 (1H, d); 7.46 (2H, m); 7.31 (3H, m); 7.24 (1H, m), 7.05 (2H, d); 6.96 (1H, m); 6.63 (1H, s); 6.44 (2H, d); 3.24 (4H, t), 1.98 (4H, m) | 410 (M + H) |
| 261 | $^1$H (CDCl$_3$, 300 MHz) 9.72 (1H, d); 8.07 (1H, s); 7.59 (1H, d); 7.46 (2H, m); 7.31 (4H, m); 6.97 (2H, m); 6.86 (1H, m); 6.63 (1H, s); 6.35 (1H, d); 3.26 (2H, t); 2.87 (2H, t); 2.72 (3H, s) | 396 (M + H) |
| 264 | $^1$H (DMSO-d6 300 MHz) 10.52 (1H, s); 9.85 (1H, d); 7.85 (1H, m); 7.50 (1H, m); 7.36 (2H, m); 7.23 (8H, m); 6.74 (1H, s); 3.96 (2H, m); 3.67 (2H, m); 1.52 (1H, s) | 427 (M + H) |
| 268 | $^1$H (CDCl$_3$, 300 MHz) 9.75 (1H, d); 8.47 (1H, s); 7.94 (2H, d); 7.68 (1H, m); 7.60 (1H, m); 7.44 (2H, m); 7.30 (6H, m); 7.21 (1H, m); 6.99 (1H, m); 6.65 (1H, s) | 408 (M + H) |
| 270 | $^1$H (CDCl$_3$, 300 MHz) 9.76 (1H, d); 8.28 (1H, s); 8.21 (1H, d); 7.62 (1H, d); 7.48 (3H, m); 7.33 (3H, m); 7.23 (4H, dd); 7.02 (1H, t); 6.82 (1H, d); 6.76 (1H, m); 6.67 (1H, s); 6.49 (1H, bs); 4.84 (1H, bs) | 433 (M + H) |
| 272 | $^1$H (CDCl$_3$, 300 MHz) 9.74 (1H, d); 8.20 (1H, s); 7.61 (1H, d); 7.47 (2H, m); 7.33 (3H, m); 7.13 (2H, d), 7.00 (2H, m); 6.88 (2H, d); 6.61 (1H, s); 3.54 (4H, m); 2.56 (4H, m) | 438 (M + H) |
| 273 | $^1$H (CDCl$_3$, 300 MHz) 9.75 (1H, d); 8.18 (1H, s); 7.61 (1H, d); 7.48 (2H, m); 7.34 (4H, m); 7.00 (2H, m); 6.93 (2H, m); 6.66 (1H, s); 2.67 (6H, s); 2.27 (1H, s) | 398 (M + H) |
| 275 | $^1$H (CDCl$_3$, 300 MHz) 9.72 (1H, d); 8.06 (1H, s); 7.56 (1H, d); 7.44 (2H, m); 7.30 (4H, m); 7.02 (2H, d), 6.94 (1H, t); 6.62 (1H, s); 6.40 (2H, d); 4.20 (1H, d); 3.71 (3H, s); 3.52 (1H, m); 3.28 (1H, m); 2.24 (1H, m); 2.18 (2H, m); 2.02 (1H, m) | 468 (M + H) |
| 277 | $^1$H (CDCl$_3$, 300 MHz) 10.40 (1H, s); 9.84 (1H, d); 7.85 (1H, d); 7.48 (1H, t); 7.37 (2H, m); 7.22 (3H, m); 7.08 (2H, m); 6.89 (1H, m); 6.73 (1H, s) | 411 (M + H) |
| 281 | $^1$H (CDCl$_3$, 300 MHz) 9.74 (1H, d); 8.27 (1H, bs); 7.61 (1H, d); 7.42 (2H, m); 7.29 (4H, m); 7.16 (4H, m); 7.00 (1H, m); 6.65 (1H, s) | 375 (M + H) |
| 282 | $^1$H (CD3OD, 300 MHz) 9.92 (1H, d); 7.77 (1H, d); 7.48-7.32 (5H, m); 7.23-7.08 (4H, m); 6.98 (1H, d); 6.68 (1H, s); 3.89 (3H, s); 2.55 (3H, s) | 413 (M + H) |
| 284 | $^1$H (CDCl3, 300 MHz) 9.74 (1H, d); 8.26 (1H, bs); 7.60 (1H, d); 7.45 (2H, m); 7.32-7.29 (5H, m); 7.26 (2H, m); 7.16 (2H, d); 7.01 (1H, m); 3.63 (2H, s); 2.17 (3H, s) | 397 (M + H) 395 (M − H) |
| 286 | $^1$H (CDCl3, 300 MHz) 9.76 (1H, d); 7.93 (1H, s); 7.81 (1H, d); 7.60 (1H, d); 7.36-7.33 (2H, m); 7.26-7.14 (2H, m); 7.31 (dd, 2H); 6.69 (1H, d), 6.56 (1H, s); 6.14-5.85 (1H, m); 4.68 (2H, t); 2.33 (3H, s) | 485 (M + H) 483 (M − H) |
| 287 | $^1$H (CDCl$_3$, 300 MHz) 9.75 (1H, d); 8.53 (1H, bs); 7.61 (1H, d); 7.47-7.42 (3H, m); 7.34-7.27 (5H, m); 7.14 (2H, m); 7.09 (1H, m); 6.62 (1H, s); 2.38 (3H, s); 2.25 (3H, s) | 436 (M + H) |
| 288 | $^1$H (CDCl3, 300 MHz) 9.78 (1H, d); 8.33 (1H, bs); 7.77 (2H, m); 7.71 (1H, d); 7.58 (1H, d); 7.45 (2H, m); 7.39 (2H, m); 7.35-7.24 (6H, m); 7.00 (1H, dt); 6.63 (1H, s) | 408 (M + H) 406 (M − H) |
| 291 | $^1$H (CDCl3, 300 MHz) 9.65 (1H, d); 8.39 (1H, s); 7.88 (1H, s); 7.60 (1H, d); 7.54 (2H, d); 7.44 (2H, m); 7.29 (7H, m); 7.18 (1H, m); 7.01 (1H, m); 6.65 (1H, s) | 408 (M + H) |

-continued

Analytical data for compounds representative of Examples 135 to 299

| Example | NMR Data | MS Spectrum |
|---|---|---|
| 292 | $^1$H (CDCl3, 300 MHz) 9.74 (1H, d); 8.20 (1H, s); 7.73 (1H, s); 7.58 (1H, d); 7.50 (1H, d); 7.45 (1H, d); 7.43 (2H, m); 7.28 (6H, m); 6.98 (1H, m); 6.94 (1H, d); 6.63 (1H, s); 2.70 (6H, s) | 451 (M + H) |
| 293 | $^1$H (CDCl3, 300 MHz) 9.76 (1H, d); 8.40 (1H, s); 7.84 (3H, m); 7.60 (1H, d); 7.44 (2H, m); 7.30 (7H, m); 7.00 (1H, m); 6.65 (1H, s) | 424 (M + H) |
| 298 | $^1$H (CDCl3, 300 MHz) 9.03 (1H, d); 8.30 (1H, s); 7.50-7.28 (5H, m); 7.24 (2H, m); 7.19-6.56 (5H, m), 4.09 (3H, d); 3.76 (3H, s) | 400 (M + H) |
| 299 | $^1$H (DMSO-d6 300 MHz) 10.87 (1H, s); 9.88 (1H, d); 7.88 (1H, m); 7.31 (2H, d); 7.54-7.24 (6H, m), 7.09 (3H, m); 6.77 (1H, s); 4.62 (2H, m); 4.07 (2H, m); 3.37 (3H, d); 3.09 (2H, m); 2.89 (2H, m) | |

Measurement of Minimum Inhibitory Concentrations (MICs)

Between 1 and 5 mgs of compound were accurately weighed out into a sterile Eppendorf tube. The compound was dissolved in DMSO to give a solution containing 5 mg/ml. Tubes were stored at −20° C. until required.

On the day of testing thawed solutions were vortex mixed to ensure homogeneity. 30 µl of solution was removed and added to 570 µl of sterile water in a separate sterile Eppendorf. The thoroughly mixed solution was used to prepare a series of doubling dilutions in water, in a deep well plate. Eleven replicate plates were prepared using a Minitrak by aspirating 20 µl from each well into eleven clear polystyrene 96 well plates.

Spores of Aspergillus spp (Aspergillus fumigatus, Aspergillus terreus, Aspergillus niger and Aspergillus flavus) were harvested from cultures grown on Sabarauds agar for 5 days, and resuspended in PBS/Tween 80 to approx $1 \times 10^7$ cfu/ml Other filamentous fungi (Fusarium solani, Scedosporium spp., Trichophyton spp., Absidia corymbifera), were grown on Sabarauds agar for 2-10 days and spores/hyphae resuspended in PBS/Tween to give approx $1 \times 10^7$ cfU/ml. Candida species (Candida albicans, Candida glabrata, Candida krusei, Candida parapsilosis and Candida tropicalis) were grown on Sabarauds agar, cells were harvested from the agar using a sterile loop and resuspended in PBS/Tween 80 to approx $1 \times 10^6$ cfu/ml. Each organism suspension was diluted in RPMI medium, containing 2% glucose and 0.135M MOPS buffer (pH7.0) to $2 \times 10^4$ cfu/ml for Aspergillus spp and other filamentous fungi and $2 \times 10^3$ cfu/ml for yeast. 80 µl of an organism suspension was added to each well of the plate containing drug dilutions.

This produced MIC plates with a drug range 50-0.05 mg/L and organism inocula of $1-2 \times 10^4$ cfu/ml for Aspergillus spp and other filamentous fungi and $1-2 \times 10^3$ cfu/ml for yeasts. All plates were incubated for 24-48 hrs at 35° C. Growth was assessed by monitoring the optical density at 485 nm for each well. The MIC of a compound is the lowest drug concentration that inhibits growth of an organism by >80% compared with a drug free control. MICs are recorded as mg/L. Other growth media can be used for susceptibility testing, and the activity of the described compounds can also be assessed in a medium comprising, 1% glucose, 1% ammonium chloride and 0.5% yeast extract (YAG medium). To perform MIC tests in this medium, dilutions of compounds are prepared in microtitre plates as described above. Fungal strains to be tested are grown and harvested in an identical manner to that described above, each organism suspension is then diluted in YAG medium to $2 \times 10^4$ cfu/ml for Aspergillus spp and other filamentous fungi and $2 \times 10^3$ cfu/ml for yeast. 80 µl of an organism suspension was added to each well of the plate containing drug dilutions. This produced MIC plates with a drug range 50-0.05 mg/L and organism inocula of $1-2 \times 10^4$ cfu/ml for Aspergillus spp and other filamentous fungi and $1-2 \times 10^3$ cfu/ml for yeasts. All plates were incubated for 24 hrs at 35° C. Growth was assessed by monitoring the optical density at 485 nm for each well. The MIC of a compound is the lowest drug concentration that inhibits growth of an organism by >70% compared with a drug free control. MICs are recorded as mg/L. In cases where the MIC of an organism is >=0.05 mg/L the MIC is repeated using a concentration range of 0.5-0.0005 mg/L. MIC tests in YAG medium have more clear-cut endpoints and have slightly lower MICS than those performed in RPMI medium.

The following organisms were tested: Aspergillus fumigatus AF293 and Aspergillus fumigatus AF210, Aspergillus niger, Aspergillus terreus, Aspergillus favus, Candida albicans, Candida krusei, Candida tropicalis, Candida glabrata, Candida parapsilosis, Trichophyton rubrum, Trichophyton mentagrophytes, Scedosporium prolificans, Scedosporium apiospermum, Absidia corymbifera, Fusarium solani.

Table 1 shows the antifungal MICs of selected compounds of the invention against Aspergillus species.

Table 2 shows the antifungal MICs of selected commercially available compounds which fall under the definition of this invention.

Table 3 shows the antifungal MICs of selected compounds of the invention against Candida species.

TABLE 1

MIC results in mg/L (YAG medium)

| Example no. | A Flavus 01 | A Fum. 293 | A Niger 1 | A Terreus 4 | A Fum. 210 | A Terreus 49 |
|---|---|---|---|---|---|---|
| 135 | 0.015 | 0.12 | 0.015 | 0.008 | 0.062 | 0.002 |
| 136 | 0.031 | 0.25 | 0.031 | 0.031 | 0.12 | 0.004 |
| 137 | 0.125 | 0.2 | 0.062 | 0.06 | 0.5 | 0.06 |
| 138 | 0.015 | 0.12 | 0.12 | 0.031 | 0.12 | 0.004 |
| 139 | 0.008 | 0.12 | 0.031 | 0.008 | 0.12 | 0.002 |
| 140 | 0.031 | 0.12 | 0.031 | 0.031 | 0.12 | 0.015 |

TABLE 1-continued

| Example no. | A Flavus 01 | A Fum. 293 | A Niger 1 | A Terreus 4 | A Fum. 210 | A Terreus 49 |
|---|---|---|---|---|---|---|
| 141 | 0.008 | 0.12 | 0.25 | 0.031 | 0.12 | 0.015 |
| 142 | >50 | >50 | 0.8 | >50 | >50 | |
| 143 | 0.031 | 0.061 | 0.015 | 0.031 | 0.06 | 0.008 |
| 144 | 0.015 | 0.06 | 0.008 | 0.062 | 0.062 | 0.008 |
| 145 | 0.031 | 0.5 | 0.031 | 0.031 | 0.5 | 0.004 |
| 146 | 0.062 | 0.5 | 0.25 | 0.062 | 0.5 | 0.03 |
| 147 | 0.1 | 12.5 | 0.1 | 3.1 | 6.25 | |
| 148 | 0.008 | 0.12 | 0.062 | 0.008 | 0.12 | 0.008 |
| 149 | 0.031 | 0.5 | 0.031 | 0.06 | 1.6 | 0.031 |
| 150 | 0.125 | 1.6 | 0.25 | 0.5 | 1.6 | 0.12 |
| 151 | 1.6 | 6.25 | 0.4 | 0.4 | 6.25 | |
| 152 | 1.6 | 12.5 | 0.4 | 0.8 | 25 | |
| 153 | 3.1 | >50 | 0.8 | >50 | 25 | |
| 154 | 0.25 | 1.6 | 0.05 | 0.8 | 1.6 | 0.12 |
| 155 | 0.03 | 0.5 | 0.12 | 0.031 | 0.12 | 0.008 |
| 156 | 0.015 | 0.25 | 0.031 | 0.031 | 0.25 | 0.015 |
| 157 | 0.1 | 6.25 | 0.1 | 0.2 | 1.6 | |
| 158 | >50 | >50 | 0.4 | >50 | >50 | |
| 159 | >50 | >50 | 1.6 | 50 | >50 | |
| 160 | 3.1 | 50 | 0.4 | 50 | 50 | |
| 161 | >50 | >50 | 6.25 | >50 | >50 | |
| 162 | >50 | >50 | 3.1 | >50 | >50 | |
| 163 | >50 | >50 | 1.6 | >50 | >50 | |
| 164 | 0.4 | >50 | 0.4 | >50 | >50 | |
| 165 | 0.062 | 0.8 | 0.25 | 0.06 | 1.6 | 0.062 |
| 166 | 0.12 | 1.6 | 0.25 | 0.12 | 3.1 | 0.062 |
| 167 | 0.062 | 1.6 | 0.5 | 0.25 | 1.6 | 0.062 |
| 168 | 0.4 | 1.6 | 0.4 | 1.6 | 3.1 | |
| 169 | 0.4 | 3.1 | 0.4 | 3.1 | 6.25 | |
| 170 | 3.1 | >50 | 3.1 | >50 | >50 | |
| 171 | 0.4 | 50 | >50 | 0.8 | 1.6 | |
| 172 | 0.4 | 25 | 3.1 | 1.6 | 25 | |
| 173 | 0.12 | 0.5 | 0.5 | 0.12 | 0.4 | 0.12 |
| 174 | 0.1 | 6.25 | 1.6 | 0.2 | 3.1 | |
| 175 | >50 | >50 | >50 | 3.1 | 3.1 | |
| 176 | >50 | >50 | 3.1 | >50 | >50 | |
| 177 | >50 | 50 | 6.25 | 6.25 | >50 | |
| 178 | 1.6 | 0.8 | 0.2 | 0.1 | 0.8 | |
| 179 | 25 | 12.5 | >50 | 6.25 | 12.5 | |
| 180 | >50 | 6.25 | 3.1 | 6.25 | 6.25 | |
| 181 | 25 | 50 | 25 | 25 | 25 | |
| 182 | >50 | >50 | >50 | 0.2 | >50 | |
| 183 | >50 | >50 | >50 | 12.5 | 25 | |
| 184 | 50 | 25 | 0.8 | 6.25 | 6.25 | |
| 186 | 25 | 12.5 | 3.1 | 12.5 | 3.1 | |
| 187 | >50 | >50 | 3.1 | >50 | >50 | |
| 188 | 3.1 | 1.6 | 0.4 | 0.8 | 0.8 | |
| 189 | 3.1 | 3.1 | 0.8 | 1.6 | 3.1 | |
| 190 | 0.4 | 1.6 | 0.4 | 0.1 | 1.6 | |
| 191 | 0.8 | 3.1 | 1.6 | 0.2 | 3.1 | |
| 192 | 0.4 | 1.6 | 0.8 | 0.4 | 1.6 | |
| 193 | 6.25 | >50 | >50 | 0.8 | >50 | |
| 194 | >50 | >50 | >50 | 25 | >50 | |
| 195 | 0.4 | 6.25 | 1.6 | 0.4 | 6.25 | |
| 196 | 0.12 | 0.8 | 0.5 | 0.12 | 0.8 | 0.062 |
| 197 | 0.4 | 3.1 | 0.8 | 0.2 | 3.1 | |
| 198 | 0.8 | 3.1 | 1.6 | 0.8 | >50 | |
| 199 | >50 | >50 | >50 | 1.6 | >50 | |
| 200 | 0.062 | 0.25 | 0.031 | 0.015 | 0.25 | 0.015 |
| 201 | 0.12 | 0.5 | 0.015 | 0.015 | 0.25 | 0.015 |
| 202 | 0.062 | 0.5 | 0.031 | 0.008 | 0.25 | 0.015 |
| 203 | 0.008 | 0.06 | 0.031 | 0.015 | 0.062 | 0.008 |
| 204 | 0.031 | 0.25 | 0.031 | 0.015 | 0.25 | 0.015 |
| 205 | 0.062 | 0.5 | 0.062 | 0.031 | 0.5 | 0.062 |
| 206 | 0.008 | 0.062 | 0.015 | 0.004 | 0.062 | 0.008 |
| 207 | 0.1 | 0.8 | 0.05 | 0.05 | 0.8 | |
| 208 | >50 | >50 | >50 | 12.5 | >50 | |
| 209 | 0.1 | >50 | 0.05 | 0.05 | >50 | |
| 210 | 0.05 | >50 | 0.05 | 0.05 | >50 | |
| 211 | 0.4 | 6.25 | 1.6 | 0.2 | 6.25 | |
| 212 | 0.05 | 0.8 | 0.4 | 0.1 | 0.4 | |
| 213 | 0.4 | 6.25 | 1.6 | 0.8 | 6.25 | |
| 214 | 0.1 | 0.8 | 0.4 | 0.1 | 0.8 | |
| 215 | 0.05 | 0.8 | 0.4 | 0.05 | 0.4 | |
| 216 | 0.2 | 6.25 | 0.4 | 0.2 | 6.25 | |
| 217 | 0.8 | >50 | >50 | 3.1 | >50 | |

TABLE 1-continued

| | MIC results in mg/L (YAG medium) | | | | | |
|---|---|---|---|---|---|---|
| Example no. | A Flavus 01 | A Fum. 293 | A Niger 1 | A Terreus 4 | A Fum. 210 | A Terreus 49 |
| 218 | >50 | >50 | 0.4 | >50 | >50 | |
| 219 | >50 | 12.5 | 3.1 | 6.25 | 50 | |
| 220 | 0.015 | 0.12 | 0.062 | 0.031 | 0.12 | 0.008 |
| 221 | 0.015 | 0.062 | 0.015 | 0.015 | 0.03 | 0.008 |
| 222 | 0.05 | 1.6 | 3.1 | 0.4 | 1.6 | |
| 223 | 0.062 | 0.5 | 0.5 | 0.12 | 0.25 | 0.031 |
| 224 | 0.05 | 6.25 | 0.2 | 0.1 | 6.25 | |
| 225 | 0.1 | 3.1 | 3.1 | 0.1 | 3.1 | |
| 226 | 1.6 | >50 | >50 | 3.1 | >50 | |
| 227 | 0.05 | 1.6 | 1.6 | 0.05 | 0.8 | |
| 228 | 0.004 | 0.031 | 0.015 | 0.004 | 0.031 | 0.002 |
| 229 | 0.031 | 0.5 | 0.12 | 0.12 | 0.5 | 0.062 |
| 230 | 0.1 | >50 | 3.1 | 0.2 | >50 | |
| 231 | 0.05 | 1.6 | 0.8 | 0.1 | 0.8 | |
| 232 | 0.015 | 0.062 | 0.008 | 0.031 | 0.062 | 0.015 |
| 233 | 0.004 | 0.25 | 0.06 | 0.008 | 0.25 | 0.004 |
| 234 | >50 | >50 | >50 | 1.6 | >50 | |
| 235 | 0.031 | 0.5 | 0.12 | 0.015 | 0.5 | 0.008 |
| 236 | 0.1 | >50 | >50 | 0.05 | >50 | |
| 237 | 1.6 | 1.6 | 0.8 | 0.4 | 3.1 | |
| 238 | 0.015 | 0.5 | 0.015 | 0.015 | 0.25 | 0.008 |
| 239 | 0.05 | 50 | 0.8 | 0.05 | >50 | |
| 240 | 12.5 | 50 | >50 | 12.5 | >50 | |
| 241 | 0.8 | 12.5 | 12.5 | 12.5 | 12.5 | |
| 242 | 0.05 | 0.8 | 0.4 | 0.1 | 0.8 | |
| 243 | 0.015 | 0.062 | 0.015 | 0.008 | 0.12 | 0.004 |
| 244 | 0.2 | >50 | 0.05 | 0.2 | >50 | 0.1 |
| 245 | 0.8 | 6.25 | 0.4 | 0.4 | 6.25 | 0.8 |
| 246 | 0.031 | 0.12 | 0.062 | 0.008 | 0.25 | 0.004 |
| 247 | 1.6 | 3.1 | 3.1 | 0.4 | 3.1 | 0.2 |
| 248 | >50 | 12.5 | 0.4 | 6.25 | 12.5 | 6.25 |
| 249 | >50 | 0.8 | 6.25 | 1.6 | 1.6 | 1.6 |
| 250 | 0.1 | 0.2 | 0.05 | 0.1 | 0.8 | 0.05 |
| 251 | 0.062 | 0.12 | 0.062 | 0.031 | 0.12 | 0.015 |
| 252 | 0.015 | 0.008 | 0.004 | 0.008 | 0.062 | 0.002 |
| 253 | 25 | >50 | >50 | 12.5 | >50 | 12.5 |
| 254 | 0.4 | 1.6 | 0.4 | 0.1 | 0.8 | 0.2 |
| 255 | 0.2 | 1.6 | 0.4 | 0.2 | 0.8 | 0.1 |
| 256 | 0.04 | 0.015 | 0.03 | 0.001 | 0.015 | 0.001 |
| 257 | 0.4 | 6.25 | 0.8 | 0.4 | 3.1 | 0.4 |
| 258 | 0.015 | 0.03 | 0.03 | 0.008 | 0.015 | 0.008 |
| 259 | 0.015 | 0.06 | 0.03 | 0.002 | 0.06 | 0.004 |
| 260 | 0.008 | 0.015 | 0.015 | 0.008 | 0.03 | 0.008 |
| 261 | 0.004 | 0.03 | 0.06 | 0.004 | 0.03 | 0.001 |
| 262 | 1.6 | 1.6 | 6.25 | 1.6 | 1.6 | 1.6 |
| 263 | 0.05 | 0.4 | 0.8 | 0.2 | 0.4 | 0.1 |
| 264 | 0.05 | 0.05 | 0.05 | 0.015 | 0.05 | 0.008 |
| 265 | 0.1 | >50 | 0.008 | 0.015 | >50 | 0.06 |
| 266 | 0.2 | 0.8 | 6.25 | 0.2 | 1.6 | 0.2 |
| 267 | 0.05 | 0.4 | 0.4 | 0.1 | 0.8 | 0.05 |
| 268 | 0.03 | 0.1 | 0.015 | 0.015 | 0.06 | 0.015 |
| 269 | 0.2 | 1.6 | 0.1 | 0.2 | 1.6 | 0.2 |
| 270 | 0.05 | 0.05 | 0.05 | 0.05 | 0.015 | 0.12 |
| 271 | 50 | 50 | 50 | 25 | 50 | 25 |
| 272 | 0.062 | 0.25 | 0.5 | 0.12 | 0.5 | 0.12 |
| 273 | 0.004 | 0.062 | 0.12 | 0.004 | 0.031 | 0.002 |
| 274 | 50 | 50 | >50 | >50 | >50 | 12.5 |
| 275 | 0.03 | 0.05 | 0.4 | 0.03 | 0.03 | 0.015 |
| 276 | 0.05 | 0.1 | 0.05 | 0.05 | 0.2 | 0.015 |
| 277 | 0.03 | 0.4 | 0.03 | 0.015 | 0.05 | 0.2 |
| 278 | 6.25 | 25 | 25 | 6.25 | 12.5 | 12.5 |
| 281 | 0.031 | 0.25 | 0.031 | 0.031 | 0.12 | 0.008 |
| 282 | 0.008 | 0.1 | 0.1 | 0.015 | 0.1 | 0.004 |
| 283 | 0.015 | 0.2 | 0.05 | 0.1 | 0.2 | 0.05 |
| 284 | 0.05 | 0.1 | 0.05 | 0.05 | 0.1 | 0.015 |
| 285 | 0.05 | 0.4 | 0.05 | 0.05 | 0.8 | 0.03 |
| 286 | 0.015 | 0.1 | 0.015 | 0.1 | 0.1 | 0.015 |
| 287 | 0.03 | 0.05 | 0.015 | 0.03 | 0.1 | 0.008 |
| 288 | 0.015 | 0.1 | 0.1 | 0.008 | 0.2 | 0.004 |
| 289 | 0.004 | 0.05 | 0.004 | 0.008 | 0.05 | 0.008 |
| 290 | 0.05 | 0.1 | 0.05 | 0.03 | 0.2 | 0.003 |
| 291 | 0.03 | 0.8 | 0.05 | 0.015 | 3.1 | 0.015 |
| 292 | 0.03 | 0.4 | 0.8 | 0.03 | 0.2 | 0.015 |
| 293 | 0.05 | 0.1 | 0.008 | 0.015 | 0.4 | 0.004 |
| 294 | 25 | 25 | 50 | 50 | >50 | 25 |
| 295 | 12.5 | >50 | 25 | 6.25 | 50 | 6.25 |

TABLE 1-continued

MIC results in mg/L (YAG medium)

| Example no. | A Flavus 01 | A Fum. 293 | A Niger 1 | A Terreus 4 | A Fum. 210 | A Terreus 49 |
|---|---|---|---|---|---|---|
| 296 | 12.5 | >50 | 25 | 6.25 | >50 | 6.25 |
| 297 | 0.4 | 12.5 | 1.6 | 0.8 | 12.5 | 0.4 |
| 298 | 0.1 | 0.8 | 0.2 | 0.2 | 0.8 | |
| 299 | 3.1 | 6.25 | 12.5 | 3.1 | 6.25 | 1.6 |

TABLE 2

MICs of commercial compounds in mg/L (YAG medium)

| Example no. | A Flavus | A Fum. 293 | A Niger | A Terreus | A Fum. 210 | A Terreus 49 |
|---|---|---|---|---|---|---|
| 300 | >50 | >50 | 25 | >50 | >50 | |
| 301 | 50 | 25 | 25 | 12.5 | 25 | |
| 302 | >50 | 50 | >50 | 25 | 25 | |
| 303 | 50 | 50 | 50 | 25 | 50 | |
| 304 | 0.031 | 0.25 | 0.015 | 0.015 | 0.25 | 0.015 |
| 305 | 0.062 | 0.5 | 0.015 | 0.031 | 0.5 | 0.015 |
| 306 | 0.008 | 0.12 | 0.015 | 0.004 | 0.062 | 0.002 |
| 307 | 0.008 | 0.008 | 0.008 | 0.002 | 0.05 | 0.001 |

TABLE 3

MICs in mg/L against Candida species (RPMI medium)

| Example No. | C. albicans | C. glabrata | C. krusei | C. parapsilosis | C. tropicalis |
|---|---|---|---|---|---|
| 185 | 50 | >50 | >50 | 50 | 12.5 |
| 212 | >50 | 25 | >50 | >50 | >50 |
| 270 | 6.25 | 50 | 50 | 50 | 25 |
| 271 | 3.1 | 50 | 50 | 50 | 25 |
| 272 | 1.6 | 50 | 50 | 25 | 6.25 |
| 274 | 3.1 | >50 | >50 | 50 | 12.5 |
| 275 | 25 | >50 | >50 | >50 | >50 |

The invention claimed is:

1. A compound which is an indolizinyl derivative of formula (I), or a pharmaceutically acceptable salt thereof:

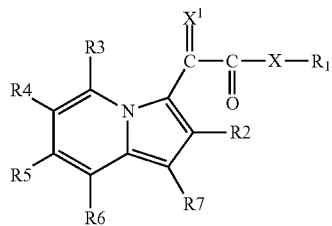

(I)

wherein:

X is a bond, $-NR8-$, $-O-$, $-S-$, $-SO-$, or $-SO_2-$;

$X^1$ is O or NOR9, wherein R9 is hydrogen or an unsubstituted or substituted C1-C4 alkyl group;

R1 represents an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, $-COR'$, and $-Y-Z$;

R8 represents hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, $-COR'$, and $-Y-Z$;

or when X is NR8, R1 and R8 together with the nitrogen to which they are attached may form an unsubstituted or substituted, aromatic or non-aromatic 5- to 12-membered heterocyclyl group;

A1 is an unsubstituted or substituted C6-C10 arylene group;

L1 is a bond, $-NR'-$, $-O-$, $-CO-$, $-OCO-$, $-OCONR'R''$ or $-CONR'R''-$;

L2 is a substituted or unsubstituted C1-C4 alkylene or C2-C4 alkenylene group;

A2 is a substituted or unsubstituted C6-C10 aryl or 5- to 12-membered-heterocyclyl group;

R2 is an unsubstituted or substituted group selected from C6-C10 aryl, a 5- to 12-membered heterocyclyl group, C1-C8 alkyl and C3-C6 cycloalkyl, or halogen;

R3, R4, R5 and R6 independently represent C6-C10 aryl, a 5- to 12-membered heterocyclyl group, $-$(C1-C4 alkylene)-(C6-C10 aryl), $-$(C1-C4 alkylene)-(5- to 12-membered heterocyclyl), hydrogen, halogen, C1-C8 alkyl, C2-C8 alkenyl, C2-C8 alkynyl, $-OR'$, $-CO_2R'$, $-CONR'R''$, $-COR'$, $-CN$, $-NO_2$, $-NR'R''$, $CF_3$, or $-Y-Z$;

R7 represents hydrogen, halogen, C1-C8 alkyl, C2-C8 alkenyl, C2-C8 alkynyl, —OR', —CO₂R', —CONR'R", —COR', —CN, —NO₂, —NR'R", CF₃, or —Y—Z;

Y is C1-C8 alkylene, C2-C8 alkenylene or C2-C8 alkynylene;

Z is halogen, C3-C6 cycloalkyl, —OR', —SR', —SOR', —SO₂R', —SO₂NR'R", —SO₃H, —NR'R", —NR'COR', —NO₂, —CO₂R', —CONR'R", —COR', —OCOR', —CN, —CF₃—NSO₂R', —OCONR'R" or —CR'=NOR"; and R' and R" independently represent hydrogen, C1-C8 alkyl, C2-C8 alkenyl or C2-C8 alkynyl, wherein the substituent(s) on any substituted alkyl, alkenyl or alkynyl group or moiety of R1 to R9, L2 or Y are selected from halogen, hydroxyl, amino, (C1-C4 alkyl)amino, di(C1-C4 alkyl)amino, C1-C4 alkoxy, CO₂H and —CO₂(C1-C4 alkyl);

the substituent(s) on any substituted cycloalkyl of R1, R2, R8 or Z are selected from C1-C8 alkyl, C2-C8 alkyl, C2-C8 alkenyl, C2-C8 alkynyl, Z and —Y—Z;

the substituent(s) on any substituted aryl or heterocyclyl group or moiety of R1, A1, A2 or R2 to R6 are selected from C1-C8 alkyl, C2-C8 alkenyl, C2-C8 alkynyl, unsubstituted phenyl, Z and —Y—Z, wherein any C1-C4 alkyl or C1-C4 alkoxy substituent on an aryl or heterocyclyl group or moiety may be further substituted with one, two or three unsubstituted groups selected from halogen, hydroxyl, amino, (C1-C4 alkyl)amino, di(C1-C4 alkyl)amino, C1-C4 alkoxy, cyano, —COR⁴¹ and —CO₂R⁴¹, wherein R⁴¹ is selected from hydrogen and C1-C4 alkyl, excluding:

6-Hydroxy-alpha-oxo-2-phenyl-3-indolizineacetic acid ethyl ester,

5-Methyl-alpha-oxo-2-phenyl-3-indolizineacetic acid ethyl ester, ethyl 2-(2,5-dimethylindolizin-3-yl)-2-oxoacetate, N,N-dimethyl-2-oxo-2-(2-phenyl-indolizin-3-yl)-acetamide, alpha-Oxo-2-phenyl-N-(4,5,6,7-tetrahydro-2-benzothiazolyl)-3-indolizineacetamide, N-Cyclohexyl-alpha-oxo-2-phenyl-3-indolizineacetamide, N-(2,4-Dimethyl-5-nitrophenyl)-alpha-oxo-2-phenyl-3-indolizineacetamide, N-[3-[(Diethylamino)sulfonyl]phenyl]-alpha-oxo-2-phenyl-3-indolizineacetamide, N-[2-[4-(Aminosulfonyl)phenyl]ethyl]-alpha-oxo-2-phenyl-3-indolizineacetamide, 2-Chloro-4-fluoro-benzoic acid 3-[[oxo-(2-phenyl-3-indolizinyl)acetyl]amino]propyl ester, N-[2-(1,1-Dimethylethyl)phenyl]-alpha-oxo-2-phenyl-3-indolizineacetamide, N-(3-Bromophenyl)-alpha-oxo-2-phenyl-3-indolizineacetamide, 3,5-Dimethyl-1-[oxo(2-phenyl-3-indolizinyl)acetyl]-piperidine, N-(2-Hydroxyethyl)-alpha-oxo-2-phenyl-3-indolizineacetamide, N-[2-[(4-Nitrobenzoyl)oxy]ethyl]-alpha-oxo-2-phenyl-3-indolizineacetamide, 2-(4-Chlorophenyl)-alpha-oxo-3-Indolizineacetic acid (2-fluorophenyl)methyl ester, 4-Fluoro-benzoic acid 2-[[[2-(4-chlorophenyl)-3-indolizinyl]oxoacetyl]amino]ethyl ester, 1-[[2-(4-Chlorophenyl)-3-indolizinyl]oxoacetyl]hexahydro-1H-azepine, 2-(4-Chlorophenyl)-alpha-oxo-3-indolizineacetic acid cyclopentyl ester, 2-(4-Chlorophenyl)-N-(2-hydroxyethyl)-alpha-oxo-3-indolizineacetamide, 4-(1,1-Dimethylethyl)-benzoic acid 2-[[[2-(4-chlorophenyl)-3-indolizinyl]oxoacetyl]amino]ethyl ester, 1-[Oxo(2-phenyl-3-indolizinyl)acetyl]-4-phenyl-piperazine, 2,6-Dimethyl-4-[oxo(2-phenyl-3-indolizinyl)acetyl]-morpholine, N-1,3-Benzodioxol-5-yl-2-(4-chlorophenyl)-alpha-oxo-3-indolizineacetamide, N-(4-Ethoxyphenyl)-alpha-oxo-2-phenyl-3-indolizineacetamide, N-(2,4-Dimethylphenyl)-alpha-oxo-2-phenyl-3-indolizineacetamide, N-(3-Hydroxypropyl)-alpha-oxo-2-phenyl-3-indolizineacetamide, N-Methyl-N-(1-methyl-4-piperidinyl)-alpha-oxo-2-phenyl-3-indolizineacetamide, N-[3-[(Diethylamino)sulfonyl]-4-methylphenyl]-alpha-oxo-2-phenyl-3-indolizineacetamide, N-(6-Methoxy-3-pyridinyl)-alpha-oxo-2-phenyl-3-indolizineacetamide, N-(3-Methoxyphenyl)-alpha-oxo-2-phenyl-3-indolizineacetamide, N-[4-Methyl-3-(4-morpholinylsulfonyl)phenyl]-alpha-oxo-2-phenyl-3-indolizineacetamide, alpha-Oxo-2-phenyl-N-[3-(1-piperidinylsulfonyl)phenyl]-3-indolizineacetamide, N-(4-Chloro-2-methoxy-5-methylphenyl)-alpha-oxo-2-phenyl-3-indolizineacetamide, N-(2-Chloro-3-pyridinyl)-alpha-oxo-2-phenyl-3-indolizineacetamide, N-[2-[[(4-Chlorophenyl)amino]carbonyl]phenyl]-alpha-oxo-2-phenyl-3-indolizineacetamide, N-[5-[(Diethylamino)sulfonyl]-2-(4-morpholinyl)phenyl]-alpha-oxo-2-phenyl-3-indolizineacetamide, alpha-Oxo-N-(3-phenoxyphenyl)-2-phenyl-3-indolizineacetamide, alpha-Oxo-2-phenyl-N-[4-(trifluoromethyl)phenyl]-3-indolizineacetamide, alpha-Oxo-2-phenyl-N-[4-(1-piperidinyl)phenyl]-3-indolizineacetamide, 4-Chloro-2-nitro-benzoic acid 3-[[oxo(2-phenyl-3-indolizinyl)acetyl]amino]propyl ester, 3-[(2,6-Dimethyl-4-morpholinyl)sulfonyl]-benzoic acid 3-[[oxo(2-phenyl-3-indolizinyl)acetyl]amino]propyl ester, N-(2,3-Dihydro-1,5-dimethyl-3-oxo-2-phenyl-1H-pyrazol-4-yl)-alpha-oxo-2-phenyl-3-indolizineacetamide, N-(3,5-Dimethoxyphenyl)-alpha-oxo-2-phenyl-3-indolizineacetamide, N-(3-Chloro-4-fluorophenyl)-alpha-oxo-2-phenyl-3-indolizineacetamide, N-[4-[(Diethylamino)sulfonyl]phenyl]-alpha-oxo-2-phenyl-3-indolizineacetamide, N-(3,4-Dimethylphenyl)-alpha-oxo-2-phenyl-3-indolizineacetamide, alpha-Oxo-N-(2-phenoxyphenyl)-2-phenyl-3-indolizineacetamide, N-[5-(1,1-Dimethylethyl)-2-methoxyphenyl]-alpha-oxo-2-phenyl-3-indolizineacetamide, alpha-Oxo-2-phenyl-N-[4-(1-piperidinylsulfonyl)phenyl]-3-indolizineacetamide, N-(2,3-Dimethylphenyl)-alpha-oxo-2-phenyl-3-indolizineacetamide, N-(4-Bromo-2-fluorophenyl)-alpha-oxo-2-phenyl-3-in-dolizineacetamide,
N-2-Naphthalenyl-alpha-oxo-2-phenyl-3-indolizineacetamide,
N-[2-Chloro-5-(4-morpholinylsulfonyl)phenyl]-alpha-oxo-2-phenyl-3-indolizineacetamide,
2,3-Dichloro-benzoic acid 3-[[oxo(2-phenyl-3-indolizinyl)acetyl]amino]propyl ester,
3,4-Dichloro-benzoic acid 3-[[oxo(2-phenyl-3-indolizinyl)acetyl]amino]propyl ester,
N-(2,4-Dimethoxyphenyl)-alpha-oxo-2-phenyl-3-indolizineacetamide,
2-(4-Chlorophenyl)-alpha-oxo-N-phenyl-3-indolizineacetamide,
4-[[2-(4-Chlorophenyl)-3-indolizinyl]oxoacetyl]-morpholine,
N-Ethyl-alpha-oxo-2-phenyl-3-indolizineacetamide,
alpha-Oxo-2-phenyl-N-[3-(trifluoromethyl)phenyl]-3-indolizineacetamide,
4-[[Oxo(2-phenyl-3-indolizinyl)acetyl]amino]-benzoic acid methyl ester,
N,N-Diethyl-alpha-oxo-2-phenyl-3-indolizineacetamide,
N-[2-(Dimethylamino)ethyl]-alpha-oxo-2-phenyl-3-indolizineacetamide,
2-Methyl-alpha-oxo-3-indolizineacetic acid,
N-(2-Methoxyphenyl)-alpha-oxo-2-phenyl-3-indolizineacetamide,
N-1-Naphthalenyl-alpha-oxo-2-phenyl-3-indolizineacetamide,
1,2,3,4-Tetrahydro-6,7-dimethoxy-2-[oxo(2-phenyl-3-indolizinyl)acetyl]-isoquinoline,
N-(1-Cyano-1-methylethyl)-alpha-oxo-2-phenyl-3-indolizineacetamide,
alpha-Oxo-2-phenyl-N-(2-phenylethyl)-3-indolizineacetamide,
Hexahydro-1-[oxo(2-phenyl-3-indolizinyl)acetyl]-1H-azepine,
alpha-Oxo-2-phenyl-N-4H-1,2,4-triazol-4-yl-3-indolizineacetamide,
1,2,3,4-Tetrahydro-1-[oxo(2-phenyl-3-indolizinyl)acetyl]-quinoline,
N-(6-Methoxy-2-benzothiazolyl)-alpha-oxo-2-phenyl-3-indolizineacetamide,
alpha-Oxo-2-phenyl-N-2-thiazolyl-3-indolizineacetamide,
N-[(4-Methoxyphenyl)methyl]-alpha-oxo-2-phenyl-3-indolizineacetamide,
N-[(4-Bromophenyl)methyl]-alpha-oxo-2-phenyl-3-indolizineacetamide,
N-(1,1-Dimethylethyl)-alpha-oxo-2-phenyl-3-indolizineacetamide,
N-Butyl-alpha-oxo-2-phenyl-3-indolizineacetamide,
alpha-Oxo-N-[(3-phenoxyphenyl)methyl]-2-phenyl-3-indolizineacetamide,
N-Ethyl-alpha-oxo-N,2-diphenyl-3-indolizineacetamide,
alpha-Oxo-N,2-diphenyl-3-indolizineacetamide,
N-[2-(3,4-Dimethoxyphenyl)ethyl]-alpha-oxo-2-phenyl-3-indolizineacetamide,
alpha-Oxo-2-phenyl-N-(phenylmethyl)-3-indolizineacetamide,
4-[Oxo(2-phenyl-3-indolizinyl)acetyl]-morpholine,
N-(4-Methylphenyl)-alpha-oxo-2-phenyl-3-indolizineacetamide,
2-Methyl-alpha-oxo-3-indolizineacetic acid ethyl ester,
N,N-Dimethyl-2-phenyl-3-indolizineglyoxylamide,
2-Oxo-2-(2-phenyl-indolizin-3-yl)-N-(4-trifluoromethylphenyl)-acetamide,
N-(2,4-Dichloro-phenyl)-2-oxo-2-(2-phenyl-indolizin-3-yl)-acetamide,
2-Oxo-2-(2-phenyl-indolizin-3-yl)-N-(3-trifluoromethyl-phenyl)-acetamide,
2-Oxo-2-(2-phenyl-indolizin-3-yl)-N-(4-piperidin-1-yl-phenyl)-acetamide
1-(5-methyl-2-phenyl-indolizin-3-yl)propane-1,2-dione
1-(5-methyl-2-phenyl-indolizin-3-yl)-propane-1,2-dione 1-oxime
1-(2,5-dimethyl-indolizin-3-yl)-2-phenyl-ethane-1,2-dione 1-oxime
1-(5-methyl-2-phenyl-indolizin-3-yl)-2-phenyl-ethane-1,2-dione 1-oxime
1-(2,5-dimethyl-indolizin-3-yl)-propane-1,2-dione 1-oxime
2-oxo-2-(2-phenylindolizin-3-yl)acetamide and their pharmaceutically or agriculturally acceptable salts thereof.

2. A compound according to claim 1 which is an indolizinyl derivative of formula (I) or a salt thereof:

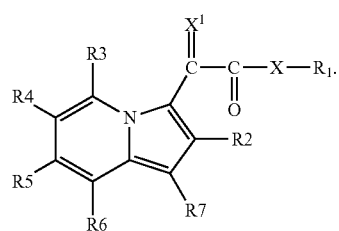

wherein:
R3, R4, R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, C1-C4 alkoxy, —$CO_2R'$, —CONR'R", —COR', CN, —$NO_2$, —NR'R", $CF_3$ or —Y—Z, with the proviso that when $X^1$ is O, X is —O—, R1 is ethyl and R4 to R7 are all hydrogen, R3 is not methyl; when $X^1$ is O, X is —NMe-, R1 is methyl, R2 is unsubstituted phenyl and R4 to R7 are all hydrogen, R3 is not hydrogen; when $X^1$ is O, X is —O—, R1 is hydrogen, R2 is methyl and R4 to R7 are all hydrogen, R3 is not hydrogen; or when $X^1$ is NOH, X is —NR8—, —O—, —S—, —SO— or —$SO_2$—.

3. A pharmaceutical composition comprising a compound as defined in claim 1 and a pharmaceutically acceptable carrier or diluent.

4. A composition comprising a compound as defined in claim 1 and an agriculturally acceptable carrier or diluent.

5. A method of treating a subject suffering from or susceptible to a fungal disease, which method comprises administering to said subject an effective amount of a compound which is an indolizinyl derivative of formula (I), or a pharmaceutically acceptable salt thereof:

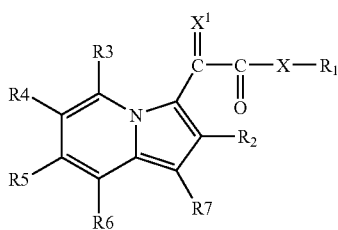

(I)

wherein:

X is a bond, —NR8—, —O—, —S—, —SO—, or —SO$_2$—;

X$^1$ is O or NOR9, wherein R9 is hydrogen or an unsubstituted or substituted C1-C4 alkyl group;

R1 represents an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', and —Y—Z;

R8 represents hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', and —Y—Z;

or when X is NR8, R1 and R8 together with the nitrogen to which they are attached may form an unsubstituted or substituted, aromatic or non-aromatic 5- to 12-membered heterocyclyl group;

A1 is an unsubstituted or substituted C6-C10 arylene group;

L1 is a bond, —NR'—, —O—, —CO—, —OCO—, —OCONR'R" or —CONR'R"—;

L2 is a substituted or unsubstituted C1-C4 alkylene or C2-C4 alkenylene group;

A2 is a substituted or unsubstituted C6-C10 aryl or 5- to 12-membered-heterocyclyl group;

R2 is an unsubstituted or substituted group selected from C6-C10 aryl, a 5- to 12-membered heterocyclyl group, C1-C8 alkyl and C3-C6 cycloalkyl, or halogen;

R3, R4, R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

R7 represents hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

Y is C1-C8 alkylene, C2-C8 alkenylene or C2-C8 alkynylene;

Z is halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$—NSO$_2$R', —OCONR'R" or —CR'=NOR"; and R' and R" independently represent hydrogen, C1-C8 alkyl, C2-C8 alkenyl or C2-C8 alkynyl, wherein the substituent(s) on any substituted alkyl, alkenyl or alkynyl group or moiety of R1 to R9, L2 or Y are selected from halogen, hydroxyl, amino, (C1-C4 alkyl)amino, di(C1-C4 alkyl)amino, C1-C4 alkoxy, CO$_2$H and —CO$_2$(C1-C4 alkyl);

the substituent(s) on any substituted cycloalkyl of R1, R2, R8 or Z are selected from C1-C8 alkyl, C2-C8 alkyl, C2-C8 alkenyl, C2-C8 alkynyl, Z and —Y—Z;

the substituent(s) on any substituted aryl or heterocyclyl group or moiety of R1, A1, A2 or R2 to R6 are selected from C1-C8 alkyl, C2-C8 alkenyl, C2-C8 alkynyl, unsubstituted phenyl, Z and —Y—Z, wherein any C1-C4 alkyl or C1-C4 alkoxy substituent on an aryl or heterocyclyl group or moiety may be further substituted with one, two or three unsubstituted groups selected from halogen, hydroxyl, amino, (C1-C4 alkyl)amino, di(C1-C4 alkyl)amino, C1-C4 alkoxy, cyano, —COR$^{41}$ and —CO$_2$R$^{41}$, wherein R$^{41}$ is selected from hydrogen and C1-C4 alkyl, excluding:

6-Hydroxy-alpha-oxo-2-phenyl-3-indolizineacetic acid ethyl ester,

5-Methyl-alpha-oxo-2-phenyl-3-indolizineacetic acid ethyl ester, ethyl 2-(2,5-dimethylindolizin-3-yl)-2-oxoacetate, N,N-dimethyl-2-oxo-2-(2-phenyl-indolizin-3-yl)-acetamide, alpha-Oxo-2-phenyl-N-(4,5,6,7-tetrahydro-2-benzothiazolyl)-3-indolizineacetamide, N-Cyclohexyl-alpha-oxo-2-phenyl-3-indolizineacetamide, N-(2,4-Dimethyl-5-nitrophenyl)-alpha-oxo-2-phenyl-3-indolizineacetamide, N-[3-[(Diethylamino)sulfonyl]phenyl]-alpha-oxo-2-phenyl-3-indolizineacetamide, N-[2-[4-(Aminosulfonyl)phenyl]ethyl]-alpha-oxo-2-phenyl-3-indolizineacetamide, 2-Chloro-4-fluoro-benzoic acid 3-[[oxo-(2-phenyl-3-indolizinyl)acetyl]amino]propyl ester, N-[2-(1,1-Dimethylethyl)phenyl]-alpha-oxo-2-phenyl-3-indolizineacetamide, N-(3-Bromophenyl)-alpha-oxo-2-phenyl-3-indolizineacetamide, 3,5-Dimethyl-1-[oxo(2-phenyl-3-indolizinyl)acetyl]-piperidine, N-(2-Hydroxyethyl)-alpha-oxo-2-phenyl-3-indolizineacetamide, N-[2-[(4-Nitrobenzoyl)oxy]ethyl]-alpha-oxo-2-phenyl-3-indolizineacetamide, 2-(4-Chlorophenyl)-alpha-oxo-3-Indolizineacetic acid (2-fluorophenyl)methyl ester, 4-Fluoro-benzoic acid 2-[[[2-(4-chlorophenyl)-3-indolizinyl]oxoacetyl]amino]ethyl ester, 1-[[2-(4-Chlorophenyl)-3-indolizinyl]oxoacetyl]hexahydro-1H-azepine, 2-(4-Chlorophenyl)-alpha-oxo-3-indolizineacetic acid cyclopentyl ester, 2-(4-Chlorophenyl)-N-(2-hydroxyethyl)-alpha-oxo-3-indolizineacetamide, 4-(1,1-Dimethylethyl)-benzoic acid 2-[[[2-(4-chlorophenyl)-3-indolizinyl]oxoacetyl]amino]ethyl ester, 1-[Oxo(2-phenyl-3-indolizinyl)acetyl]-4-phenyl-piperazine, 2,6-Dimethyl-4-[oxo(2-phenyl-3-indolizinyl)acetyl]-morpholine, N-1,3-Benzodioxol-5-yl-2-(4-chlorophenyl)-alpha-oxo-3-indolizineacetamide, N-(4-Ethoxyphenyl)-alpha-oxo-2-phenyl-3-indolizineacetamide, N-(2,4-Dimethylphenyl)-alpha-oxo-2-phenyl-3-indolizineacetamide, N-(3-Hydroxypropyl)-alpha-oxo-2-phenyl-3-indolizineacetamide,
N-Methyl-N-(1-methyl-4-piperidinyl)-alpha-oxo-2-phenyl-3-indolizineacetamide,
N-[3-[(Diethylamino)sulfonyl]-4-methylphenyl]-alpha-oxo-2-phenyl-3-indolizineacetamide,
N-(6-Methoxy-3-pyridinyl)-alpha-oxo-2-phenyl-3-indolizineacetamide,
N-(3-Methoxyphenyl)-alpha-oxo-2-phenyl-3-indolizineacetamide,
N-[4-Methyl-3-(4-morpholinylsulfonyl)phenyl]-alpha-oxo-2-phenyl-3-indolizineacetamide,
alpha-Oxo-2-phenyl-N-[3-(1-piperidinylsulfonyl)phenyl]-3-indolizineacetamide,
N-(4-Chloro-2-methoxy-5-methylphenyl)-alpha-oxo-2-phenyl-3-indolizineacetamide,
N-(2-Chloro-3-pyridinyl)-alpha-oxo-2-phenyl-3-indolizineacetamide,
N-[2-[[(4-Chlorophenyl)amino]carbonyl]phenyl]-alpha-oxo-2-phenyl-3-indolizineacetamide,
N-[5-[(Diethylamino)sulfonyl]-2-(4-morpholinyl)phenyl]-alpha-oxo-2-phenyl-3-indolizineacetamide,
alpha-Oxo-N-(3-phenoxyphenyl)-2-phenyl-3-indolizineacetamide,
alpha-Oxo-2-phenyl-N-[4-(trifluoromethyl)phenyl]-3-indolizineacetamide,
alpha-Oxo-2-phenyl-N-[4(1-piperidinyl)phenyl]-3-indolizineacetamide,
4-Chloro-2-nitro-benzoic acid 3-[[oxo(2-phenyl-3-indolizinyl)acetyl]amino]propyl ester,
3-[(2,6-Dimethyl-4-morpholinyl)sulfonyl]-benzoic acid 3-[[oxo(2-phenyl-3-indolizinyl)acetyl]amino]propyl ester,
N-(2,3-Dihydro-1,5-dimethyl-3-oxo-2-phenyl-1H-pyrazol-4-yl)-alpha-oxo-2-phenyl-3-indolizineacetamide,
N-(3,5-Dimethoxyphenyl)-alpha-oxo-2-phenyl-3-indolizineacetamide,
N-(3-Chloro-4-fluorophenyl)-alpha-oxo-2-phenyl-3-indolizineacetamide,
N-[4-[(Diethylamino)sulfonyl]phenyl]-alpha-oxo-2-phenyl-3-indolizineacetamide,
N-(3,4-Dimethylphenyl)-alpha-oxo-2-phenyl-3-indolizineacetamide,
alpha-Oxo-N-(2-phenoxyphenyl)-2-phenyl-3-indolizineacetamide,
N-[5-(1,1-Dimethylethyl)-2-methoxyphenyl]-alpha-oxo-2-phenyl-3-indolizineacetamide,
alpha-Oxo-2-phenyl-N-[4-(1-piperidinylsulfonyl)phenyl]-3-indolizineacetamide,
N-(2,3-Dimethylphenyl)-alpha-oxo-2-phenyl-3-indolizineacetamide,
N-(4-Bromo-2-fluorophenyl)-alpha-oxo-2-phenyl-3-indolizineacetamide,
N-2-Naphthalenyl-alpha-oxo-2-phenyl-3-indolizineacetamide,
N-[2-Chloro-5-(4-morpholinylsulfonyl)phenyl]-alpha-oxo-2-phenyl-3-indolizineacetamide,
2,3-Dichloro-benzoic acid 3-[[oxo(2-phenyl-3-indolizinyl)acetyl]amino]propyl ester,
3,4-Dichloro-benzoic acid 3-[[oxo(2-phenyl-3-indolizinyl)acetyl]amino]propyl ester,
N-(2,4-Dimethoxyphenyl)-alpha-oxo-2-phenyl-3-indolizineacetamide,
2-(4-Chlorophenyl)-alpha-oxo-N-phenyl-3-indolizineacetamide,
4-[[2-(4-Chlorophenyl)-3-indolizinyl]oxoacetyl]-morpholine,
N-Ethyl-alpha-oxo-2-phenyl-3-indolizineacetamide,
alpha-Oxo-2-phenyl-N-[3-(trifluoromethyl)phenyl]-3-indolizineacetamide,
4-[[Oxo(2-phenyl-3-indolizinyl)acetyl]amino]-benzoic acid methyl ester,
N,N-Diethyl-alpha-oxo-2-phenyl-3-indolizineacetamide,
N-[2-(Dimethylamino)ethyl]-alpha-oxo-2-phenyl-3-indolizineacetamide,
2-Methyl-alpha-oxo-3-indolizineacetic acid,
N-(2-Methoxyphenyl)-alpha-oxo-2-phenyl-3-indolizineacetamide,
N-1-Naphthalenyl-alpha-oxo-2-phenyl-3-indolizineacetamide,
1,2,3,4-Tetrahydro-6,7-dimethoxy-2-[oxo(2-phenyl-3-indolizinyl)acetyl]-isoquinoline,
N-(1-Cyano-1-methylethyl)-alpha-oxo-2-phenyl-3-indolizineacetamide,
alpha-Oxo-2-phenyl-N-(2-phenylethyl)-3-indolizineacetamide,
Hexahydro-1-[oxo(2-phenyl-3-indolizinyl)acetyl]-1H-azepine,
alpha-Oxo-2-phenyl-N-4H-1,2,4-triazol-4-yl-3-indolizineacetamide,
1,2,3,4-Tetrahydro-1-[oxo(2-phenyl-3-indolizinyl)acetyl]-quinoline,
N-(6-Methoxy-2-benzothiazolyl)-alpha-oxo-2-phenyl-3-indolizineacetamide,
alpha-Oxo-2-phenyl-N-2-thiazolyl-3-indolizineacetamide,
N-[(4-Methoxyphenyl)methyl]-alpha-oxo-2-phenyl-3-indolizineacetamide,
N-[(4-Bromophenyl)methyl]-alpha-oxo-2-phenyl-3-indolizineacetamide,
N-(1,1-Dimethylethyl)-alpha-oxo-2-phenyl-3-indolizineacetamide,
N-Butyl-alpha-oxo-2-phenyl-3-indolizineacetamide,
alpha-Oxo-N-[(3-phenoxyphenyl)methyl]-2-phenyl-3-indolizineacetamide,
N-Ethyl-alpha-oxo-N,2-diphenyl-3-indolizineacetamide,
alpha-Oxo-N,2-diphenyl-3-indolizineacetamide,
N-[2-(3,4-Dimethoxyphenyl)ethyl]-alpha-oxo-2-phenyl-3-indolizineacetamide,
alpha-Oxo-2-phenyl-N-(phenylmethyl)-3-indolizineacetamide,
4-[Oxo(2-phenyl-3-indolizinyl)acetyl]-morpholine,
N-(4-Methylphenyl)-alpha-oxo-2-phenyl-3-indolizineacetamide,
2-Methyl-alpha-oxo-3-indolizineacetic acid ethyl ester,
N,N-Dimethyl-2-phenyl-3-indolizineglyoxylamide,
2-Oxo-2-(2-phenyl-indolizin-3-yl)-N-(4-trifluoromethylphenyl)-acetamide,
N-(2,4-Dichloro-phenyl)-2-oxo-2-(2-phenyl-indolizin-3-yl)-acetamide,
2-Oxo-2-(2-phenyl-indolizin-3-yl)-N-(3-trifluoromethylphenyl)-acetamide,
2-Oxo-2-(2-phenyl-indolizin-3-yl)-N-(4-piperidin-1-yl-phenyl)-acetamide
1-(5-methyl-2-phenyl-indolizin-3-yl)propane-1,2-dione
1-(5-methyl-2-phenyl-indolizin-3-yl)-propane-1,2-dione 1-oxime
1-(2,5-dimethyl-indolizin-3-yl)-2-phenyl-ethane-1,2-dione 1-oxime
1-(5-methyl-2-phenyl-indolizin-3-yl)-2-phenyl-ethane-1,2-dione 1-oxime
1-(2,5-dimethyl-indolizin-3-yl)-propane-1,2-dione 1-oxime 2-Oxo-2-(2-phenylindolizin-3-yl)acetamide and their pharmaceutically or agriculturally acceptable salts thereof.

6. A method according to claim 5, wherein X is —NR8- or —O—.

7. A method according to claim 5, wherein X is —NR8-.

8. A method according to claim 5 wherein R1 is phenyl, pyridinyl, thiophenyl, furanyl, benzimidazolyl, indolyl, dihydroindolyl, unsubstituted C5-C6 cycloalkyl, C1-C4 alkyl which is unsubstituted or substituted with C1-C4 alkoxy or —$CO_2$(C1-C4 alkyl), -A1-L1-A2 or -L2-A2, wherein the aryl and heterocyclyl groups are unsubstituted or substituted with one, two or three substituents selected from the unsubstituted groups halogen, —$CO_2$R', —CONR'R", OCOR', hydroxyl, cyano, —NR'R", —COR', —$NSO_2$R', —O(C2-C4 alkenyl), C2-C4 alkenyl, —$SO_2$R', —OCONR'R" and —CR'=NOR", and from C1-C4 alkyl and C1-C4 alkoxy groups which are unsubstituted or substituted with from one to four unsubstituted groups selected from halogen, hydroxyl, di(C1-C4 alkyl)amino, cyano, —COR' and —$CO_2$R', wherein R' and R" are independently selected from hydrogen and C1-C4 alkyl.

9. A method according to claim 5, wherein A1 is unsubstituted phenyl or phenyl substituted with a group —NR'R", wherein R' and R" are independently selected from hydrogen and C1-C4 alkyl; L1 is a bond, —NH— or —CONR'R"—, wherein R' and R" are independently selected from hydrogen and C1-C4 alkyl groups and moieties; L2 is C1-C4 alkylene which is unsubstituted or substituted with one or two substituents selected from halogen, C1-C4 alkoxy and —$CO_2$(C1-C4 alkyl); and A2 is phenyl or a 5- to 6-membered heterocyclyl group containing one, two, three or four heteroatoms selected from N, O and S, wherein the heterocycle is unsubstituted or substituted with one or two substituents selected from C1-C4 alkyl and $CO_2$(C1-C4 alkyl).

10. A method according to claim 5 wherein R2 is phenyl or pyridinyl optionally substituted with halogen, unsubstituted C1-C4 alkyl, unsubstituted C1-C4 alkoxy or cyano, or unsubstituted thiophenyl or furanyl.

11. A method according to claim 10, wherein X is NR8 and R3, R4, R5, R6 and R7 are selected from hydrogen, halogen, C1-C4 alkyl or C1-C4 alkoxy.

12. A method according to claim 5, wherein X is NR8 and R8 is hydrogen or unsubstituted C1-C4 alkyl.

13. A method according to claim 5, wherein
X is —NR8— or —O—;
$X^1$ is O or NOR9, wherein R9 is a linear C1-C4 alkyl group which is unsubstituted or substituted with a single substituent on the terminal carbon atom, the substituent being selected from di(C1-C4 alkyl)amino and —$CO_2$H;
R1 is phenyl, pyridinyl, thiophenyl, furanyl, benzimidazolyl, indolyl, dihydroindolyl, unsubstituted C5-C6 cycloalkyl, C1-C4 alkyl which is unsubstituted or substituted with C1-C4 alkoxy or —$CO_2$(C1-C4 alkyl), -A1-L1-A2 or -L2-A2, wherein the aryl and heterocyclyl groups are unsubstituted or substituted with one, two or three substituents selected from the unsubstituted groups halogen, —$CO_2$R', —CONR'R", OCOR', hydroxyl, cyano, —NR'R", —COR', —$NSO_2$R', —O(C2-C4 alkenyl), C2-C4 alkenyl, —$SO_2$R', —OCONR'R" and —CR'=NOR", and from C1-C4 alkyl and C1-C4 alkoxy groups which are unsubstituted or substituted with from one to four unsubstituted groups selected from halogen, hydroxyl, di(C1-C4 alkyl)amino, cyano, —COR' and —$CO_2$R', wherein R' and R" are independently selected from hydrogen and C1-C4 alkyl;

A1 is unsubstituted phenyl or phenyl substituted with a group —NR'R", wherein R' and R" are independently selected from hydrogen and C1-C4 alkyl;

L1 is a bond, —NH— or —CONR'R"—, wherein R' and R" are independently selected from hydrogen and C1-C4 alkyl groups and moieties;

L2 is C1-C4 alkylene which is unsubstituted or substituted with one or two substituents selected from halogen, C1-C4 alkoxy and —$CO_2$(C1-C4 alkyl);

A2 is phenyl or a 5- to 6-membered heterocyclyl group containing one, two, three or four heteroatoms selected from N, O and S, wherein the heterocycle is unsubstituted or substituted with one or two substituents selected from C1-C4 alkyl and $CO_2$(C1-C4 alkyl);

R8 is hydrogen or unsubstituted C1-C4 alkyl; or when X is NR8, R1 and R8 together with the nitrogen atom to which they are attached may form a 5- to 12-membered heterocyclyl group preferably selected from piperidinyl, morpholinyl, azepanyl or dihydroindolyl;

R2 is unsubstituted or substituted phenyl, unsubstituted or substituted pyridinyl, or unsubstituted thiophenyl or furanyl, the substituents being selected from halogen, unsubstituted C1-C4 alkyl, unsubstituted C1-C4 alkoxy and cyano;

R3 to R6 are independently selected from hydrogen, unsubstituted C1-C4 alkyl and unsubstituted C1-C4 alkoxy; and R7 is hydrogen.

14. A method according to claim 5 wherein the compound is:
N-(2-Methoxy-phenyl)-2-oxo-2-(2-phenyl-indolizin-3-yl)-acetamide,
4-[2-Oxo-2-(2-phenyl-indolizin-3-yl)-acetylamine]-benzoic acid methyl ester,
2-Oxo-N-phenyl-2-(2-phenyl-indolizin-3-yl)-acetamide,
4-[2-Oxo-2-(-phenyl-indolizin-3-yl)-acetylamino]-benzoic acid propyl ester,
2-[2-Oxo-2-(2-phenyl-indolizin-3-yl)-acetylamine]-benzoic acid methyl ester,
3-[2-Oxo-2-(2-phenyl-indolizin-3-yl)-acetylamine]-benzoic acid methyl ester,
4-[2-Oxo-2-(-phenyl-indolizin-3-yl)-acetylamino]-benzoic acid propyl ester,
4-[2-Oxo-2-(2-phenyl-indolizin-3-yl)-acetylamino]-benzoic acid butyl ester,
N-(3-Methoxy-phenyl)-2-oxo-2-(2-phenyl-indolizin-3-yl)-acetamide,
N-(4-Methoxy-phenyl)-2-oxo-2-(2-phenyl-indolizin-3-yl)-acetamide,
N-(4-Hydroxy-phenyl)-2-oxo-2-(2-phenyl-indolizin-3-yl)-acetamide,
N-(4-Chloro-phenyl)-2-oxo-2-(2-phenyl-indolizin-3-yl)-acetamide,
N-(4-Cyano-phenyl)-2-oxo-2-(2-phenyl-indolizin-3-yl)-acetamide,
2-Oxo-2-(2-phenyl-indolizin-3-yl)-N-p-tolyl-acetamide,
2-Oxo-2-(2-phenyl-indolizin-3-yl)-N-pyridin-4-yl-acetamide,
2-Oxo-2-(2-phenyl-indolizin-3-yl)-N-pyridin-3-yl-acetamide,
2-Oxo-2-(2-phenyl-indolizin-3-yl)-N-pyridin-2-yl-acetamide,
4-[2-Oxo-2-(2-phenyl-indolizin-3-yl)-acetylamine]-benzoic acid, N-(2,4-Dimethoxy-phenyl-phenyl)-2-oxo-2-(2-phenyl-indolizin-3-yl)-acetamide,
N-(6-Methoxy-pyridin-3-yl)-2-oxo-2-(2-phenyl-indolizin-3-yl)-acetamide,
4-[2-Oxo-2-(2-phenyl-indolizin-3-yl)-acetylamine]-benzamide,
N-Methyl-4-[2-oxo-2-(2-phenyl-indolizin-3-yl)-acetylamino]-benzamide,
N,N-Dimethyl-4-[2-oxo-2-(2-phenyl-indolizin-3-yl)-acetamino]-benzamide,
5-[2-Oxo-2-(2-phenyl-indolizin-3-yl)-acetylamino]-thiophene-3-carboxylic acid methyl ester,
N-(4-Methoxy-phenyl)-2-oxo-2-(2-pyridin-4-yl-indolizin-3-yl)-acetamide,
N-(4-Methoxy-phenyl)-2-oxo-2-(2-pyridin-3-yl-indolizin-3-yl)-acetamide,
N-(4-Methoxy-phenyl)-2-oxo-2-(2-pyridin-2-yl-indolizin-3-yl)-acetamide,
N-(4-Methoxy-phenyl)-2-oxo-2-(2-thiophen-2-yl-indolizin-3-yl)-acetamide,
2-(2-Furan-2-yl-indolizin-3-yl)-N-(4-methoxy-phenyl)-2-oxo-acetamide,
2-[2-(4-Fluoro-phenyl)-indolizin-3-yl]-N-(4-methoxy-phenyl)-2-oxo-acetamide,
2-[2-(4-Fluoro-phenyl)-indolizin-3-yl]-2-oxo-N-p-tolyl-acetamide,
N-(2-,4-Dimethoxy-phenyl)-2-[2-(4-fluoro-phenyl)-indolizin-3-yl]-2-oxo-acetamide,
2-[2-(4-Fluoro-phenyl)-indolizin-3-yl]-N-(6-methoxy-pyridin-3-yl)-2-oxo-acetamide,
2-Oxo-2-(2-thiophen-2-yl-indolizin-3-yl)-N-p-tolyl-acetamide,
N-(2,4-Dimethoxy-phenyl)-2-oxo-2-(2-thiophen-2-yl-indolizin-3-yl)-acetamide,
N-(6-Methoxy-pyridin-3-yl)-2-oxo-2-(2-thiophen-2-yl-indolizin-3-yl)-acetamide,
2-(2-Furan-2-yl-indolizin-3-yl)-2-oxo-N-p-tolyl-acetamide,
N-(2,4-Dimethoxy-phenyl)-2-(2-furan-2-yl-indolizin-3-yl)-2-oxo-acetamide,
2-(2-Furan-2-yl-indolizin-3-yl)-N-(6-methoxy-pyridin-3-yl)-2-oxo-acetamide,
2-Oxo-2-(2-pyridin-4-yl-indolizin-3-yl)-N-p-tolyl-acetamide,
N-(2,4-Dimethoxy-phenyl)-2-oxo-2-(2-pyridin-4-yl-indolizin-3-yl)-acetamide,
N-(6-Methoxy-pyridin-3-yl)-2-oxo-2-(2-pyridin-4-yl-indolizin-3-yl)-acetamide,
2-Oxo-2-(2-pyridin-3-yl-indolizin-3-yl)-N-p-tolyl-acetamide,
N-(2,4-Dimethoxy-phenyl)-2-oxo-2-(2-pyridin-3-yl-indolizin-3-yl)-acetamide,
N-(6-Methoxy-pyridin-3-yl)-2-oxo-2-(2-pyridin-3-yl-indolizin-3-yl)-acetamide,
2-Oxo-2-(2-pyridin-2-yl-indolizin-3-yl)-N-p-tolyl-acetamide,
N-(2,4-Dimethoxy-phenyl)-2-oxo-2-(2-pyridin-2-yl-indolizin-3-yl)-acetamide,
N-(6-Methoxy-pyridin-3-yl)-2-oxo-2-(2-pyridin-2-yl-indolizin-3-yl)-acetamide,
Oxo-(2-phenyl-indolizin-3-yl)-thioacetic acid S-(2-methoxy-phenyl)ester,
4-[2-Oxo-2-(2-phenyl-indolizin-3-yl)-acetoxy]-benzoic acid methyl ester,
N-Cyclohexyl-2-oxo-2-(2-phenyl-indolizin-3-yl)-acetamide,
N-Methyl-2-oxo-2-(2-phenyl-indolizin-3-yl)-acetamide,
N-Isopropyl-2-oxo-2-(2-phenyl-indolizin-3-yl)-acetamide,
N-(2-Methoxy-ethyl)-2-oxo-2-(2-phenyl-indolizin-3-yl)-acetamide,
N-Benzyl-2-oxo-2-(2-phenyl-indolizin-3-yl)-acetamide,
N,N-Dimethyl-2-oxo-2-(2-phenyl-indolizin-3-yl)-acetamide,
1-(2-Phenyl-indolizin-3-yl)-2-piperidin-1-yl-ethane-1,2-dione,
N-(2-Methoxy-ethyl)-2-oxo-2-(2-pyridin-3-yl-indolizin-3-yl)-acetamide,
N-Methyl-2-oxo-N-phenyl-2-(2-phenyl-indolizin-3-yl)-acetamide,
N-Methyl-2-oxo-N-phenyl-2-(2-pyridin-3-yl-indolizin-3-yl)-acetamide,
2-(5-Methyl-2-phenyl-indolizin-3-yl)-2-oxo-N-p-tolyl-acetamide,
N-(6-Methoxy-pyridin-3-yl)-2-(5-methyl-2-phenyl-indolizin-3-yl)-2-oxo-acetamide,
2-(6-Methyl-2-phenyl-indolizin-3-yl)-2-oxo-N-p-tolyl-acetamide,
2-(7-Methyl-2-phenyl-indolizin-3-yl)-2-oxo-N-p-tolyl-acetamide,
N-(6-Methoxy-pyridin-3-yl)-2-(6-methyl-2-phenyl-indolizin-3-yl)-2-oxo-acetamide,
N-(6-Methoxy-pyridin-3-yl)-2-(7-methyl-2-phenyl-indolizin-3-yl)-2-oxo-acetamide,
N-(6-Methoxy-pyridin-3-yl)-2-(8-methyl-2-phenyl-indolizin-3-yl)-2-oxo-acetamide,
2-(6-Methoxy-2-phenyl-indolizin-3-yl)-N-(6-methoxy-pyridin-3-yl)-2-oxo-acetamide,
2-(6-Methoxy-2-phenyl-indolizin-3-yl)-2-oxo-N-p-tolyl-acetamide,
N-(4-Chloro-phenyl)-2-oxo-2-(2-pyridin-3-yl-indolizin-3-yl)-acetamide,
N-(4-Fluoro-phenyl)-2-oxo-2-(2-pyridin-3-yl-indolizin-3-yl)-acetamide,
2-(6-Methyl-2-pyridin-3-yl-indolizin-3-yl)-2-oxo-N-p-tolyl-acetamide,
N-(4-Fluoro-phenyl)-2-oxo-2-(2-phenyl-indolizin-3-yl)-acetamide,
N-(2-Fluoro-phenyl)-2-oxo-2-(2-phenyl-indolizin-3-yl)-acetamide,
2-Oxo-2-(2-phenyl-indolizin-3-yl)-N-(4-trifluoromethyl-phenyl)-acetamide,
2-Oxo-2-(2-phenyl-indolizin-3-yl)-N-o-tolyl-acetamide,
N-(4-Dimethylamino-phenyl)-2-oxo-2-(2-phenyl-indolizin-3-yl)-acetamide,
N-(4-Bromo-phenyl)-2-oxo-2-(2-phenyl-indolizin-3-yl)-acetamide,
N-(4-Acetyl-phenyl)-2-oxo-2-(2-phenyl-indolizin-3-yl)-acetamide,
2-Oxo-2-(2-phenyl-indolizin-3-yl)-N-m-tolyl-acetamide,
N-(2-Chloro-phenyl)-2-oxo-2-(2-phenyl-indolizin-3-yl)-acetamide,
2-[2-Oxo-2-(2-phenyl-indolizin-3-yl)-acetylamino]-benzoic acid ethyl ester,
N-(2,4-Dichloro-phenyl)-2-oxo-2-(2-phenyl-indolizin-3-yl)-acetamide,
N-(4-Fluoro-phenyl)-2-[2-(4-fluoro-phenyl)-indolizin-3-yl]-2-oxo-acetamide,
N-(4-Chloro-phenyl)-2-[2-(4-fluoro-phenyl)-indolizin-3-yl]-2-oxo-acetamide,
N-(2-Fluoro-phenyl)-2-oxo-2-(2-pyridin-3-yl-indolizin-3-yl)-acetamide,
2-Oxo-2-(2-pyridin-3-yl-indolizin-3-yl)-N-(4-trifluoromethyl-phenyl)-acetamide, 2-Oxo-2-(2-pyridin-3-yl-indolizin-3-yl)-N-o-tolyl-acetamide,
N-(4-Bromo-phenyl)-2-oxo-2-(2-pyridin-3-yl-indolizin-3-yl)-acetamide,
2-Oxo-2-(2-pyridin-3-yl-indolizin-3-yl)-N-m-tolyl-acetamide,
N-(2-Chloro-phenyl)-2-oxo-2-(2-pyridin-3-yl-indolizin-3-yl)-acetamide,
N-(4-Acetyl-phenyl)-2-oxo-2-(2-pyridin-3-yl-indolizin-3-yl)-acetamide,
2-Oxo-2-(2-phenyl-indolizin-3-yl)-N-(3-trifluoromethyl-phenyl)-acetamide,
1-(2,3-Dihydro-indol-1-yl)-2-(2-phenyl-indolizin-3-yl)-ethane-1,2-dione,
N-(4-Methanesulfonylamino-phenyl)-2-oxo-2-(2-phenyl-indolizin-3-yl)-acetamide,
N-(3,5-Dichloro-phenyl)-2-oxo-2-(2-phenyl-indolizin-3-yl)-acetamide,
N-[4-(Cyano-dimethyl-methyl)-phenyl]-2-oxo-2-(2-phenyl-indolizin-3-yl)-acetamide,
2-Oxo-2-(2-phenyl-indolizin-3-yl)-N-(3,4,5-trimethoxy-phenyl)-acetamide,
2-Oxo-2-(2-pyridin-3-yl-indolizin-3-yl)-N-(3-trifluoromethyl-phenyl)-acetamide,
N-(2,4-Dichloro-phenyl)-2-oxo-2-(2-pyridin-3-yl-indolizin-3-yl)-acetamide,
N-[4-(Cyano-dimethyl-methyl)-phenyl]-2-oxo-2-(2-pyridin-3-yl-indolizin-3-yl)-acetamide,
2-Oxo-2-(2-pyridin-3-yl-indolizin-3-yl)-N-(3,4,5-trimethoxy-phenyl)-acetamide,
N-(3,5-Dichloro-phenyl)-2-oxo-2-(2-pyridin-3-yl-indolizin-3-yl)-acetamide,
N-[3-(Cyano-dimethyl-methyl)-phenyl]-2-oxo-2-(2-phenyl-indolizin-3-yl)-acetamide,
N-(6-Dimethylamino-pyridin-3-yl)-2-oxo-2-(2-phenyl-indolizin-3-yl)-acetamide,
N-(4-Dimethylamino-phenyl)-2-oxo-2-(2-pyridin-3-yl-indolizin-3-yl)-acetamide,
N-[3-(Cyano-dimethyl-methyl)-phenyl]-2-oxo-2-(2-pyridin-3-yl-indolizin-3-yl)-acetamide,
2-[(E/Z)-Methoxyimino]-N-(4-methoxy-phenyl)-2-(2-phenyl-indolizin-3-yl)-acetamide,
N-(4-Methoxy-phenyl)-2-oxo-2-(2-o-tolyl-indolizin-3-yl)-acetamide,
N-(4-Methoxy-phenyl)-2-oxo-2-(2-m-tolyl-indolizin-3-yl)-acetamide,
N-(4-Methoxy-phenyl)-2-(8-methyl-2-phenyl-indolizin-3-yl)-2-oxo-acetamide,
2-[2-(3-Chloro-phenyl)-indolizin-3-yl]-N-(4-methoxy-phenyl)-2-oxo-acetamide,
2-[2-(3-Cyano-phenyl)-indolizin-3-yl]-N-(4-methoxy-phenyl)-2-oxo-acetamide,
N-(4-Methoxy-phenyl)-2-(5-methyl-2-phenyl-indolizin-3-yl)-2-oxo-acetamide,
N-(4-Methoxy-phenyl)-2-oxo-2-(2-p-tolyl-indolizin-3-yl)-acetamide,
N-(4-Methoxy-phenyl)-2-(6-methoxy-2-phenyl-indolizin-3-yl)-2-oxo-acetamide,
N-[3-(2-Dimethylamino-ethoxy)-phenyl]-2-oxo-2-(2-phenyl-indolizin-3-yl)-acetamide,
N-(3-Methyl-3H-benzoimidazol-5-yl)-2-oxo-2-(2-phenyl-indolizin-3-yl)-acetamide,
N-(1-Methyl-1H-benzoimidazol-5-yl)-2-oxo-2-(2-phenyl-indolizin-3-yl)-acetamide,
N-(4-Dimethylamino-phenyl)-2-(6-methoxy-2-phenyl-indolizin-3-yl)-2-oxo-acetamide,
N-(4-{1-[(E/Z)-Methoxyimino]-ethyl}-phenyl)-2-oxo-2-(2-phenyl-indolizin-3-yl)-acetamide,
N-(2,4-Difluoro-phenyl)-2-[2-(3-fluoro-phenyl)-indolizin-3-yl]-2-oxo-acetamide,
2-[2-(3-Cyano-phenyl)-indolizin-3-yl]-N-(2,4-difluoro-phenyl)-2-oxo-acetamide,
N-(5-Chloro-2-methyl-phenyl)-2-oxo-2-(2-phenyl-indolizin-3-yl)-acetamide,
{3-[2-Oxo-2-(2-phenyl-indolizin-3-yl)-acetylamino]-phenoxy}-acetic acid,
N-(2-Allyloxy-4-fluoro-phenyl)-2-oxo-2-(2-phenyl-indolizin-3-yl)-acetamide,
2-Methyl-2-[2-oxo-2-(2-phenyl-indolizin-3-yl)-acetylamino]-propionic acid ethyl ester,
2-Methyl-2-[2-oxo-2-(2-phenyl-indolizin-3-yl)-acetylamino]-3-phenyl-propionic acid ethyl ester,
N-(4-{1-[(E/Z)-Hydroxyimino]-ethyl}-phenyl)-2-oxo-2-(2-phenyl-indolizin-3-yl)-acetamide,
2-Oxo-2-(2-phenyl-indolizin-3-yl)-N-(4-piperidin-1-yl-phenyl)-acetamide,
N-(4-Morpholin-4-yl-phenyl)-2-oxo-2-(2-phenyl-indolizin-3-yl)-acetamide,
N-(4-Isopropyl-phenyl)-2-oxo-2-(2-phenyl-indolizin-3-yl)-acetamide,
N-(6-Dimethylamino-pyridin-3-yl)-2-oxo-2-(2-pyridin-3-yl-indolizin-3-yl)-acetamide,
2-[(E/Z)-2-Dimethylamino-ethoxyimino]-N-(4-methoxy-phenyl)-2-(2-phenyl-indolizin-3-yl)-acetamide,
2-[(E/Z)-3-Dimethylamino-propoxyimino]-N-(4-methoxy-phenyl)-2-(2-phenyl-indolizin-3-yl)-acetamide,
N-(3-Allyl-4-fluoro-2-methoxy-phenyl)-2-oxo-2-(2-phenyl-indolizin-3-yl)-acetamide,
N-[4-(1-Hydroxy-ethyl)-phenyl]-2-oxo-2-(2-phenyl-indolizin-3-yl)-acetamide,
N-(1-Methyl-1H-indol-5-yl)-2-oxo-2-(2-phenyl-indolizin-3-yl)-acetamide,
N-(4-Methanesulfonyl-phenyl)-2-oxo-2-(2-phenyl-indolizin-3-yl)-acetamide,
4-[1-(4-Methoxy-phenylcarbamoyl)-1-(2-phenyl-indolizin-3-yl)-meth-(E/Z)-ylideneaminooxy]-butyric acid,
2-Oxo-2-(2-phenyl-indolizin-3-yl)-N-(4-thiomorpholin-4-yl-phenyl)-acetamide,
2-Oxo-2-(2-phenyl-indolizin-3-yl)-N-(2,3,4-trimethyl-phenyl)-acetamide,
2-Oxo-2-(2-phenyl-indolizin-3-yl)-N-(4-pyrrolidin-1-yl-phenyl)-acetamide,
N-(1-Methyl-2,3-dihydro-1H-indol-5-yl)-2-oxo-2-(2-phenyl-indolizin-3-yl)-acetamide,
N-[4-(4-Methyl-piperazin-1-yl)-phenyl]-2-oxo-2-(2-phenyl-indolizin-3-yl)-acetamide,
N-Benzyl-N-methyl-3-[2-oxo-2-(2-phenyl-indolizin-3-yl)-acetylamino]-benzamide,
N-[4-(2-Methyl-[1,3]dioxolan-2-yl)-phenyl]-2-oxo-2-(2-phenyl-indolizin-3-yl)-acetamide,
N-(2,4-Difluoro-phenyl)-2-[2-(2,4-difluoro-phenyl)-indolizin-3-yl]-2-oxo-acetamide,
Diethyl-carbamic acid 3-[2-oxo-2-(2-phenyl-indolizin-3-yl)-acetylamine]-phenyl ester,
N-(3-Acetyl-phenyl)-2-oxo-2-(2-phenyl-indolizin-3-yl)-acetamide,
1-Methyl-4-{4-[2-oxo-2-(2-phenyl-indolizin-3-yl)-acetylamino]-phenyl}-thiomorpholin-1-ium,
N-(4-Oxazol-2-yl-phenyl)-2-oxo-2-(2-phenyl-indolizin-3-yl)-acetamide,
N-(2,4-Difluoro-phenyl)-2-[2-(2-methoxy-phenyl)-indolizin-3-yl]-2-oxo-acetamide, 2-Oxo-2-(2-phenyl-indolizin-3-yl)-N-[4-(pyridin-2-ylamino)-phenyl]-acetamide, 2-Oxo-2-(2-phenyl-indolizin-3-yl)-N-[4-(1H-tetrazol-5-yl)-phenyl]-acetamide, 2-Oxo-N-[4-(4-oxo-piperidin-1-yl)-phenyl]-2-(2-phenyl-indolizin-3-yl)-acetamide, N-(4-Dimethylamino-3-methyl-phenyl)-2-oxo-2-(2-phenyl-indolizin-3-yl)-acetamide, 2-Dimethylamino-5-[2-oxo-2-(2-phenyl-indolizin-3-yl)-acetylamino]-benzoic acid, 1-{4-[2-Oxo-2-(2-phenyl-indolizin-3-yl)-acetylamino]-phenyl}-pyrrolidine-2-carboxylic acid methyl ester, 2-Oxo-2-(2-phenyl-indolizin-3-yl)-N-[4-(pyrimidin-2-ylamino)-phenyl]-acetamide, 2-[2-(2-Chloro-phenyl)-indolizin-3-yl]-N-(2,4-difluoro-phenyl)-2-oxo-acetamide, N-(4-Dimethylaminomethyl-phenyl)-2-oxo-2-(2-phenyl-indolizin-3-yl)-acetamide, N-(3-Acetyl-4-methoxy-phenyl)-2-oxo-2-(2-phenyl-indolizin-3-yl)-acetamide, 2-[2-(2-Methyl-pyridin-3-yl)-indolizin-3-yl]-2-oxo-N-[4-(2,2,3,3-tetrafluoro-propoxy)-phenyl]-acetamide, 2-Oxo-N-[4-(2-oxo-propyl)-phenyl]-2-(2-phenyl-indolizin-3-yl)-acetamide, 2-Oxo-2-(2-phenyl-indolizin-3-yl)-N-[4-(thiazol-2-ylamino)-phenyl]-acetamide, 2-Oxo-N-[6-(2,2,3,3-tetrafluoro-propoxy)-pyridin-3-yl]-2-(2-o-tolyl-indolizin-3-yl)-acetamide, N-[4-(3,5-Dimethyl-isoxazol-4-yl)-phenyl]-2-oxo-2-(2-phenyl-indolizin-3-yl)-acetamide, N-(3-Oxazol-2-yl-phenyl)-2-oxo-2-(2-phenyl-indolizin-3-yl)-acetamide, N-(6-Dipropylamino-pyridin-3-yl)-2-oxo-2-(2-phenyl-indolizin-3-yl)-acetamide, N-(4-Diethylamino-3-methyl-phenyl)-2-oxo-2-(2-phenyl-indolizin-3-yl)-acetamide, N-(4-Oxazol-5-yl-phenyl)-2-oxo-2-(2-phenyl-indolizin-3-yl)-acetamide, N-(4-Dimethylamino-3-oxazol-2-yl-phenyl)-2-oxo-2-(2-phenyl-indolizin-3-yl)-acetamide, 2-Oxo-2-(2-phenyl-indolizin-3-yl)-N-(4-thiazol-2-yl-phenyl)-acetamide, or a pharmaceutically acceptable salt thereof.

15. A method according to claim 5, wherein the disease is caused by an *Aspergillus* or *Candida* species.

16. A method according to claim 5, wherein the disease is caused by a fungal dermatophyte.

17. A method according to claim 5, wherein the disease is Allergic Bronchopulmonary Aspergillosis (ABPA).

18. A method according to claim 5, wherein the disease is asthma.

19. A method of controlling a fungal disease in a plant, which method comprises applying to the locus of the plant an indolizinyl derivative of formula (I) or an agriculturally acceptable salt thereof:

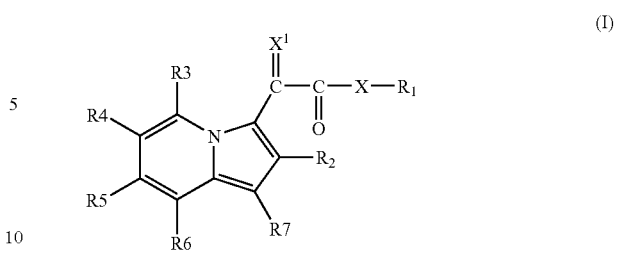

wherein:
X is a bond, —NR8—, —O—, —S—, —SO—, or —SO$_2$—;
X$^1$ is O or NOR9, wherein R9 is hydrogen or an unsubstituted or substituted C1-C4 alkyl group;
R1 represents an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', and —Y—Z;
R8 represents hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', and —Y—Z;
or when X is NR8, R1 and R8 together with the nitrogen to which they are attached may form an unsubstituted or substituted, aromatic or non-aromatic 5- to 12-membered heterocyclyl group;
A1 is an unsubstituted or substituted C6-C10 arylene group;
L1 is a bond, —NR'—, —O—, —CO—, —OCO—, —OCONR'R" or —CONR'R"—;
L2 is a substituted or unsubstituted C1-C4 alkylene or C2-C4 alkenylene group;
A2 is a substituted or unsubstituted C6-C10 aryl or 5- to 12-membered-heterocyclyl group;
R2 is an unsubstituted or substituted group selected from C6-C10 aryl, a 5- to 12-membered heterocyclyl group, C1-C8 alkyl and C3-C6 cycloalkyl, or halogen;
R3, R4, R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;
R7 represents hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;
Y is C1-C8 alkylene, C2-C8 alkenylene or C2-C8 alkynylene;
Z is halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$—NSO$_2$R', —OCONR'R" or —CR'=NOR"; and
R' and R" independently represent hydrogen, C1-C8 alkyl, C2-C8 alkenyl or C2-C8 alkynyl, wherein the substituent(s) on any substituted alkyl, alkenyl or alkynyl group or moiety of R1 to R9, L2 or Y are selected from halogen, hydroxyl, amino, (C1-C4 alkyl)amino, di(C1-C4 alkyl)amino, C1-C4 alkoxy, CO$_2$H and —CO$_2$(C1-C4 alkyl);

the substituent(s) on any substituted cycloalkyl of R1, R2, R8 or Z are selected from C1-C8 alkyl, C2-C8 alkyl, C2-C8 alkenyl, C2-C8 alkynyl, Z and —Y—Z;

the substituent(s) on any substituted aryl or heterocyclyl group or moiety of R1, A1, A2 or R2 to R6 are selected from C1-C8 alkyl, C2-C8 alkenyl, C2-C8 alkynyl, unsubstituted phenyl, Z and —Y—Z, wherein any C1-C4 alkyl or C1-C4 alkoxy substituent on an aryl or heterocyclyl group or moiety may be further substituted with one, two or three unsubstituted groups selected from halogen, hydroxyl, amino, (C1-C4 alkyl)amino, di(C1-C4 alkyl)amino, C1-C4 alkoxy, cyano, —COR$^{41}$ and —CO$_2$R$^{41}$, wherein R$^{41}$ is selected from hydrogen and C1-C4 alkyl, excluding:

6-Hydroxy-alpha-oxo-2-phenyl-3-indolizineacetic acid ethyl ester,
5-Methyl-alpha-oxo-2-phenyl-3-indolizineacetic acid ethyl ester,
ethyl 2-(2,5-dimethylindolizin-3-yl)-2-oxoacetate,
N,N-dimethyl-2-oxo-2-(2-phenyl-indolizin-3-yl)-acetamide,
alpha-Oxo-2-phenyl-N-(4,5,6,7-tetrahydro-2-benzothiazolyl)-3-indolizineacetamide,
N-Cyclohexyl-alpha-oxo-2-phenyl-3-indolizineacetamide,
N-(2,4-Dimethyl-5-nitrophenyl)-alpha-oxo-2-phenyl-3-indolizineacetamide,
N-[3-[(Diethylamino)sulfonyl]phenyl]-alpha-oxo-2-phenyl-3-indolizineacetamide,
N-[2-[4-(Aminosulfonyl)phenyl]ethyl]-alpha-oxo-2-phenyl-3-indolizineacetamide,
2-Chloro-4-fluoro-benzoic acid 3-[[oxo-(2-phenyl-3-indolizinyl)acetyl]amino]propyl ester,
N-[2-(1,1-Dimethylethyl)phenyl]-alpha-oxo-2-phenyl-3-indolizineacetamide,
N-(3-Bromophenyl)-alpha-oxo-2-phenyl-3-indolizineacetamide,
3,5-Dimethyl-1-[oxo(2-phenyl-3-indolizinyl)acetyl]-piperidine,
N-(2-Hydroxyethyl)-alpha-oxo-2-phenyl-3-indolizineacetamide,
N-[2-[(4-Nitrobenzoyl)oxy]ethyl]-alpha-oxo-2-phenyl-3-indolizineacetamide,
2-(4-Chlorophenyl)-alpha-oxo-3-Indolizineacetic acid (2-fluorophenyl)methyl ester,
4-Fluoro-benzoic acid 2-[[[2-(4-chlorophenyl)-3-indolizinyl]oxoacetyl]amino]ethyl ester,
1-[[2-(4-Chlorophenyl)-3-indolizinyl]oxoacetyl]hexahydro-1H-azepine,
2-(4-Chlorophenyl)-alpha-oxo-3-indolizineacetic acid cyclopentyl ester,
2-(4-Chlorophenyl)-N-(2-hydroxyethyl)-alpha-oxo-3-indolizineacetamide,
4-(1,1-Dimethylethyl)-benzoic acid 2-[[[2-(4-chlorophenyl)-3-indolizinyl]oxoacetyl]amino]ethyl ester,
1-[Oxo(2-phenyl-3-indolizinyl)acetyl]-4-phenyl-piperazine,
2,6-Dimethyl-4-[oxo(2-phenyl-3-indolizinyl)acetyl]-morpholine,
N-1,3-Benzodioxol-5-yl-2-(4-chlorophenyl)-alpha-oxo-3-indolizineacetamide,
N-(4-Ethoxyphenyl)-alpha-oxo-2-phenyl-3-indolizineacetamide,
N-(2,4-Dimethylphenyl)-alpha-oxo-2-phenyl-3-indolizineacetamide,
N-(3-Hydroxypropyl)-alpha-oxo-2-phenyl-3-indolizineacetamide,
N-Methyl-N-(1-methyl-4-piperidinyl)-alpha-oxo-2-phenyl-3-indolizineacetamide,
N-[3-[(Diethylamino)sulfonyl]-4-methylphenyl]-alpha-oxo-2-phenyl-3-indolizineacetamide,
N-(6-Methoxy-3-pyridinyl)-alpha-oxo-2-phenyl-3-indolizineacetamide,
N-(3-Methoxyphenyl)-alpha-oxo-2-phenyl-3-indolizineacetamide,
N-[4-Methyl-3-(4-morpholinylsulfonyl)phenyl]-alpha-oxo-2-phenyl-3-indolizineacetamide,
alpha-Oxo-2-phenyl-N-[3-(1-piperidinylsulfonyl)phenyl]-3-indolizineacetamide,
N-(4-Chloro-2-methoxy-5-methylphenyl)-alpha-oxo-2-phenyl-3-indolizineacetamide,
N-(2-Chloro-3-pyridinyl)-alpha-oxo-2-phenyl-3-indolizineacetamide,
N-[2-[[(4-Chlorophenyl)amino]carbonyl]phenyl]-alpha-oxo-2-phenyl-3-indolizineacetamide,
N-[5-[(Diethylamino)sulfonyl]-2-(4-morpholinyl)phenyl]-alpha-oxo-2-phenyl-3-indolizineacetamide,
alpha-Oxo-N-(3-phenoxyphenyl)-2-phenyl-3-indolizineacetamide,
alpha-Oxo-2-phenyl-N-[4-(trifluoromethyl)phenyl]-3-indolizineacetamide,
alpha-Oxo-2-phenyl-N-[4-(1-piperidinyl)phenyl]-3-indolizineacetamide,
4-Chloro-2-nitro-benzoic acid 3-[[oxo(2-phenyl-3-indolizinyl)acetyl]amino]propyl ester,
3-[(2,6-Dimethyl-4-morpholinyl)sulfonyl]-benzoic acid 3-[[oxo(2-phenyl-3-indolizinyl)acetyl]amino]propyl ester,
N-(2,3-Dihydro-1,5-dimethyl-3-oxo-2-phenyl-1H-pyrazol-4-yl)-alpha-oxo-2-phenyl-3-indolizineacetamide,
N-(3,5-Dimethoxyphenyl)-alpha-oxo-2-phenyl-3-indolizineacetamide,
N-(3-Chloro-4-fluorophenyl)-alpha-oxo-2-phenyl-3-indolizineacetamide,
N-[4-[(Diethylamino)sulfonyl]phenyl]-alpha-oxo-2-phenyl-3-indolizineacetamide,
N-(3,4-Dimethylphenyl)-alpha-oxo-2-phenyl-3-indolizineacetamide,
alpha-Oxo-N-(2-phenoxyphenyl)-2-phenyl-3-indolizineacetamide,
N-[5-(1,1-Dimethylethyl)-2-methoxyphenyl]-alpha-oxo-2-phenyl-3-indolizineacetamide,
alpha-Oxo-2-phenyl-N-[4-(1-piperidinylsulfonyl)phenyl]-3-indolizineacetamide,
N-(2,3-Dimethylphenyl)-alpha-oxo-2-phenyl-3-indolizineacetamide,
N-(4-Bromo-2-fluorophenyl)-alpha-oxo-2-phenyl-3-indolizineacetamide,
N-2-Naphthalenyl-alpha-oxo-2-phenyl-3-indolizineacetamide,
N-[2-Chloro-5-(4-morpholinylsulfonyl)phenyl]-alpha-oxo-2-phenyl-3-indolizineacetamide,
2,3-Dichloro-benzoic acid 3-[[oxo(2-phenyl-3-indolizinyl)acetyl]amino]propyl ester,
3,4-Dichloro-benzoic acid 3-[[oxo(2-phenyl-3-indolizinyl)acetyl]amino]propyl ester,
N-(2,4-Dimethoxyphenyl)-alpha-oxo-2-phenyl-3-indolizineacetamide,
2-(4-Chlorophenyl)-alpha-oxo-N-phenyl-3-indolizineacetamide,
4-[[2-(4-Chlorophenyl)-3-indolizinyl]oxoacetyl]-morpholine, N-Ethyl-alpha-oxo-2-phenyl-3-indolizineacetamide,
alpha-Oxo-2-phenyl-N-[3-(trifluoromethyl)phenyl]-3-indolizineacetamide,
4-[[Oxo(2-phenyl-3-indolizinyl)acetyl]amino]-benzoic acid methyl ester,
N,N-Diethyl-alpha-oxo-2-phenyl-3-indolizineacetamide,
N-[2-(Dimethylamino)ethyl]-alpha-oxo-2-phenyl-3-indolizineacetamide,
2-Methyl-alpha-oxo-3-indolizineacetic acid,
N-(2-Methoxyphenyl)-alpha-oxo-2-phenyl-3-indolizineacetamide,
N-1-Naphthalenyl-alpha-oxo-2-phenyl-3-indolizineacetamide,
1,2,3,4-Tetrahydro-6,7-dimethoxy-2-[oxo(2-phenyl-3-indolizinyl)acetyl]-isoquinoline,
N-(1-Cyano-1-methylethyl)-alpha-oxo-2-phenyl-3-indolizineacetamide,
alpha-Oxo-2-phenyl-N-(2-phenylethyl)-3-indolizineacetamide,
Hexahydro-1-[oxo(2-phenyl-3-indolizinyl)acetyl]-1H-azepine,
alpha-Oxo-2-phenyl-N-4H-1,2,4-triazol-4-yl-3-indolizineacetamide,
1,2,3,4-Tetrahydro-1-[oxo(2-phenyl-3-indolizinyl)acetyl]-quinoline,
N-(6-Methoxy-2-benzothiazolyl)-alpha-oxo-2-phenyl-3-indolizineacetamide,
alpha-Oxo-2-phenyl-N-2-thiazolyl-3-indolizineacetamide,
N-[(4-Methoxyphenyl)methyl]-alpha-oxo-2-phenyl-3-indolizineacetamide,
N-[(4-Bromophenyl)methyl]-alpha-oxo-2-phenyl-3-indolizineacetamide,
N-(1,1-Dimethylethyl)-alpha-oxo-2-phenyl-3-indolizineacetamide,
N-Butyl-alpha-oxo-2-phenyl-3-indolizineacetamide,
alpha-Oxo-N-[(3-phenoxyphenyl)methyl]-2-phenyl-3-indolizineacetamide,
N-Ethyl-alpha-oxo-N,2-diphenyl-3-indolizineacetamide,
alpha-Oxo-N,2-diphenyl-3-indolizineacetamide,
N-[2-(3,4-Dimethoxyphenyl)ethyl]-alpha-oxo-2-phenyl-3-indolizineacetamide,
alpha-Oxo-2-phenyl-N-(phenylmethyl)-3-indolizineacetamide,
4-[Oxo(2-phenyl-3-indolizinyl)acetyl]-morpholine,
N-(4-Methylphenyl)-alpha-oxo-2-phenyl-3-indolizineacetamide,
2-Methyl-alpha-oxo-3-indolizineacetic acid ethyl ester,
N,N-Dimethyl-2-phenyl-3-indolizineglyoxylamide,
2-Oxo-2-(2-phenyl-indolizin-3-yl)-N-(4-trifluoromethyl-phenyl)-acetamide,
N-(2,4-Dichloro-phenyl)-2-oxo-2-(2-phenyl-indolizin-3-yl)-acetamide,
2-Oxo-2-(2-phenyl-indolizin-3-yl)-N-(3-trifluoromethyl-phenyl)-acetamide,
2-Oxo-2-(2-phenyl-indolizin-3-yl)-N-(4-piperidin-1-yl-phenyl)-acetamide
1-(5-methyl-2-phenyl-indolizin-3-yl)propane-1,2-dione
1-(5-methyl-2-phenyl-indolizin-3-yl)-propane-1,2-dione 1-oxime
1-(2,5-dimethyl-indolizin-3-yl)-2-phenyl-ethane-1,2-dione 1-oxime
1-(5-methyl-2-phenyl-indolizin-3-yl)-2-phenyl-ethane-1,2-dione 1-oxime
1-(2,5-dimethyl-indolizin-3-yl)-propane-1,2-dione 1-oxime
2-oxo-2-(2-phenylindolizin-3-yl)acetamide and their pharmaceutically or agriculturally acceptable salts thereof.

20. A method according to claim 19, wherein X is —NR8- or —O—.

21. A method according to claim 19 wherein R1 is phenyl, pyridinyl, thiophenyl, furanyl, benzimidazolyl, indolyl, dihydroindolyl, unsubstituted C5-C6 cycloalkyl, C1-C4 alkyl which is unsubstituted or substituted with C1-C4 alkoxy or —CO$_2$(C1-C4 alkyl), -A1-L1-A2 or -L2-A2, wherein the aryl and heterocyclyl groups are unsubstituted or substituted with one, two or three substituents selected from the unsubstituted groups halogen, —CO$_2$R', —CONR'R", OCOR', hydroxyl, cyano, —NR'R", —COR', —NSO$_2$R', —O(C2-C4 alkenyl), C2-C4 alkenyl, —SO$_2$R', —OCONR'R" and —CR'=NOR", and from C1-C4 alkyl and C1-C4 alkoxy groups which are unsubstituted or substituted with from one to four unsubstituted groups selected from halogen, hydroxyl, di(C1-C4 alkyl)amino, cyano, —COR' and —CO$_2$R', wherein R' and R" are independently selected from hydrogen and C1-C4 alkyl.

22. A method according to claim 19, wherein A1 is unsubstituted phenyl or phenyl substituted with a group —NR'R", wherein R' and R" are independently selected from hydrogen and C1-C4 alkyl; L1 is a bond, —NH— or —CONR'R"—, wherein R' and R" are independently selected from hydrogen and C1-C4 alkyl groups and moieties; L2 is C1-C4 alkylene which is unsubstituted or substituted with one or two substituents selected from halogen, C1-C4 alkoxy and —CO$_2$(C1-C4 alkyl); and A2 is phenyl or a 5- to 6-membered heterocyclyl group containing one, two, three or four heteroatoms selected from N, O and S, wherein the heterocycle is unsubstituted or substituted with one or two substituents selected from C1-C4 alkyl and CO$_2$(C1-C4 alkyl).

23. A method according to claim 19 wherein R2 is phenyl or pyridinyl optionally substituted with halogen, unsubstituted C1-C4 alkyl, unsubstituted C1-C4 alkoxy or cyano, or unsubstituted thiophenyl or furanyl.

24. A method according to claim 23, wherein X is NR8 and R3, R4, R5, R6 and R7 are selected from hydrogen, halogen, C1-C4 alkyl or C1-C4 alkoxy.

25. A method according to claim 19, wherein X is NR8 and R8 is hydrogen or unsubstituted C1-C4 alkyl.

26. A method according to claim 19, wherein
X is —NR8— or —O—;
$X^1$ is O or NOR9, wherein R9 is a linear C1-C4 alkyl group which is unsubstituted or substituted with a single substituent on the terminal carbon atom, the substituent being selected from di(C1-C4 alkyl)amino and —CO$_2$H;
R1 is phenyl, pyridinyl, thiophenyl, furanyl, benzimidazolyl, indolyl, dihydroindolyl, unsubstituted C5-C6 cycloalkyl, C1-C4 alkyl which is unsubstituted or substituted with C1-C4 alkoxy or —CO$_2$(C1-C4 alkyl), -A1-L1-A2 or -L2-A2, wherein the aryl and heterocyclyl groups are unsubstituted or substituted with one, two or three substituents selected from the unsubstituted groups halogen, —CO$_2$R', —CONR'R", OCOR', hydroxyl, cyano, —NR'R", —COR', —NSO$_2$R', —O(C2-C4 alkenyl), C2-C4 alkenyl, —SO$_2$R', —OCONR'R" and —CR'=NOR", and from C1-C4 alkyl and C1-C4 alkoxy groups which are unsubstituted or substituted with from one to four unsubstituted groups selected from halogen, hydroxyl, di(C1-C4 alkyl)amino, cyano, —COR' and —CO$_2$R', wherein R' and R" are independently selected from hydrogen and C1-C4 alkyl;

A1 is unsubstituted phenyl or phenyl substituted with a group —NR'R", wherein R' and R" are independently selected from hydrogen and C1-C4 alkyl;

L1 is a bond, —NH— or —CONR'R"—, wherein R' and R" are independently selected from hydrogen and C1-C4 alkyl groups and moieties;

L2 is C1-C4 alkylene which is unsubstituted or substituted with one or two substituents selected from halogen, C1-C4 alkoxy and —CO$_2$(C1-C4 alkyl);

A2 is phenyl or a 5- to 6-membered heterocyclyl group containing one, two, three or four heteroatoms selected from N, O and S, wherein the heterocycle is unsubstituted or substituted with one or two substituents selected from C1-C4 alkyl and CO$_2$(C1-C4 alkyl);

R8 is hydrogen or unsubstituted C1-C4 alkyl; or when X is NR8, R1 and R8 together with the nitrogen atom to which they are attached may form a 5- to 12-membered heterocyclyl group preferably selected from piperidinyl, morpholinyl, azepanyl or dihydroindolyl;

R2 is unsubstituted or substituted phenyl, unsubstituted or substituted pyridinyl, or unsubstituted thiophenyl or furanyl, the substituents being selected from halogen, unsubstituted C1-C4 alkyl, unsubstituted C1-C4 alkoxy and cyano;

R3 to R6 are independently selected from hydrogen, unsubstituted C1-C4 alkyl and unsubstituted C1-C4 alkoxy; and R7 is hydrogen.

27. A method according to claim 19 wherein the compound is:

N-(2-Methoxy-phenyl)-2-oxo-2-(2-phenyl-indolizin-3-yl)-acetamide,
4-[2-Oxo-2-(2-phenyl-indolizin-3-yl)-acetylamine]-benzoic acid methyl ester,
2-Oxo-N-phenyl-2-(2-phenyl-indolizin-3-yl)-acetamide,
4-[2-Oxo-2-(-phenyl-indolizin-3-yl)-acetylamino]-benzoic acid propyl ester,
2-[2-Oxo-2-(2-phenyl-indolizin-3-yl)-acetylamine]-benzoic acid methyl ester,
3-[2-Oxo-2-(2-phenyl-indolizin-3-yl)-acetylamine]-benzoic acid methyl ester,
4-[2-Oxo-2-(-phenyl-indolizin-3-yl)-acetylamino]-benzoic acid propyl ester,
4-[2-Oxo-2-(2-phenyl-indolizin-3-yl)-acetylamino]-benzoic acid butyl ester,
N-(3-Methoxy-phenyl)-2-oxo-2-(2-phenyl-indolizin-3-yl)-acetamide,
N-(4-Methoxy-phenyl)-2-oxo-2-(2-phenyl-indolizin-3-yl)-acetamide,
N-(4-Hydroxy-phenyl)-2-oxo-2-(2-phenyl-indolizin-3-yl)-acetamide,
N-(4-Chloro-phenyl)-2-oxo-2-(2-phenyl-indolizin-3-yl)-acetamide,
N-(4-Cyano-phenyl)-2-oxo-2-(2-phenyl-indolizin-3-yl)-acetamide,
2-Oxo-2-(2-phenyl-indolizin-3-yl)-N-p-tolyl-acetamide,
2-Oxo-2-(2-phenyl-indolizin-3-yl)-N-pyridin-4-yl-acetamide,
2-Oxo-2-(2-phenyl-indolizin-3-yl)-N-pyridin-3-yl-acetamide,
2-Oxo-2-(2-phenyl-indolizin-3-yl)-N-pyridin-2-yl-acetamide,
4-[2-Oxo-2-(2-phenyl-indolizin-3-yl)-acetylamine]-benzoic acid,
N-(2,4-Dimethoxy-phenyl-phenyl)-2-oxo-2-(2-phenyl-indolizin-3-yl)-acetamide,
N-(6-Methoxy-pyridin-3-yl)-2-oxo-2-(2-phenyl-indolizin-3-yl)-acetamide,
4-[2-Oxo-2-(2-phenyl-indolizin-3-yl)-acetylamine]-benzamide,
N-Methyl-4-[2-oxo-2-(2-phenyl-indolizin-3-yl)-acetylamino]-benzamide,
N,N-Dimethyl-4-[2-oxo-2-(2-phenyl-indolizin-3-yl)-acetamino]-benzamide,
5-[2-Oxo-2-(2-phenyl-indolizin-3-yl)-acetylamino]-thiophene-3-carboxylic acid methyl ester,
N-(4-Methoxy-phenyl)-2-oxo-2-(2-pyridin-4-yl-indolizin-3-yl)-acetamide,
N-(4-Methoxy-phenyl)-2-oxo-2-(2-pyridin-3-yl-indolizin-3-yl)-acetamide,
N-(4-Methoxy-phenyl)-2-oxo-2-(2-pyridin-2-yl-indolizin-3-yl)-acetamide,
N-(4-Methoxy-phenyl)-2-oxo-2-(2-thiophen-2-yl-indolizin-3-yl)-acetamide,
2-(2-Furan-2-yl-indolizin-3-yl)-N-(4-methoxy-phenyl)-2-oxo-acetamide,
2-[2-(4-Fluoro-phenyl)-indolizin-3-yl]-N-(4-methoxy-phenyl)-2-oxo-acetamide,
2-[2-(4-Fluoro-phenyl)-indolizin-3-yl]-2-oxo-N-p-tolyl-acetamide,
N-(2-,4-Dimethoxy-phenyl)-2-[2-(4-fluoro-phenyl)-indolizin-3-yl]-2-oxo-acetamide,
2-[2-(4-Fluoro-phenyl)-indolizin-3-yl]-N-(6-methoxy-pyridin-3-yl)-2-oxo-acetamide,
2-Oxo-2-(2-thiophen-2-yl-indolizin-3-yl)-N-p-tolyl-acetamide,
N-(2,4-Dimethoxy-phenyl)-2-oxo-2-(2-thiophen-2-yl-indolizin-3-yl)-acetamide,
N-(6-Methoxy-pyridin-3-yl)-2-oxo-2-(2-thiophen-2-yl-indolizin-3-yl)-acetamide,
2-(2-Furan-2-yl-indolizin-3-yl)-2-oxo-N-p-tolyl-acetamide,
N-(2,4-Dimethoxy-phenyl)-2-(2-furan-2-yl-indolizin-3-yl)-2-oxo-acetamide,
2-(2-Furan-2-yl-indolizin-3-yl)-N-(6-methoxy-pyridin-3-yl)-2-oxo-acetamide,
2-Oxo-2-(2-pyridin-4-yl-indolizin-3-yl)-N-p-tolyl-acetamide,
N-(2,4-Dimethoxy-phenyl)-2-oxo-2-(2-pyridin-4-yl-indolizin-3-yl)-acetamide,
N-(6-Methoxy-pyridin-3-yl)-2-oxo-2-(2-pyridin-4-yl-indolizin-3-yl)-acetamide,
2-Oxo-2-(2-pyridin-3-yl-indolizin-3-yl)-N-p-tolyl-acetamide,
N-(2,4-Dimethoxy-phenyl)-2-oxo-2-(2-pyridin-3-yl-indolizin-3-yl)-acetamide,
N-(6-Methoxy-pyridin-3-yl)-2-oxo-2-(2-pyridin-3-yl-indolizin-3-yl)-acetamide,
2-Oxo-2-(2-pyridin-2-yl-indolizin-3-yl)-N-p-tolyl-acetamide,
N-(2,4-Dimethoxy-phenyl)-2-oxo-2-(2-pyridin-2-yl-indolizin-3-yl)-acetamide,
N-(6-Methoxy-pyridin-3-yl)-2-oxo-2-(2-pyridin-2-yl-indolizin-3-yl)-acetamide,
Oxo-(2-phenyl-indolizin-3-yl)-thioacetic acid S-(2-methoxy-phenyl) ester,
4-[2-Oxo-2-(2-phenyl-indolizin-3-yl)-acetoxy]-benzoic acid methyl ester,
N-Cyclohexyl-2-oxo-2-(2-phenyl-indolizin-3-yl)-acetamide,
N-Methyl-2-oxo-2-(2-phenyl-indolizin-3-yl)-acetamide,
N-Isopropyl-2-oxo-2-(2-phenyl-indolizin-3-yl)-acetamide, N-(2-Methoxy-ethyl)-2-oxo-2-(2-phenyl-indolizin-3-yl)-acetamide,
N-Benzyl-2-oxo-2-(2-phenyl-indolizin-3-yl)-acetamide,
N,N-Dimethyl-2-oxo-2-(2-phenyl-indolizin-3-yl)-acetamide,
1-(2-Phenyl-indolizin-3-yl)-2-piperidin-1-yl-ethane-1,2-dione,
N-(2-Methoxy-ethyl)-2-oxo-2-(2-pyridin-3-yl-indolizin-3-yl)-acetamide,
N-Methyl-2-oxo-N-phenyl-2-(2-phenyl-indolizin-3-yl)-acetamide,
N-Methyl-2-oxo-N-phenyl-2-(2-pyridin-3-yl-indolizin-3-yl)-acetamide,
2-(5-Methyl-2-phenyl-indolizin-3-yl)-2-oxo-N-p-tolyl-acetamide,
N-(6-Methoxy-pyridin-3-yl)-2-(5-methyl-2-phenyl-indolizin-3-yl)-2-oxo-acetamide,
2-(6-Methyl-2-phenyl-indolizin-3-yl)-2-oxo-N-p-tolyl-acetamide,
2-(7-Methyl-2-phenyl-indolizin-3-yl)-2-oxo-N-p-tolyl-acetamide,
N-(6-Methoxy-pyridin-3-yl)-2-(6-methyl-2-phenyl-indolizin-3-yl)-2-oxo-acetamide,
N-(6-Methoxy-pyridin-3-yl)-2-(7-methyl-2-phenyl-indolizin-3-yl)-2-oxo-acetamide,
N-(6-Methoxy-pyridin-3-yl)-2-(8-methyl-2-phenyl-indolizin-3-yl)-2-oxo-acetamide,
2-(6-Methoxy-2-phenyl-indolizin-3-yl)-N-(6-methoxy-pyridin-3-yl)-2-oxo-acetamide,
2-(6-Methoxy-2-phenyl-indolizin-3-yl)-2-oxo-N-p-tolyl-acetamide,
N-(4-Chloro-phenyl)-2-oxo-2-(2-pyridin-3-yl-indolizin-3-yl)-acetamide,
N-(4-Fluoro-phenyl)-2-oxo-2-(2-pyridin-3-yl-indolizin-3-yl)-acetamide,
2-(6-Methyl-2-pyridin-3-yl-indolizin-3-yl)-2-oxo-N-p-tolyl-acetamide,
N-(4-Fluoro-phenyl)-2-oxo-2-(2-phenyl-indolizin-3-yl)-acetamide,
N-(2-Fluoro-phenyl)-2-oxo-2-(2-phenyl-indolizin-3-yl)-acetamide,
2-Oxo-2-(2-phenyl-indolizin-3-yl)-N-(4-trifluoromethyl-phenyl)-acetamide,
2-Oxo-2-(2-phenyl-indolizin-3-yl)-N-o-tolyl-acetamide,
N-(4-Dimethylamino-phenyl)-2-oxo-2-(2-phenyl-indolizin-3-yl)-acetamide,
N-(4-Bromo-phenyl)-2-oxo-2-(2-phenyl-indolizin-3-yl)-acetamide,
N-(4-Acetyl-phenyl)-2-oxo-2-(2-phenyl-indolizin-3-yl)-acetamide,
2-Oxo-2-(2-phenyl-indolizin-3-yl)-N-m-tolyl-acetamide,
N-(2-Chloro-phenyl)-2-oxo-2-(2-phenyl-indolizin-3-yl)-acetamide,
2-[2-Oxo-2-(2-phenyl-indolizin-3-yl)-acetylamino]-benzoic acid ethyl ester,
N-(2,4-Dichloro-phenyl)-2-oxo-2-(2-phenyl-indolizin-3-yl)-acetamide,
N-(4-Fluoro-phenyl)-2-[2-(4-fluoro-phenyl)-indolizin-3-yl]-2-oxo-acetamide,
N-(4-Chloro-phenyl)-2-[2-(4-fluoro-phenyl)-indolizin-3-yl]-2-oxo-acetamide,
N-(2-Fluoro-phenyl)-2-oxo-2-(2-pyridin-3-yl-indolizin-3-yl)-acetamide,
2-Oxo-2-(2-pyridin-3-yl-indolizin-3-yl)-N-(4-trifluoromethyl-phenyl)-acetamide,
2-Oxo-2-(2-pyridin-3-yl-indolizin-3-yl)-N-o-tolyl-acetamide,
N-(4-Bromo-phenyl)-2-oxo-2-(2-pyridin-3-yl-indolizin-3-yl)-acetamide,
2-Oxo-2-(2-pyridin-3-yl-indolizin-3-yl)-N-m-tolyl-acetamide,
N-(2-Chloro-phenyl)-2-oxo-2-(2-pyridin-3-yl-indolizin-3-yl)-acetamide,
N-(4-Acetyl-phenyl)-2-oxo-2-(2-pyridin-3-yl-indolizin-3-yl)-acetamide,
2-Oxo-2-(2-phenyl-indolizin-3-yl)-N-(3-trifluoromethyl-phenyl)-acetamide,
1-(2,3-Dihydro-indol-1-yl)-2-(2-phenyl-indolizin-3-yl)-ethane-1,2-dione,
N-(4-Methanesulfonylamino-phenyl)-2-oxo-2-(2-phenyl-indolizin-3-yl)-acetamide,
N-(3,5-Dichloro-phenyl)-2-oxo-2-(2-phenyl-indolizin-3-yl)-acetamide,
N-[4-(Cyano-dimethyl-methyl)-phenyl]-2-oxo-2-(2-phenyl-indolizin-3-yl)-acetamide,
2-Oxo-2-(2-phenyl-indolizin-3-yl)-N-(3,4,5-trimethoxy-phenyl)-acetamide,
2-Oxo-2-(2-pyridin-3-yl-indolizin-3-yl)-N-(3-trifluoromethyl-phenyl)-acetamide,
N-(2,4-Dichloro-phenyl)-2-oxo-2-(2-pyridin-3-yl-indolizin-3-yl)-acetamide,
N-[4-(Cyano-dimethyl-methyl)-phenyl]-2-oxo-2-(2-pyridin-3-yl-indolizin-3-yl)-acetamide,
2-Oxo-2-(2-pyridin-3-yl-indolizin-3-yl)-N-(3,4,5-trimethoxy-phenyl)-acetamide,
N-(3,5-Dichloro-phenyl)-2-oxo-2-(2-pyridin-3-yl-indolizin-3-yl)-acetamide,
N-[3-(Cyano-dimethyl-methyl)-phenyl]-2-oxo-2-(2-phenyl-indolizin-3-yl)-acetamide,
N-(6-Dimethylamino-pyridin-3-yl)-2-oxo-2-(2-phenyl-indolizin-3-yl)-acetamide,
N-(4-Dimethylamino-phenyl)-2-oxo-2-(2-pyridin-3-yl-indolizin-3-yl)-acetamide,
N-[3-(Cyano-dimethyl-methyl)-phenyl]-2-oxo-2-(2-pyridin-3-yl-indolizin-3-yl)-acetamide,
2-[(E/Z)-Methoxyimino]-N-(4-methoxy-phenyl)-2-(2-phenyl-indolizin-3-yl)-acetamide,
N-(4-Methoxy-phenyl)-2-oxo-2-(2-o-tolyl-indolizin-3-yl)-acetamide,
N-(4-Methoxy-phenyl)-2-oxo-2-(2-m-tolyl-indolizin-3-yl)-acetamide,
N-(4-Methoxy-phenyl)-2-(8-methyl-2-phenyl-indolizin-3-yl)-2-oxo-acetamide,
2-[2-(3-Chloro-phenyl)-indolizin-3-yl]-N-(4-methoxy-phenyl)-2-oxo-acetamide,
2-[2-(3-Cyano-phenyl)-indolizin-3-yl]-N-(4-methoxy-phenyl)-2-oxo-acetamide,
N-(4-Methoxy-phenyl)-2-(5-methyl-2-phenyl-indolizin-3-yl)-2-oxo-acetamide,
N-(4-Methoxy-phenyl)-2-oxo-2-(2-p-tolyl-indolizin-3-yl)-acetamide,
N-(4-Methoxy-phenyl)-2-(6-methoxy-2-phenyl-indolizin-3-yl)-2-oxo-acetamide,
N-[3-(2-Dimethylamino-ethoxy)-phenyl]-2-oxo-2-(2-phenyl-indolizin-3-yl)-acetamide,
N-(3-Methyl-3H-benzoimidazol-5-yl)-2-oxo-2-(2-phenyl-indolizin-3-yl)-acetamide,
N-(1-Methyl-1H-benzoimidazol-5-yl)-2-oxo-2-(2-phenyl-indolizin-3-yl)-acetamide,
N-(4-Dimethylamino-phenyl)-2-(6-methoxy-2-phenyl-indolizin-3-yl)-2-oxo-acetamide,
N-(4-{1-[(E/Z)-Methoxyimino]-ethyl}-phenyl)-2-oxo-2-(2-phenyl-indolizin-3-yl)-acetamide, N-(2,4-Difluoro-phenyl)-2-[2-(3-fluoro-phenyl)-indolizin-3-yl]-2-oxo-acetamide,
2-[2-(3-Cyano-phenyl)-indolizin-3-yl]-N-(2,4-difluoro-phenyl)-2-oxo-acetamide,
N-(5-Chloro-2-methyl-phenyl)-2-oxo-2-(2-phenyl-indolizin-3-yl)-acetamide,
{3-[2-Oxo-2-(2-phenyl-indolizin-3-yl)-acetylamino]-phenoxy}-acetic acid,
N-(2-Allyloxy-4-fluoro-phenyl)-2-oxo-2-(2-phenyl-indolizin-3-yl)-acetamide,
2-Methyl-2-[2-oxo-2-(2-phenyl-indolizin-3-yl)-acetylamino]-propionic acid ethyl ester,
2-Methyl-2-[2-oxo-2-(2-phenyl-indolizin-3-yl)-acetylamino]-3-phenyl-propionic acid ethyl ester,
N-(4-{1-[(E/Z)-Hydroxyimino]-ethyl}-phenyl)-2-oxo-2-(2-phenyl-indolizin-3-yl)-acetamide,
2-Oxo-2-(2-phenyl-indolizin-3-yl)-N-(4-piperidin-1-yl-phenyl)-acetamide,
N-(4-Morpholin-4-yl-phenyl)-2-oxo-2-(2-phenyl-indolizin-3-yl)-acetamide,
N-(4-Isopropyl-phenyl)-2-oxo-2-(2-phenyl-indolizin-3-yl)-acetamide,
N-(6-Dimethylamino-pyridin-3-yl)-2-oxo-2-(2-pyridin-3-yl-indolizin-3-yl)-acetamide,
2-[(E/Z)-2-Dimethylamino-ethoxyimino]-N-(4-methoxy-phenyl)-2-(2-phenyl-indolizin-3-yl)-acetamide,
2-[(E/Z)-3-Dimethylamino-propoxyimino]-N-(4-methoxy-phenyl)-2-(2-phenyl-indolizin-3-yl)-acetamide,
N-(3-Allyl-4-fluoro-2-methoxy-phenyl)-2-oxo-2-(2-phenyl-indolizin-3-yl)-acetamide,
N-[4-(1-Hydroxy-ethyl)-phenyl]-2-oxo-2-(2-phenyl-indolizin-3-yl)-acetamide,
N-(1-Methyl-1H-indol-5-yl)-2-oxo-2-(2-phenyl-indolizin-3-yl)-acetamide,
N-(4-Methanesulfonyl-phenyl)-2-oxo-2-(2-phenyl-indolizin-3-yl)-acetamide,
4-[1-(4-Methoxy-phenylcarbamoyl)-1-(2-phenyl-indolizin-3-yl)-meth-(E/Z)-ylideneaminooxy]-butyric acid,
2-Oxo-2-(2-phenyl-indolizin-3-yl)-N-(4-thiomorpholin-4-yl-phenyl)-acetamide,
2-Oxo-2-(2-phenyl-indolizin-3-yl)-N-(2,3,4-trimethyl-phenyl)-acetamide,
2-Oxo-2-(2-phenyl-indolizin-3-yl)-N-(4-pyrrolidin-1-yl-phenyl)-acetamide,
N-(1-Methyl-2,3-dihydro-1H-indol-5-yl)-2-oxo-2-(2-phenyl-indolizin-3-yl)-acetamide,
N-[4-(4-Methyl-piperazin-1-yl)-phenyl]-2-oxo-2-(2-phenyl-indolizin-3-yl)-acetamide,
N-Benzyl-N-methyl-3-[2-oxo-2-(2-phenyl-indolizin-3-yl)-acetylamino]-benzamide,
N-[4-(2-Methyl-[1,3]dioxolan-2-yl)-phenyl]-2-oxo-2-(2-phenyl-indolizin-3-yl)-acetamide,
N-(2,4-Difluoro-phenyl)-2-[2-(2,4-difluoro-phenyl)-indolizin-3-yl]-2-oxo-acetamide,
Diethyl-carbamic acid 3-[2-oxo-2-(2-phenyl-indolizin-3-yl)-acetylamine]-phenyl ester,
N-(3-Acetyl-phenyl)-2-oxo-2-(2-phenyl-indolizin-3-yl)-acetamide,
1-Methyl-4-{4-[2-oxo-2-(2-phenyl-indolizin-3-yl)-acetylamino]-phenyl}-thiomorpholin-1-ium,
N-(4-Oxazol-2-yl-phenyl)-2-oxo-2-(2-phenyl-indolizin-3-yl)-acetamide,
N-(2,4-Difluoro-phenyl)-2-[2-(2-methoxy-phenyl)-indolizin-3-yl]-2-oxo-acetamide,
2-Oxo-2-(2-phenyl-indolizin-3-yl)-N-[4-(pyridin-2-ylamino)-phenyl]-acetamide,
2-Oxo-2-(2-phenyl-indolizin-3-yl)-N-[4-(1H-tetrazol-5-yl)-phenyl]-acetamide,
2-Oxo-N-[4-(4-oxo-piperidin-1-yl)-phenyl]-2-(2-phenyl-indolizin-3-yl)-acetamide,
N-(4-Dimethylamino-3-methyl-phenyl)-2-oxo-2-(2-phenyl-indolizin-3-yl)-acetamide,
2-Dimethylamino-5-[2-oxo-2-(2-phenyl-indolizin-3-yl)-acetylamino]-benzoic acid,
1-{4-[2-Oxo-2-(2-phenyl-indolizin-3-yl)-acetylamino]-phenyl}-pyrrolidine-2-carboxylic acid methyl ester,
2-Oxo-2-(2-phenyl-indolizin-3-yl)-N-[4-(pyrimidin-2-ylamino)-phenyl]-acetamide,
2-[2-(2-Chloro-phenyl)-indolizin-3-yl]-N-(2,4-difluoro-phenyl)-2-oxo-acetamide,
N-(4-Dimethylaminomethyl-phenyl)-2-oxo-2-(2-phenyl-indolizin-3-yl)-acetamide,
N-(3-Acetyl-4-methoxy-phenyl)-2-oxo-2-(2-phenyl-indolizin-3-yl)-acetamide,
2-[2-(2-Methyl-pyridin-3-yl)-indolizin-3-yl]-2-oxo-N-[4-(2,2,3,3-tetrafluoro-propoxy)-phenyl]-acetamide,
2-Oxo-N-[4-(2-oxo-propyl)-phenyl]-2-(2-phenyl-indolizin-3-yl)-acetamide,
2-Oxo-2-(2-phenyl-indolizin-3-yl)-N-[4-(thiazol-2-ylamino)-phenyl]-acetamide,
2-Oxo-N-[6-(2,2,3,3-tetrafluoro-propoxy)-pyridin-3-yl]-2-(2-o-tolyl-indolizin-3-yl)-acetamide,
N-[4-(3,5-Dimethyl-isoxazol-4-yl)-phenyl]-2-oxo-2-(2-phenyl-indolizin-3-yl)-acetamide,
N-(3-Oxazol-2-yl-phenyl)-2-oxo-2-(2-phenyl-indolizin-3-yl)-acetamide,
N-(6-Dipropylamino-pyridin-3-yl)-2-oxo-2-(2-phenyl-indolizin-3-yl)-acetamide,
N-(4-Diethylamino-3-methyl-phenyl)-2-oxo-2-(2-phenyl-indolizin-3-yl)-acetamide,
N-(4-Oxazol-5-yl-phenyl)-2-oxo-2-(2-phenyl-indolizin-3-yl)-acetamide,
N-(4-Dimethylamino-3-oxazol-2-yl-phenyl)-2-oxo-2-(2-phenyl-indolizin-3-yl)-acetamide,
2-Oxo-2-(2-phenyl-indolizin-3-yl)-N-(4-thiazol-2-yl-phenyl)-acetamide,
or an agriculturally acceptable salt thereof.

* * * * *